United States Patent
Buttar et al.

(10) Patent No.: US 12,006,319 B2
(45) Date of Patent: Jun. 11, 2024

(54) MONOHYDRATE AND CRYSTALLINE FORMS OF 6-[(3S,4S)-4-METHYL-1-(PYRIMIDIN-2-YLMETHYL)PYRROLIDIN-3-YL]-3-TETRAHYDROPYRAN-4-YL-7H-IMIDAZO[1,5-A]PYRAZIN-8-ONE

(71) Applicant: Cardurion Pharmaceuticals, Inc., Burlington, MA (US)

(72) Inventors: Suzanne Buttar, Cambridge (GB); Mateusz Pitak, Cambridge (GB); Adam Ross Patterson, Cambridge (GB); Samuel Alexander Stratford, Cambridge (GB); Ioana Sovago, Cambridge (GB); Jun Xu, Cambridge (GB); Peng Zhou, Cambridge (GB); Haojuan Wei, Changzhou (CN); Kuangchu Dai, Changzhou (CN)

(73) Assignee: Cardurion Pharmaceuticals, Inc., Burlington, MA (US)

( * ) Notice: Subject to any disclaimer, the term of this patent is extended or adjusted under 35 U.S.C. 154(b) by 764 days.

(21) Appl. No.: 17/110,000

(22) Filed: Dec. 2, 2020

(65) Prior Publication Data
US 2021/0107911 A1   Apr. 15, 2021

Related U.S. Application Data

(63) Continuation of application No. PCT/US2019/033835, filed on May 23, 2019.

(60) Provisional application No. 62/788,323, filed on Jan. 4, 2019, provisional application No. 62/676,381, filed on May 25, 2018.

(51) Int. Cl.
C07D 487/04   (2006.01)
A61K 31/4985   (2006.01)

(52) U.S. Cl.
CPC ........ C07D 487/04 (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 3,578,687 A | 5/1971 | Larkin et al. |
| 3,819,561 A | 6/1974 | Bruenner |
| 3,917,660 A | 11/1975 | Sasaki et al. |
| 4,599,430 A | 7/1986 | Milberger et al. |
| 5,412,137 A | 5/1995 | Prashad et al. |
| 5,716,988 A | 2/1998 | Ibrahim et al. |
| 5,741,211 A | 4/1998 | Renirie et al. |
| 5,919,816 A | 7/1999 | Hausheer et al. |
| 6,187,747 B1 | 2/2001 | Singh et al. |
| 6,262,029 B1 | 7/2001 | Press et al. |
| 6,346,231 B1 | 2/2002 | Opheim |
| 6,362,178 B1 | 3/2002 | Niewohner et al. |
| 6,376,688 B1 | 4/2002 | Ferrante et al. |
| 6,407,075 B1 | 6/2002 | Scott et al. |
| 6,410,802 B1 | 6/2002 | Dasseux et al. |
| 6,531,150 B1 | 3/2003 | Sunohara et al. |
| 6,652,879 B2 | 11/2003 | Opheim |
| 6,924,309 B2 | 8/2005 | Ferrante et al. |
| 6,998,395 B2 | 2/2006 | Jackson et al. |
| 7,312,191 B2 | 12/2007 | Rose et al. |
| 7,326,421 B2 | 2/2008 | Brekke et al. |
| 7,452,907 B2 | 11/2008 | Cheng et al. |
| 7,709,468 B2 | 5/2010 | Calderwood et al. |
| 7,741,324 B2 | 6/2010 | Crew et al. |
| 7,776,916 B2 | 8/2010 | Freeman et al. |
| 7,977,315 B2 | 7/2011 | Rose et al. |
| 8,299,080 B2 | 10/2012 | Okada et al. |
| 8,309,526 B2 | 11/2012 | Freeman et al. |
| 8,324,277 B2 | 12/2012 | Freeman |
| 8,563,565 B2 | 10/2013 | Norimine et al. |
| 8,563,609 B2 | 10/2013 | Miller |
| 8,686,038 B2 | 4/2014 | Yang |
| 8,686,167 B2 | 4/2014 | Miller |
| 8,735,449 B2 | 5/2014 | Freeman |
| 8,933,255 B2 | 1/2015 | Miller |
| 8,937,194 B2 | 1/2015 | Miller |
| 9,006,473 B2 | 4/2015 | Freeman et al. |
| 9,066,902 B2 | 6/2015 | Freeman et al. |
| 9,186,408 B2 | 11/2015 | Freeman et al. |
| 9,192,600 B2 | 11/2015 | Yang |
| 9,271,952 B2 | 3/2016 | Cushing |
| 9,295,678 B2 | 3/2016 | Freeman et al. |
| 9,308,189 B2 | 4/2016 | Miller |
| 9,434,731 B2 | 9/2016 | Siegel et al. |
| 9,434,733 B2 | 9/2016 | Svenstrup et al. |
| 9,522,156 B2 | 12/2016 | Freeman et al. |
| 9,533,992 B2 | 1/2017 | Svenstrup et al. |
| 9,585,855 B2 | 3/2017 | Yang |
| 9,643,970 B2 | 5/2017 | Svenstrup et al. |

(Continued)

FOREIGN PATENT DOCUMENTS

AU   2011202664 B2   4/2012
CA   2296224 A1   7/2000

(Continued)

OTHER PUBLICATIONS

Abud-Mendoza et al., Treating severe systemic lupus erythematosus with rituximab. An open study. Reumatol. Clin. 5(4):147-152 (2009).

(Continued)

*Primary Examiner* — Brian J Davis
(74) *Attorney, Agent, or Firm* — COOLEY LLP; Matthew Pavao; Chen Chen

(57) ABSTRACT

The present disclosure relates to crystalline polymorph forms of 6-[(3S,4S)-4-methyl-1-(pyrimidin-2-ylmethyl)pyrrolidin-3-yl]-3-tetrahydropyran-4-yl-7H-imidazol[1,5-a]pyrazin-8-one.

20 Claims, 11 Drawing Sheets

(56) References Cited

U.S. PATENT DOCUMENTS

| | | |
|---|---|---|
| 9,700,534 B2 | 7/2017 | Freeman et al. |
| 9,725,453 B2 | 8/2017 | Bursavich et al. |
| 9,771,366 B2 | 9/2017 | Dunn et al. |
| 9,850,249 B2 | 12/2017 | Svenstrup et al. |
| 10,513,524 B2 | 12/2019 | Svenstrup et al. |
| 2001/0037598 A1 | 11/2001 | Suppes et al. |
| 2002/0128510 A1 | 9/2002 | Durley et al. |
| 2003/0078299 A1 | 4/2003 | Ferrante et al. |
| 2004/0006248 A1 | 1/2004 | Paiocchi et al. |
| 2004/0020186 A1 | 2/2004 | Orlando et al. |
| 2004/0092590 A1 | 5/2004 | Arterburn et al. |
| 2004/0147599 A1 | 7/2004 | Gagnon et al. |
| 2004/0176451 A1 | 9/2004 | Tamai et al. |
| 2004/0220176 A1 | 11/2004 | Dickason et al. |
| 2004/0220186 A1 | 11/2004 | Bell et al. |
| 2004/0254240 A1 | 12/2004 | Ferrante et al. |
| 2005/0136103 A1 | 6/2005 | Ben-Sasson et al. |
| 2005/0232981 A1 | 10/2005 | Ben-Sasson |
| 2006/0018874 A1 | 1/2006 | Radhakrishnan et al. |
| 2006/0063953 A1 | 3/2006 | Maurizio et al. |
| 2006/0100278 A1 | 5/2006 | Cooper et al. |
| 2006/0241088 A1 | 10/2006 | Arterburn et al. |
| 2007/0099925 A1 | 5/2007 | Calderwood et al. |
| 2007/0232579 A1 | 10/2007 | Freeman et al. |
| 2007/0275893 A1 | 11/2007 | Quay |
| 2008/0096961 A1 | 4/2008 | Serhan et al. |
| 2008/0107729 A1 | 5/2008 | Amin et al. |
| 2008/0108697 A1 | 5/2008 | Ibrahim et al. |
| 2009/0030003 A1 | 1/2009 | Verhoest et al. |
| 2009/0074857 A1 | 3/2009 | Dror et al. |
| 2009/0220612 A1 | 9/2009 | Perera |
| 2009/0326070 A1 | 12/2009 | Freeman et al. |
| 2010/0166918 A1 | 7/2010 | Miller |
| 2010/0216884 A1 | 8/2010 | Freeman |
| 2010/0286257 A1 | 11/2010 | Perricone |
| 2010/0286271 A1 | 11/2010 | Perricone |
| 2010/0286272 A1 | 11/2010 | Perricone |
| 2010/0331268 A1 | 12/2010 | Freeman et al. |
| 2011/0082147 A1 | 4/2011 | Harbeson et al. |
| 2011/0082206 A1 | 4/2011 | Miller |
| 2011/0092594 A1 | 4/2011 | Yang |
| 2011/0196037 A1 | 8/2011 | Yang |
| 2011/0256247 A1 | 10/2011 | Miller |
| 2011/0280852 A1 | 11/2011 | Miller |
| 2011/0312909 A1 | 12/2011 | Ciomei et al. |
| 2011/0319325 A1 | 12/2011 | Miller |
| 2012/0136034 A1 | 5/2012 | Freeman et al. |
| 2012/0157458 A1 | 6/2012 | Ripka et al. |
| 2012/0295925 A1 | 11/2012 | Tung et al. |
| 2013/0005730 A1 | 1/2013 | Sun et al. |
| 2013/0039956 A1 | 2/2013 | Dietz |
| 2013/0059912 A1 | 3/2013 | Freeman |
| 2013/0101514 A1 | 4/2013 | Cushing |
| 2013/0143907 A1 | 6/2013 | Norimine et al. |
| 2013/0210917 A1 | 8/2013 | Freeman et al. |
| 2014/0024713 A1 | 1/2014 | Yang |
| 2014/0088081 A1 | 3/2014 | Claffey et al. |
| 2014/0243380 A1 | 8/2014 | Yang |
| 2014/0271844 A1 | 9/2014 | Miller |
| 2014/0308336 A1 | 10/2014 | Indolfi et al. |
| 2015/0018417 A1 | 1/2015 | Freeman et al. |
| 2015/0045348 A1 | 2/2015 | Svenstrup et al. |
| 2015/0051283 A1 | 2/2015 | Batthyany Dighiero et al. |
| 2015/0246059 A1 | 9/2015 | Freeman et al. |
| 2015/0274736 A1 | 10/2015 | Svenstrup et al. |
| 2016/0081961 A1 | 3/2016 | Cushing |
| 2016/0081962 A1 | 3/2016 | Miller et al. |
| 2016/0151318 A1 | 6/2016 | Yang |
| 2017/0081333 A1 | 3/2017 | Svenstrup et al. |
| 2017/0095437 A1 | 4/2017 | Jorkasky |
| 2017/0173018 A1 | 6/2017 | Svenstrup et al. |
| 2018/0092948 A1 | 4/2018 | Weiss et al. |
| 2018/0194770 A1 | 7/2018 | Svenstrup et al. |
| 2020/0247750 A1 | 8/2020 | Nam et al. |
| 2021/0085684 A1 | 3/2021 | Svenstrup et al. |
| 2021/0094960 A1 | 4/2021 | Svenstrup et al. |
| 2021/0107911 A1 | 4/2021 | Buttar et al. |
| 2021/0177845 A1 | 6/2021 | Calamai et al. |

FOREIGN PATENT DOCUMENTS

| | | |
|---|---|---|
| CN | 1344268 A | 4/2002 |
| CN | 101448829 A | 6/2009 |
| CN | 101557826 A | 10/2009 |
| CN | 101687876 A | 3/2010 |
| CN | 102099024 A | 6/2011 |
| CN | 102307464 A | 1/2012 |
| CN | 101687876 B | 12/2012 |
| CN | 103313988 A | 9/2013 |
| CN | 104093720 A | 10/2014 |
| CN | 104220060 A | 12/2014 |
| CN | 103313988 B | 6/2016 |
| CN | 107810187 A | 3/2018 |
| DE | 102012008730 A1 | 6/2013 |
| EP | 0911333 A1 | 4/1999 |
| EP | 1097706 A1 | 5/2001 |
| EP | 1407767 A1 | 4/2004 |
| EP | 1772149 A1 | 4/2007 |
| EP | 2123301 A1 | 11/2009 |
| EP | 2123801 A1 | 11/2009 |
| GB | 587992 A | 5/1947 |
| GB | 1407932 A | 10/1975 |
| JP | S62132804 A | 6/1987 |
| JP | 2001520189 A | 10/2001 |
| JP | 2003509485 A | 3/2003 |
| JP | 2004509097 A | 3/2004 |
| JP | 2008520739 A | 6/2008 |
| JP | 2011525525 A | 9/2011 |
| JP | 2014015477 A | 1/2014 |
| WO | WO-9809621 A1 | 3/1998 |
| WO | WO-9924433 A1 | 5/1999 |
| WO | WO-0106983 A2 | 2/2001 |
| WO | WO-0121575 A1 | 3/2001 |
| WO | WO-0160778 A2 | 8/2001 |
| WO | WO-0178654 A2 | 10/2001 |
| WO | WO-0178719 A1 | 10/2001 |
| WO | WO-0179156 A1 | 10/2001 |
| WO | WO-0115673 A3 | 3/2002 |
| WO | WO-0222559 A2 | 3/2002 |
| WO | WO-02102364 A1 | 12/2002 |
| WO | WO-03031399 A1 | 4/2003 |
| WO | WO-03037432 A1 | 5/2003 |
| WO | WO-03037899 A1 | 5/2003 |
| WO | WO-03039533 A1 | 5/2003 |
| WO | WO-03093270 A1 | 11/2003 |
| WO | WO-2004096811 A1 | 11/2004 |
| WO | WO-2005041972 A1 | 5/2005 |
| WO | WO-2005073164 A1 | 8/2005 |
| WO | WO-2005110396 A2 | 11/2005 |
| WO | WO-2006055965 A2 | 5/2006 |
| WO | WO-2006086727 A2 | 8/2006 |
| WO | WO-2007137819 A1 | 12/2007 |
| WO | WO-2007140433 A2 | 12/2007 |
| WO | WO-2008008767 A2 | 1/2008 |
| WO | WO-2008011085 A1 | 1/2008 |
| WO | WO-2008103753 A2 | 8/2008 |
| WO | WO-2008139293 A1 | 11/2008 |
| WO | WO-2009017802 A1 | 2/2009 |
| WO | WO-2009038671 A2 | 3/2009 |
| WO | WO-2009113696 A1 | 9/2009 |
| WO | WO-2009129495 A1 | 10/2009 |
| WO | WO-2009134383 A2 | 11/2009 |
| WO | WO-2009149496 A1 | 12/2009 |
| WO | WO-2009155439 A2 | 12/2009 |
| WO | WO-2010012777 A1 | 2/2010 |
| WO | WO-2010042877 A1 | 4/2010 |
| WO | WO-2010078504 A1 | 7/2010 |
| WO | WO-2010084438 A1 | 7/2010 |
| WO | WO-2010129763 A1 | 11/2010 |
| WO | WO-2010129777 A1 | 11/2010 |
| WO | WO-2011011882 A1 | 2/2011 |
| WO | WO-2011014261 A1 | 2/2011 |
| WO | WO-2011028820 A1 | 3/2011 |
| WO | WO-2011030351 A2 | 3/2011 |

(56) References Cited

FOREIGN PATENT DOCUMENTS

| WO | WO-2011041639 A2 | 4/2011 |
|---|---|---|
| WO | WO-2011056126 A1 | 5/2011 |
| WO | WO-2011098746 A1 | 8/2011 |
| WO | WO-2012040230 A1 | 3/2012 |
| WO | WO-2012110441 A1 | 8/2012 |
| WO | WO-2013053690 A1 | 4/2013 |
| WO | WO-2013110768 A1 | 8/2013 |
| WO | WO-2013116765 A1 | 8/2013 |
| WO | WO-2013170069 A1 | 11/2013 |
| WO | WO-2014036555 A1 | 3/2014 |
| WO | WO-2015023557 A1 | 2/2015 |
| WO | WO-2015073527 A1 | 5/2015 |
| WO | WO-2015185499 A1 | 12/2015 |
| WO | WO-2017005786 A1 | 1/2017 |
| WO | WO-2018009424 A1 | 1/2018 |
| WO | WO-2018218104 A1 | 11/2018 |
| WO | WO-2019226944 A1 | 11/2019 |
| WO | WO-2020047311 A1 | 3/2020 |
| WO | WO-2020206336 A1 | 10/2020 |
| WO | WO-2020227399 A1 | 11/2020 |

OTHER PUBLICATIONS

Adjei et al., A phase I trial of the farnesyl transferase inhibitor SCH66336: evidence for biological and clinical activity. Cancer Res. 60:1871-1877 (2000).
Akaike et al., Antagonistic action of imidazolineoxyl N-oxides against endothelium-derived relaxing factor/NO through a radical reaction. Biochem. 32:827-832 (1993).
Akinsheye et al., Fetal hemoglobin in sickle cell anemia. Blood 118(1):19-27 (2011).
Alber, Signaling mechanisms of the mycobacterium tuberculosis receptor Ser/Tur protein kinases. Curr. Opin. Struct. Biol. 19(6):650-657 (2009).
Almeida et al., High expression of the cGMP-specific phosphodiesterase, PDE9A, in sickle cell disease (SCD) and the effects of its inhibition in erythroid cells and SCD neutrophils. British Journal of Haematology 142(5):836-44 (2008).
Almeida et al.: Hydroxyurea and a cGMP-amplifying agent have immediate benefits on acute vaso-occlusive events in sickle cell disease mice. Blood. 120(14):2879-2888 (2012).
Alsultan et al., Genetic studies of fetal hemoglobin in the Arab-Indian haplotype sickle cell-β(0) thalassemia. American Journal of Hematology 88(6):531-532 (2013).
Altschul et al., Gapped BLAST and PSI-BLAST: a new generation of protein database search programs. Nucleic Acids Res. 25(17) 3389-3402 (1997).
Anand et al., Synthesis and evaluation of small libraries of triazolylmethoxy chalcones, flavanones and 2-aminopyrimidines as inhibitors of mycobacterial FAS-II and PknG. Biorganic & Medicinal Chem. 20(17):5150-5183 (2012).
Arbeeny, C. et al., Renoprotection by treatment with CXA-10, an Endogenous Nitro Fatty Acid. Poster, Nov. 5, 2015, 1 page (2015).
Arbeeny, C. et al., Renoprotection by treatment with CXA10, an endogenous nitro-fatty Acid. J. Am. Soc. Nephrol. 26:126A, Abstract THP0158 (2015).
Arnold et al., Nitric oxide activates guanylate cyclase and increases guanosine 3':5'-cyclic monophosphate levels in various tissue preparations. Proc. Natl. Acad. Sci. 74:3203-3207 (1977).
Artim et al., Nitro-oleic acid targets transient receptor potential (TRP) channels in capsaicin sensitive afferent nerves of rat urinary bladder. Expt. Neural. 232:90-99 (2011).
Asakura et al., Synthesis and biological evaluation of y-fluoro-,y-unsaturated acids. J of Flourine Chem. 127:800-808 (2006).
Aunapuu et al., Morphological changes in experimental postischemic rat kidney. A pilot study. Ann. Anat. 187(1):63-70 (2005).
Baker et al., Convergence of nitric oxide and lipid signaling: Anti-inflammatory nitro-fatty acids. Free Radic. Biol. Med. 46:989-1003. (2009).

Baker et al., Fatty acid transduction of nitric oxide Signaling. J Biol. Chem. 280(51):42464-42475 (2005).
Baker et al., Nitro-fatty acid reaction with glutathione and cysteine; kinetic analysis of thiol alkylation by a Michael addition reaction. J of Biol. Chem. 282(42):31085-31093 (2007).
Baker et al., Red cell membrane and plasma linoleic acid nitration products: Synthesis, clinical identification, and quantitation. Proc. Natl. Acad. Sci. 101(32):11577-11582 (2004).
Balazy et al., Vicinal nitrohydroxyeicosatrienoic acids: vasodilator lipids formed by reaction of nitrogen dioxide with arachidonic acid. J Pharmacol. Ex Ther. 299(2):611-619 (2001).
Balazy, Isomerization and Nitration of arachidonic acid by nitrogen dioxide. Advances in Mass Spectrometry 15:375-376 (2001).
Baldus et al., Endothelial transcytosis of myeloperoxidase confers specificity to vascular ECM proteins as targets of tyrosine nitration. J Clin. Invest. 108(12):1759-1770 (2001).
Baldus et al., Is NO news bad news in acute respiratory distress syndrome. Am. J Respir. Crit. Care Med. 163:308-310 (2001).
Ballini et al., Fast diastereoselective Baylis-Hillman reaction by nitroalkenes: synthesis of di-and triene derivatives. Tetrahedron 60:4995-4999 (2004).
Ballini et al., Nitroalkanes and ethyl glyoxalate as common precursors for the preparation of both 13-keto esters and a, 13-unsaturated esters. Tetrahedron Letters 45:7027-7029 (2004).
Ballini et al., (Z)-7-nitro-3-heptene as central intermediate for the synthesis of jasmone, methyl jasmonate and y-jasmolactone. Synthetic Communications 19(3-4):575-583 (1989).
Bates et al., Nitroalkene fatty acids mediate activation of Nrf2/ARE-dependent and PPARy-dependent transcription by distinct signaling pathways and with significantly different potencies. Biochem. 50:7765-7773 (2011).
Bates et al., Noncatalytic interactions between glutathione s-transferases and nitroalkene fatty acids modulate nitroalkene-mediated activation of peroxisomal proliferator-activated receptory. Biochem. 48:4159-4169 (2009).
Batthyany et al., Reversible post-translational modification of proteins by nitrated fatty acids in vivo. J Biol. Chem. 281(29):20450-20463 (2006).
Baumer Iodostarin 'Roche' in the treatment of syphilis. Deutsche Medizinische Wochenschrifr 39:1361 (case abstract) (1 page) (1913).
Beckman et al., Apparent hydroxyl radical production by peroxynitrite: implications for endothelial injury from nitric oxide and superoxide. Proc. Natl. Acad. Sci. 87:1620-1624 (1990).
Bell-Parikh et al., Biosynthesis of 15-deoxy-A12 14-PGJ2 and the ligation of PPARy. J Clin. Invest. 112(6):945-955 (2003).
Bennett et al., Cecil Textbook of Medicine 1996, 20th Ed., 1, 1004-1010 (1996).
Berge, S.M. et al., (1977) "Pharmaceuticals Salts", J. Pharma. Sci. 66: 1-19.
Bervejillo et al., Estudio del potencial anti-aterogenico del AANO2 in vivo. Tesina del grado de la Licenciatura en Bioquiica, Facultad de Ciencias, UdelR Feb. 2012, 5-6, Fig. 2 (in Spanish with English summary) (2012).
Biegert et al., Sequence context-specific profiles for homology searching. PNAS 106(10):3770-3775. (2009).
Bjorn, Clues emerge about benefits of briefly blocking blood flow. Nature 15(2):132 (2009).
Blair et al., Bathophenanthrolinedisulphonic acid and bathocuproinedisulphonic acid, water soluble reagents for iron and copper. Talanta 7(3-4):163-174 (abstract) (1961).
Blakemore, The modified Julia olefination: alkene synthesis via the condensation of metallated heteroarylalkylsulfones with carbonyl compounds. J Chem. Soc. Perkin Trans. I. 23:2563-2585 (2002).
Blanco et al., 6-Methylnitroarachidonate: A novel esterified nitroalkene that potently inhibits platelet aggregation and exerts cGMP-mediated vascular relaxation. Free Radic. Biol. Med. 50:411-418 (2011).
Bligh et al., A rapid method of total lipid extraction and purification. Can. J Biochem. Physiol. 37(8):911-917 (1959).
Blockland, A. et al., (2006) "Improving Memory: A Role for Phosphodiesterases", Curr. Pharm. Des. 12(20):2511-2523.

(56) References Cited

OTHER PUBLICATIONS

Bloodsworth et al., Nitric oxide regulation of free radical- and enzyme-medicated lipid and lipoprotein oxidation. Arterioscler Thromb. Vasc. Biol. 20:1707-1715 (2000).
Boden et al., Free fatty acids in obesity and type 2 diabetes: defining their role in the development of insulin resistance and -cell dysfunction. Euro. J Clin. Invest. 32(Suppl. 3): 14-23 (2002).
Bonacci et al., Electrophilic fatty acids regulate matrix metalloproteinase activity and expression. J Biolo. Chem. 286(18):16074-16081 (abstract) (2011).
Bonacci et al., Gas-phase fragmentation analysis of nitro-fatty acids. J Am. Soc. Mass Spec. 22:1534-1551 (2011).
Bonacci et al., Nitro-oleic acid improves insulin signaling via protein tyrosine phosphatase-lb inhibition. Free Radical Bio. Med. Elsevier Science, 45(Suppl. 1):SI54 (abstract) (2008).
Bonomi et al., Direct metal ion substitution at the [M(Scys)4] 2 site of rubredoxin. J Biol. Inorg. Chem. 3(6):595-605 (1998).
Borniquel et al., Nitrated oleic acid up-regulates PPARy and attenuates experimental inflammatory bowel disease. Free Radic. Bio. Med. 49(4):499-505 (2010).
Boruwa et al., Catalytic asymmetric henry reaction. Tetrahedron: Asymmetry Report No. 90(17):3315-3326 (2006).
Breer, H. et al., (1990) "Rapid Kinetics of Second Messenger Formation in Olfactory Transduction" Nature 345 :6270):65-68.
Burdge, a-Linolenic acid metabolism in men and women: nutritional and biological ilmplications. Clin. Nutri. Metabol. Care 7:137-144 (2004).
Cannon, Burger's Medicinal Chemistry and Drug Discovery 1995, Fifth Edition, I: Principles and Practice, Chap. 19, John Wiley & Sons, Inc., 783-802 (1995).
Castro et al., Cytochrome c: a catalyst and target of nitrate-hydrogen peroxide-dependent protein nitration. Arch. Biochem. Biophys. 421:99-107 (2004).
Chawla, et al. Current Research & Information on Pharmaceutical Sciences (CRIPS), 5(1), 2004, 9-12.
Chawla et al., PPAR-y dependent and independent effects on macrophage-gene expression in lipid metabolism and inflammation. Nat. Med. 7(1):48-52 (2001).
Chen et al., Peroxisome proliferator-activated receptors and the cardiovascular system. Vitam. Harm. 66:157-188 (2003).
Chen et al., Synthesis and screening of novel vitamin E derivatives for anticancer functions. European J of Medicinal Chem. 58:72-83 (2012).
Chen et al., Troglitazone inhibits atherhosclerosis in apolipoprotein E-knockout mice: pleiotropic effects on CD36 expression and HDL. Arterioscler Thromb. Vasc. Biol. 21:372-377 (2001).
Chieffo, C. et al., Use of an obese population in phase I to evaluate the pharmacology of oral CXA-10, an endogenous nitro-fatty acid signaling agent. Poster, 4 pages (Sep. 26, 2016).
Christiansen, T. et al., Monocyte chemoattractant protein-1 is produced in isolated adipocytes, associated with adiposity and reduced after weight loss in morbid obese subjects. International Journal of Obesity 29:146-150 (2005).
Ückert [Ueckert] et al., Phosphodiesterase inhibitors in clinical urology. Expert Review in Clinical Pharmacology 6(3):323-332 (2013).
Ückert [Ueckert], S. et al., "Phosphodiesterase (PDE) inhibitors in the treatment of lower urinary tract dysfunction" (2011) Br. J. Clin. Pharmacol 72(2): 197-204.
Clapp et al., Oxygenation of monounsaturated fatty acids by soybean liposygenase-1: evidence for transient hydroperoxide formation. Biochem. 45:15884-15892 (2006).
Claudel et al., Reduction of atherosclerosis in apolipoprotein E knockout mice by activation of the retinoid X receptor. Proc. Natl. Acad. Sci. 98(5):2610-2615 (2001).
Coffey et al., Catalytic consumption of nitric oxide by 12/15-lipoxygenase: Inhibition of monocyte soluble guanylate cyclase activation. Proc. Natl. Acad. Sci. 98(14):8006-8011 (2001).
Cole et al., Deciphering the biology of mycobacterium tuberculosis from the complete genome sequence. Nature 393:537-544 (1998).
Cole et al., Nitro-fatty acid inhibition of neointima formation after endoluminal vessel injury. Circ. Res. Nov. 6, 2009, 1-8; Suppl. Materials 1-6. (2009).
Coles et al., Nitrolinoleate inhibits platelet activation by attenuating calcium mobilization and inducing phosphorylation of vasodilator-stimulated phosphoprotein through elevation of cAMP. J Biol. Chem. 277(8):5832-5840 (2002).
Coles et al., Nitrolinoleate inhibits superoxide generation, degranulation, and integrin expression by human neutrophils. Novel antiinflammatory properties of nitric oxide-derived reactive species in vascular cells. Circ. Res. 91:375-381 (2002).
Collins et al., Troglitazone inhibits formation of early atherosclerotic lesions in diabetic and nondiabetic low density lipoprotein receptor-deficient mice. Arterioscler Thromb. Vasc. Biol. 21:365-371 (2001).
Conran, N. "Prospects for early investigational therapies for sickle cell disease" (2015) Expert Opin. Investig. Drugs 24(5):595-602.
Cooke, S.F. et al., (2006) "Plasticity in the Human Central Nervous System" Brain 129(7):1659-1673.
Cosby et al., Nitrite reduction to nitric oxide by deoxyhemoglobin vasodilates the human circulation. Nat. Med. 9(12):1498-1505 (2003).
Cowley et al., The mycobacterium tuberculosis protein serine/threonine kinase PknG is linked to cellular glutamate/glutamine levels and is important for growth in vivo. Molecular Microbio. 52(6):1691-1702 (2004).
Cui et al., Nitrated fatty acids: endogenous anti-inflammatory signaling mediators. J Biol. Chem. 281(47):35686-35698 (2006).
Da Silva et al., Phosphodiesterase-9 (PDE9) inhibition with BAY 73-6691 increases corpus cavernosum relaxations mediated by nitric oxide-cyclic GMP pathway in mice. International Journal of Impotence Research 25(2):69-73 (2013).
Dang et al. (Hung), Anti-inflammatory constituents of the red alga gracilaria verrucosa and their synthetic analogues. J Nat. Prod. 71(2):232-240 (2008).
Dangi et al., Biogenic synthesis, purification, and chemical characterization of anti-inflammatory resolvins derived from docosapentaenoic acid (DPAn-6). J Biol. Chem. 284(22): 14744-14759 (2009).
Davies et al., Oxidized alkyl phospholipids are specific, high affinity peroxisome proliferator-activated receptor y ligands and agonists. J Biol. Chem. 276(19):16015-16023 (2001).
De Meijere et al., Metal-catalyzed cross-coupling reactions. VViley-VCH Verlag GMBH & Co. 2004, Weinheim, vols. 1 and 2, XXII, ISBN-10: 3-527-30518-1 and ISBN-13: 978-3-527-30518-6 (TOC) (2004).
Defronzo et al., Insulin resistance: a multifaceted syndrome responsible for NIDDM, obesity, hypertension, dyslipidemia, and atherosclerotic cardiovascular disease. Diabetes Care 14(3):175-194 (1991).
Del Mar Grasa et al., Daily oral oleoyl-estrone gavage induces a dose-dependent loss of fat in Wistar rats. Obesity Res. 9(3):202-209 (2001).
Delerive et al., Oxidized phospholipids activated PPARa in a phospholipase A2-dependent manner. FEES Lett. 471:34-38 (2000).
Dembitsky et al., Natural halogenated fatty acids: their analogues and derivatives. Progress in Lipid Research 41(4):315-367 (2002).
Denicola et al., Diffusion of nitric oxide into low density lipoprotein. J Biol. Chem. 277(2):932- 936 (2002).
Denicola et al., Diffusion of peroxynitrite across erythrocyte membranes. Proc. Natl. Acad. Sci. 95:3566-3571 (1998).
Desper et al., Getting a tree fast: neighbor joining, FastME, and distance-based methods. Curr. Protoc. Bioinformatics, Chap. 6, Unit 6.3 (2006).
Diabetic ketoacidosis in www.mayoclinic.org/diseases-conditions/diabetic-ketoacidosis/basics/treatment/con-20026470 (retrieved from the internet Jan. 21, 2016).
D'Ischia et al., Medium-dependent competitive pathways in the reactions of polyunsaturated fatty acids with nitric oxide in the presence of oxygen. Structural characterisation of nitration products and a theoretical insight. Tetrahedron 55:9297-9308 (1999).
D'Ischia, Oxygen-dependent nitration of ethyl linoleate with nitric oxide. Tetrahedron Lett. 37(32):5773-5774 (1996).

(56) References Cited

OTHER PUBLICATIONS

Dodge et al., Composition of phospholipids and of phospholipids fatty acids and aldehydes in human red cells. J Lipid Res. 8:667-675 (1967).
Doksorubitsin-Ebeve, Instruksiya po primeneniyu lekarstvennogo perparata dlya meditinskogo primeneniya, Retrieved from the Internet: Nov. 19, 2014, http://medi.ru/doc/f4509.htm.
Dorwald, Side Reactions in Organic Synthesis. Wiley-VCH, 1-16 (2005).
Duan et al., Nephrotoxicity of high- and low-osmolar contrast media: Protective role of forsinopril or telmisartan in a rat model. J Central S. Univ. 32(5):812-818 (2007).
Duncton, M.A.J. et al. (2008) "Preparation of Aryloxetances and Arylazetidines by Use of an Alkyl-Aryl Suzuki Coupling" Organic Letters 10(15):3259-3262.
Eardley, K.S. et al., The relationship between albuminuria, MCP-1/CCL2, and interstitial macrophages in chronic kidney disease. Kidney Int. 69:1189-1197 (2006).
Easton et al., Polyunsaturated nitroalkanes and nitro-substituted fatty acides. Synthesis 3:451-457 (2001).
Eberhardt et al., Prevalence of overweight and obesity among adults with Diagnosed Diabetes —United States, 1988-1994 and 1999-2002. CDC, Nov. 19, 2004; 53(45):1066-1068 (2004).
Eiserich et al., Myeloperoxidase, a leukocyte-derived vascular NO oxidase. Sci. 296:2391-2394 (2002).
Eiserich et al., Pathophysiology of nitric oxide and related species: free radical reactions and modification of biomolecules. Malec. Aspects Med. 19:221-357 (1998).
Escudier et al., Bevacizumab plus interferon alfa-2a for treatment of metastatic renal cell carcinoma: a randomized, double-blind phase III trial. The Lancet 370:2103-2111 (2007).
Eurasian Patent Application No. 202190460 Office Action.
Evans et al., PPARs and the complex journey to obesity. Nat. Med. 10(4):1-7 (2004).
Ex Parte Sauerberg, Appeal 2015-007064, Decided Jan. 12, 2017.
Extended European Search Report dated Oct. 25, 2016 in Application No. 16185105.0, entitled PDE9I With Imidazo Pyrazinone Backbone.
Extended European Search Report dated Mar. 10, 2017 in European Application No. 17152165.1, entitled "PDE9I With Imidazo Triazinone Backbone".
Fazzari, M. et al., Generation and esterification of electrophilic fatty acid nitroalkenes in triacylglycerides. Free Radical Biology and Medicine 87:113-124 (2015).
Feelisch et al., Concomitant S-, N-, and heme-nitros(yl)ation in biological tissues and fluids: implications for the fate of NO in vivo. FASEB J 16:1775-1785 (2002).
Ferreira et al., Macrophage activation induces formation of the anti-inflammatory lipid cholesteryl-nitrolinoleate. Biochem. J. 417:223-234 (2009).
Ferry et al., Binding of prostaglandins to human PPARy: tool assessment and new natural ligands. Eur. J Pharmacol. 417:77-89 (2001).
Final Office Action for U.S. Appl. No. 14/962,170, dated Nov. 1, 2017, 8 Pages.
Finlayson-Pitts et al., A Fourier transform infrared spectrometry study of the reactions of phosphatidylcholines with gaseous N2 O5 and NO2. Toxicol. Appl. Pharmacol. 89:438-448 (1987).
Fisher, D.A. et al., (1998) "Isolation and Characterization of PDE9A, a Novel Human cGMP- specific Phosphodiesterase" J_Boil_Chem_ 273(25):15559-15564.
Fiuza et al., From the characterization of the four serine/threonine protein kinases (PknA/B/G/L) of corynebacterium glutamicum toward the role of PknA and PknB in cell division. J Biol. Chem. 283(26):18099-18112 (2008).
Forman et al., 15-Deoxy-A 12 14-prostaglandin J2 is a ligand for the adipocyte determination factory PPAR gamma. Cell 83:803-812 (1995).
Freeman et al., Nitro-fatty acid formation and signaling. J of Biol. Chem. 283(23): 15515-15519 (2008).

Freshney, Culture of Animal Cells. A Manual a/Basic Technique 1983, Alan R. Liss, Inc., New York, 1-6 (1983).
Fu et al., Oleylethanolamide regulates feeding and body weight through activation of the nuclear receptor PPAR-a. Nature 425:90-93 (2003).
Furstner et al., Total synthesis of epohelmin b and its analogues. Chem. Asian J 3:310-318 (2008).
Galle et al., Pulmonary hypertension and pulmonary arterial hypertension: a clarification is needed. Eur Respir J. 36(5):986-990 (2010).
Gallon et al., The identification of the allylic nitrite and nitro derivatives of methyl linoleate and methyl linolenate by negative chemical ionization mass spectroscopy. Lipids 28(2):125-133 (1993).
Gallon et al., The reaction of low levels of nitrogen dioxide with methyl linoleate in the presence and absence of oxygen. Lipids 29(3):171-176 (1994).
Garde, I., Complexa, Inc. Completes $13 Million Series B Financing to Further Advance Clinical Development of CXA-10. FierceBiotech, Jun. 4, 2014, pp. 1-2 (2014).
Gavin III et al., Reducing cardiovascular disease risk in patients with type 2 diabetes: a message from the National Diabetes Education Program. Am. Fam. Physician 68(8):1569-15674 (2003).
Geiger, S.S. et al., Chrono-immunology: progress and challenges in understanding links between the circadian and immune systems. Immunology 146(3):349-358 (2015).
Genders et al., cGMP phosphodiesterase inhibition improves the vascular and metabolic actions of insulin in skeletal muscle. Am J Physiol Endocrinol Metab. 301(2):E342-E350 (2011).
Gladwin et al., Role of circulating nitrite and S-nitrosohemoglobin in the regulation of regional blood flow in humans. Proc. Natl. Acad. Sci. 97(21):11482-11487 (2000).
Gladwin et al., S-nitrosohemoglobin is unstable in the reductive erythrocyte environment and lacks O2/NO-linked allosteric function. J Biol. Chem. 277(31):27818-27828 (2002).
Gladwin et al., The emerging biology of the nitrite anion. Nat. Chem. Biol. 1(6):308-314 (2005).
Glauser et al., The inflammatory response and tissue damage. The example of renal scars following acute renal infection. Pediatric Nephrology 1(4):615-622 (Abstract from PubMed website Jan. 22, 2016) (1987).
Goodman & Gilman's The Pharmacological Basis a/Therapeutics, Ninth Edition 1996, McGraw-Hill Book Company, New York, Appendix II, 1707-1711 (TOC) (1996).
Goodman & Gilman's The Pharmacological Basis a/Therapeutics, Sixth Edition 1980, MacMillan Publishing Co., New York (TOC) (1980).
Goodman & Gilman's The Pharmacological Basis a/Therapeutics, Tenth Edition 2001, McGraw-Hill Book Company, New York (TOC) (2001).
Gorczynski et al., Evaluation of nitroalkenes as nitric oxide donors. Bioorg. Med. Chem. Lett. 17:2013-2017 (2007).
Gorczynski et al., Regio-and stereospecific synthesis and nitric oxide donor properties of (E)-9- and (E)-10-nitrooctadec-9-enoic acids. Org. Lett. 8(11):2305-2308 (2006).
Gregory et al., 5-HT3 Receptor antagonists for the prevention of chemotherapy-induced nausea and vomiting: a comparison of their pharmacology and clinical efficacy. Drugs 55(2):173-189 (1998).
Grisham, Myoglobin-catalyzed hydrogen peroxide dependent arachidonic acid peroxidation. Free Radic. Biol. Med. 1:227-232 (1985).
Groeger et al., Cyclooxygenase-2 generates anti-inflammatory mediators from omega-3 fatty acids. Nat. Chem. Bio. 6:433-441 (2010).
Groeger et al., Discovery, structural characterization and quantification of novel inflammatory-induced electrophilic fatty acid derivatives. Free Radical Bio. & Med. 45(1):S134 (2008).
Groeger et al., Signaling actions of electrophiles: anti-inflammatory therapeutic candidates. Malec. Interven. 10(1):39-50 (2010).
Guindon et al., A simple, fast, and accurate algorithm to estimate large phylogenies by maximum likelihood. Systematic Bio. 52(5):696-704 (2003).
Guindon et al., Estimating maximum likelihood phylogenies with PhyML. Methods in Molecular Bio. 537:113-137 (2009).

(56) References Cited

OTHER PUBLICATIONS

Guo et al., Atypical PKCI transduces electrophilic fatty acid signaling in pulmonary epithelial cells. Nitric Oxide 25:366-372 (2011).
Gutierrez et al., Nitric oxide regulation of superoxide-dependent lung Injury: oxidant- protective actions of endogenously produced and exogenously administered nitric oxide. Free Radic. Biol. Med. 21(1):43-52 (1996).
Hackam, et al., Translation of Research Evidence From Animals to Humans;JAMA, 296(14), 2006, 1731-1732.
Hartmann et al., A randomized trial comparing the nephrotoxicity of cisplatin/ifosfamide-based combination chemotherapy with or without amifostine in patients with solid tumors. Investigational New Drugs 18:281-289 (2000).
Hogg et al., Inhibition of low-density lipoprotein oxidation by nitric oxide potential role in atherogenesis. FEBS Lett. 334(2):170-174 (1993).
Hogg et al., Reactions of nitric oxide with nitronyl nitroxides and oxygen: prediction of nitrate formation by kinetic simulation. Free Radic. Res. 22(1):47-56 (1995).
Hogg, The biochemistry and physiology of S-nitrosothiols. Annu. Rev. Pharmacol. Toxicol. 42:585-600 (2002).
Ichikawa et al., Nitroalkenes suppress lipopolysaccharide-induced signal transducer and activator of transcription signaling in macrophages: a critical role of mitogen-activated protein kinase phosphatase 1. Endocrinology 149(8):4086-4094 (2008).
Ignarro et al., Endothelium-derived relaxing factor from pulmonary artery and vein possesses pharmacologic and chemical properties identical to those of nitric oxide radical. Circ. Res. 61:866-879 (1987).
Ignarro et al., Pharmacological evidence that endothelium-derived relaxing factor is nitric oxide: use of pyrogallol and superoxide dismutase to study endothelium-dependent and nitric oxide-elicited vascular smooth muscle relaxation. J Pharmacol. Exp. Ther. 244(1):181-189 (1988).
Iles et al., Fatty acid transduction of nitric oxide signaling: nitrolinoleic acid mediates protective effects through regulation of the ERK pathway. Free Radic. Biol. Med. 46:866-875 (2009).
International Application No. PCT/US2017/040160 International Search Report and Written Opinion dated Oct. 9, 2017.
International Preliminary Report on Patentability for PCT/US2009/0047825 dated Jan. 6, 2011.
International Preliminary Report on Patentability issued in corresponding PCT/US2012/051304, 1-8 (dated Mar. 6, 2014).
International Preliminary Report on Patentability issued in corresponding PCT/US2012/059722, 1-9 (dated Apr. 24, 2014).
International Search Report and Written Opinion dated Dec. 4, 2009, in corresponding PCT/US2009/002628.
International Search Report and Written Opinion dated Apr. 21, 2015 corresponding to PCT/US2014/065203.
International Search Report and Written Opinion dated Aug. 19, 2013 corresponding to PCT/US2012/059722.
International Search Report and Written Opinion dated Jul. 13, 2011 corresponding to PCT/US2010/051059.
International Search Report and Written Opinion dated Jun. 2, 2013 corresponding to PCT/US2013/024476.
International Search Report and Written Opinion dated Jun. 30, 2009 corresponding to PCT/US2009/041018.
International Search Report and Written Opinion dated Mar. 23, 2012 corresponding to PCT/US2011/04201.
International Search Report and Written Opinion dated Mar. 5, 2010 corresponding to PCT/US2009/047825.
International Search Report and Written Opinion dated Nov. 1, 2012 corresponding to PCT/US2012/051304.
International Search Report and Written Opinion dated Nov. 27, 2014 corresponding to PCT/US2014/047073.
International Search Report and Written Opinion dated Oct. 12, 2006 corresponding to International Patent Application No. PCT/US2005/014305.
International Search Report and Written Opinion dated Oct. 24, 2008 corresponding to International Patent Application No. PCT/US2008/009274.
International Search Report PCT/US2010/002141 dated Nov. 24, 2010.
Itoh et al., Synthesis of docosahexaenoic acid derivatives designed as novel PPARy agonists and antidiabetic agents. Bioorg.Med. Chem. 14:98-108 (2006).
Janero et al., Differential nitros(yl)ation of blood and tissue constituents during glycerol trinitrate biotransformation in vivo. PNAS 101(48):16958-16963 (2004).
Jasuja et al.: PDE-9 Inhibition Combined with Hydroxyurea Is Beneficial in Vaso-Occlusive Crisis in Mouse Model of Sickle Cell Disease. The American Society of Hematology; 124(21):2694 (2014).
Jeong et al., Fenofibrate prevents obesity and hypertriglyceridemia in low-density lipoprotein receptor-null mice. Metabolism 53(5):607-613 (2004).
Jimenez-Estrada et al., Allyic nitration of 3-sitosterol and cholesterol acetate: preparation of 7-nitro derivatives. Steroid 62:500-503 (1997).
Jordan, V. C., "Tamoxifen: a most unlikely pioneering medicine" Nature Reviews: Drug Discovery, 2, 2003, 205.
Jourd'Heuil et al., The oxidative and nitrosative chemistry of the nitric oxide/superoxide reaction in the presence of bicarbonate. Arch. Biochem. Biophys. 365(1):92-100 (1999).
Junping et al., Pharmacokinetics and antitumor effects of vincristine carried microemulsions composed of PEG-lipid, oleic acid, vitamin E and cholesterol. Int. J Pharm. 251(1-2):13-21, Abstract (2003).
Kalliokoski, A. et al., Impact of OATP transporters on pharmacokinetics. British Journal of Pharmacology 158(3):693-705 (2009).
Kansanen et al., Nrf2-dependent and -independent responses to nitro-fatty acids in human endothelial cells: identification of heat shock response as the major pathway activated by nitro-oleic acid. J Biol. Chem. 284(48):33233-33241 [1-34] (2009).
Karp et al., Clinical and biologic activity of the farnesyltransferase inhibitor RI 15777 in adults with refractory and relapsed acute leukemias: a phase 1 clinical-laboratory correlative trial. Blood 97(11):3361-3369 (2001).
Katoh et al., Recent developments in the MAFFT multiple sequence alignment program. Briefings in Bioinformatics 9(4):286-298 (2008).
Kelley et al.: Fatty acid nitroalkenes ameliorate glucose intolerance and pulmonary hypertension in high-fat diet-induced obesity. Cardiovascular Research. 101(3):352-363 (2014).
Kelley et al., Nitro-oleic acid, a novel and irreversible inhibitor of xanthine oxidoreductase. J Biol. Chem. 283(52):36176-36184 (2008).
Khoo et al., Activation of vascular endothelial nitric oxide synthase and heme oxygenase-1 expression by electrophilic nitro-fatty acids. Free Radic. Bio. Med. 48:230-239 (2010).
Khoo et al., Electrophilic nitro-fatty acids: anti-inflammatory mediators in the vascular compartment. Curr. Opn. Pharml. 10:179-184 (2010).
Kim et al., Bisubstrate ketone analogues as serotonin N-acetyltransferase inhibitors. J Med. Chem. 44(15):2479-2485 (2001).
Kim et al., The effect of PPAR-y agonist on glucose metabolism and insulin sensitivity in non- obese type 2 diabetic rat models. Diabetes Jun. 1, 2006, American Diabetes Association 55: Suppl. 1:A483 (2006).
Kissner et al., Formation and properties of peroxynitrite as studied by laser flash photolysis, high-pressure stopped-flow technique, and pulse radiolysis. Chem. Res. Toxicol. 10:1285-1292 (1997).
Kliewer et al. A prostaglandin J2 metabolite binds peroxisome proliferatory-activated receptor y and promotes adipocyte differentiation. Cell 83:813-819 (1995).
Kliewer et al., Fatty acids and eicosanoids regulate gene expression through direct interactions and peroxisome proliferator-activated receptors a and y Proc. Natl. Acad. Sci. 94:4318-4323 (1997).
Klinke et al.: Protective Effects of 10-nitro-oleic Acid in Hypoxia-Induced Murine Model of Pulmonary Hypertension. American Journal of Respiratory Dell and Molecular Biology. 51(1):155-162 (2014).
Kobayshi, The reaction of nitrogen dioxide with lung surface components: the reaction with cis-9-octadecenoic acid. Chemosphere 12(9/10):1317-1325 (1983).

(56) References Cited

OTHER PUBLICATIONS

Koenitzer et al., Redox signaling in inflammation: interactions of endogenous electrophiles and mitochondria in cardiovascular disease. Ann. NY Acad. Sci. 1203:45-52 (2010).
Konig, J. et al., Transporters and drug-drug interactions: important determinants of drug disposition and effects. Pharmacological Review 65(3):944-66 (2013).
Kunin, Urinary tract infections in females. Clinical Infectious Diseases 18:1-10 (1994).
Lai et al., Reactions of dinitrogen pentoxide and nitrogen dioxide with 1-palmitoyl-2-oleoyl-sn-glycero-3-phosphocholine. Lipids 26(4):306-314. Abstract (1991).
Larfars et al., Activation of nitric oxide release and oxidative metabolism by leukotrienes B4, C4, and D4 in human polymorphonuclear leukocytes. Blood 93(4):1399-1405 (1999).
Lee et al., Peroxisome proliferators-activated receptor-y in macrophage lipid homeostasis. Trends Endocrinol. Metab. 13(8):331-335 (2002).
Lee et al., Rosiglitazone ameliorates cisplatin-induced renal injury in mice. Nephrol. Dial. Transplant. 21:2096-2105 (2006).
Levy et al., Lipid mediator class switching during acute inflammation: signals in resolution. Nat. Immunol. 2(7):612-619 (2001).
Li et al., Differential inhibition of macrophage foam-cell formation and atherosclerosis in mice by PPAR alpha, betta/delta, and gamma. J Clin. Invest. 114(11):1564-1576 (2004).
Li et al., Molecular recognition of nitrated fatty acids by PPAR gamma. Nat. Struct. Mol. Biol. 15(8):865-867 [1-3] (2008).
Li et al., PPARa ligand protects during cisplatin-induced acute renal failure by preventing inhibition of renal FAO and PDC activity. Am. J Physiol. Renal Physiol. 286:F572-F580 (2004).
Lim et al., Nitrolinoleate, a nitric oxide-derived mediator of cell function: synthesis, characterization, and vasomotor activity. Proc. Natl. Acad. Sci. 99(25):15941-15946 (2002).
Lima et al., Characterization of linoleic acid nitration in human blood plasma by mass spectrometry. Biochem. 41(34):10717-10722 (2002).
Lima et al., Cholesteryl nitrolinoleate, a nitrated lipid present in human blood plasma and lipoproteins. J Lipid Res. 44:1660-1666 (2003).
Lima et al., Nitrated lipids decompose to nitric oxide and lipid radicals and cause vasorelaxation. Free Radical Bio. Med., Elsevier Sciences 39(4):532-539 (2005).
Liu et al., Accelerated reaction of nitric oxide with O2 within the hydrophobic interior of biological membranes. Proc. Natl. Acad. Sci. 95:2175-2179 (1998).
Liu et al., Combined Iosartan and nitro-oleic acid remarkably improves diabetic nephrophaty in mice. Am. J Physiol. Renal Physiol. 305:FI555-F1562 (2013).
Liu et al., Nitrol-oleic acid protects the mouse kidney from ischemia and reperfusion injury. Am. J Physiol. Renal Physiol. 295(4):F942-F949 (2008).
Liu et al.: Nitro-oleic acid protects against adriamycin-induced nephropathy in mice. Am J Physiol Renal Physiol. 305(11):F1533-F1541 (2013).
Lopez et al., Second generation of a-tocopherol analogs-nitric oxide donors: synthesis, physiochemical, and biological characterization. Bioorg. Med. Chem. 15:6262-6272 (2007).
Loytynoja et al., An algorithm for progressive multiple alignment of sequences with insertions. PNAS 102(30):10557-10562 (2005).
Lundberg et al., Nitrate and nitrite in biology, nutrition and therapeutics. Nat. Chem. Bio. 5(12):865-869 (2009).
Luzzio, The Henry reaction: recent examples. Tetrahedron 57:915-945 (2001).
Ma et al., Hydrohalogenation reaction of substituted 1, 2-allenic carboxylic acids, esters, amides, nitriles, and diphenyl phosphine oxides. Synthesis (5):713-730 (2001).
Manini et al., Chemistry of nitrated lipids: remarkable instability of 9-nitrolinoleic acid in neutral aqueous medium and a novel nitronitrate ester product by concurrent autoxidation/nitric oxide-release pathways. J Org Chem. 73(19):7517-7525 (2008).
March, Effects of Structure on Reactivity. Advanced Organic Chemistry (1977 edition), McGraw-Hill Book Company, New York, 251-259 (1977).
Marnett et al., Regulation of prostaglandin biosynthesis by nitric oxide is revealed by targeted deletion of inducible nitric-oxide synthese. J Biol. Chem. 275(18):13427-13430 (2000).
Marshall et al., Nitrosation and oxidation in the regulation of gene expression. FASEB Journal 14:1889-1900 (2000).
Martini, S. et al., Integrative biology identifies shared transcriptional networks in CKD. Journal of the American Society of Nephrology 25:2559-2572 (2014).
Marx et al., Peroxisome proliferator-activated receptors and atherogenesis: regulators of gene expression in vascular cells. Circ. Res. 94(9):1168-1178 (2004).
Mcintyre et al., Identification of an intracellular receptor for lysophosphatidic acid (LPA): LPA is a transcellular PPARy agonist. Proc. Natl. Acad. Sci. 100(1):131-136 (2003).
Mclean, Iodostarin. Archives of Internal Medicine 10:509 (1912).
Mehats, C. et al., (2002) "Cyclic Nucleotide Phosphodiesterases and their Role in Endocrine Cell Signaling" Trends In Endocrinol. & Metab. 13:29-35.
Menendez et al., Effects of gama-linolenic acid and oleic acid on paclitaxel cytotoxicity in human breast cancer cells. European J of Cancer (Oxford, England: 1990) 37(3):402-213 (2001).
Metabolite definition at https:/www.nlm.nih.gov/medlineplus/ency/article/002258.htm (retrieved from the internet Jan. 21, 2016).
Meyer et al., Uremia. New Engl. J Med. 357:1316-1325 (2007).
Miguel et al., Inhibition of phosphodiesterase 9A reduces cytokine-stimulated in vitro adhesion of neutrophils from sickle cell anemia individuals. Inflammation Research 60(7):633-42 (2011).
Minghetti, Cyclooxygenase-2 (COX-2) in inflammatory and degenerative brain diseases. J Neuropathol. Exp. Neural. 63(9):901-910 (2004).
Miranda et al., The Chemical Biology of nitric oxide. nitric oxide: Biology and Pathobiology 2000, Academic Press, San Diego, 41-55 (2000).
Mitschke et al., 9- and 10-Nitro-oleic acid do not interfere with the GC-MS quantitative determination of nitrite and nitrate in biological fluids when measured as their pentalfluorobenzyl derivatives. J Chromatography B. 85(1):287-291 (2007).
Montuschi et al., Isoprostanes: markers and mediators of oxidative stress. FASEB J. 18:1791-1800 (2004).
Morgan et al., Use of animal models of human disease for nonclinical safety assessment of novel pharmaceuticals. Toxicol. Pathol. 41(3):508-518 (2013).
Mukherjee et al., A selective peroxisome proliferator-activated receptor-gamma (PPARgamma) modulator blocks adipocyte differentiation but stimulates glucose uptake in 3T3-L1 adipocytes. Mol. Endocrinol. 14:1425-1433. (2000).
Nadtochiy et al. Mitochondrial nitroalkene formation and mild uncoupling in ischaemic preconditioning: implications for cardioprotection. Card. Res. Adv. Access 2008, 1-8 (2008).
Nadtochiy et al., Nitroalkenes confer acute cardioprotection via adenine nucleotide transloase I. J Biol. Chem. 287(5):3573-3580 (2012).
Nagano et al., Use of tacrolimus, a potent antifibrotic agent, in bleomycin-induced lung fibrosis. Eur. Respir. J. 27:460-469 (2006).
Nagasaki et al., Phosphodiesterase type 9 (PDE9) in the human lower urinary tract: an immunohistochemical study. BJU International 109(6):934-940 (2012).
Nagy et al., Oxidized LDL regulates macrophage gene expression through ligand activation of PPARy. Cell 93:229-240 (1998).
Napolitano et al., Acid-induced structural modifications of unsaturated fatty acids and phenolic olive oil constituents by nitrite ions: a chemical assessment. Chem. Res. Toxicol.17:1329-1337 (2004).
Napolitano et al., Acid-promoted reactions of ethyl linoleate with nitrite ions: formation and structural characterization of isomeric nitroalkene, nitrohydroxy, and novel 3-nitro-1,5-hexadiene and 1,5-Dinitro-1,3-pentadiene products. J Org. Chem. 65(16):4853-4860 (2000).
Napolitano et al., The acid-promoted reaction of ethyl linoleate with nitrite. New insights from 15N-labelling and peculiar reactivity of a model skipped diene. Tetrahedron 58:5061-5067 (2002).

(56) References Cited

OTHER PUBLICATIONS

Narayan et al., Serine threonine protein kinases of mycobacterial genus: phylogeny to function. Physiological Genomics 29:66-75 (2007).
Nathan, Nitric oxide as a secretory product of mammalian cells. FASEB J. 6:3051-3064 (1992).
Newman et al., Optimized thiol derivatizing reagent for the mass spectral analysis of distributed epoxy fatty acids. J Chromato. 925:223-240 (2011).
Niebisch et al., Corynebacterial protein kinase G controls 2-oxoglutarate dehydrogenase activity via the phosphorylation status of the OdhI protein. J Biol. Chem. 281(18):12300-12307 (2006).
NIH US National Library of Medicine, FIRSTx—A Study of Oral CXA-10 in Primary Focal Segmental Glomerusclerosis (FSGS). NCT03422510, Feb. 5, 2018, pp. 1-10 (2018).
Notredame et al., T-Coffee: A novel method for fast and accurate multiple sequence alignment. J Malec. Bio. 302:205-217 (2000).
Nott et al., An intramolecular switch regulates phosphoindependent FHA domain interactions in mycobacterium tuberculosis. Sci. Signaling 2(63):ra 12 (2009).
O'Donnell et al., 15-Lipoxygenase catalytically consumes nitric oxide and impairs activation of guanylae cyclase. J Biol. Chem. 274(29):20083-20091 (1999).
O'Donnell et al., Catalytic consumption of nitric oxide by prostagladin H synthase-I regulates platelet function. J Biol. Chem. 275(49):38239-38244 (2000).
O'Donnell et al., Interactions between nitric oxide and lipid oxidation pathways: implications for vascular disease. Circ. Res. 88:12-21 (2001).
O'Donnell et al., Nitration of unsaturated fatty acids by nitric oxide-derived reactive nitrogen species peroxynitrite, nitrous acid, nitrogen dioxide, and nitronium ion. Chem. Res. Toxicol. 12(1):83-92 (1999).
O'Donnell et al., Nitric oxide inhibition of lipid peroxidation: kinetics of reaction with lipid peroxyl radicals and comparison with a-tocopherol. Biochem. 36(49):15216-15223 (1997).
O'Hare et al., Regulation of glutamate metabolism by protein kinases in mycobacteria. Mol. Microbio. 70(6):1408-1423 (2008).
Ono et al., A convenient procedure for the conversion of E-nitroalkenes to (Z)-nitroalkenes via erythro—nitroselenides. J Chem. Soc., Chem Commun. 20:1550-1551 (1987).
Ortiz-Lombardia et al., Crystal structure of the catalytic domain of the PknB serine/threonine kinase from mycobacterium tuberculosis. J Biol. Chem. 278(15):13094-13100 (2003).
Padmaja, The reaction of nitric oxide with organic peroxyl radicals. Biochem. Biophys. Res. Commun. 195(2):539-544 (1993).
Park et al., Modulation of tumor necrosis factor-related apoptosis-inducing ligand-induced apoptosis by chemotherapy in thyroid cancer cell lines. Thyroid 13(12):1103-1110 (2003).
Pawliczak et al., 85-kDa cytosolic phospholipase A2 mediates peroxisome proliferator-activated receptor y activation in human lung epithelial cells. J Biol. Chem. 277:33153-33163 (2002).
PCT International Search Report and Written Opinion for PCT/US16/55206, dated Dec. 23, 2016.
PCT/CN2012/070718 International Search Report and Written Opinion dated Sep. 13, 2012.
PCT/EP2012/069936 International Search Report and Written Opinion dated Nov. 14, 2012.
PCT/EP2013/051451 International Search Report and Written Opinion dated Feb. 26, 2013.
PCT/EP2016/065964 International Search Report and Written Opinion dated Aug. 11, 2016.
PCT/US2018/034566 International Preliminary Report on Patentability dated Nov. 26, 2019.
PCT/US2018/034566 International Search Report and Written Opinion dated Aug. 21, 2018.
PCT/US2019/033835 International Preliminary Report on Patentability dated Dec. 1, 2020.
PCT/US2019/033835 International Search Report and Written Opinion dated Aug. 9, 2019.
PCT/US2019/048898 International Preliminary Report on Patentability dated Mar. 2, 2021.
PCT/US2019/048898 International Search Report and Written Opinion dated Nov. 25, 2019.
PCT/US2020/026696 International Search Report and Written Opinion dated Jun. 30, 2020.
PCT/US2020/031659 International Search Report and Written Opinion dated Jul. 31, 2020.
PCT/US2021/045765 Invitation to Pay Additional Fees dated Oct. 26, 2021.
Pharma Medica 20(5):199-210 (2002) (in Japanese with brief English relevance).
Pryor et al., Reaction of nitrogen dioxide with alkenes and polyunsaturated fatty acids: addition and hydrogen abstraction mechanisms. J Amer. Chem. Soc. 104:6685-6692 (1982).
PubChem CID 71550282 https://pubchem.ncbi.nlm.nih.gov/compound/71550282 (2013).
Punchard et al., The Journal of Inflammation Editorial; The Journal of Inflammation Sep., BioMed Central, 1(1):1-4 (2004).
Quijano et al., Reaction of peroxynitrite with Mn-superoxide dismutase: role of the metal center in decomposition kinetics and nitration. J of Biol. Chem. 276(15):11631-11638 (2001).
Radi et al., Peroxynitrite oxidation of sulfhydryls: the cytotoxic potential of superoxide and nitric oxide. J Biol. Chem. 266(7):4244-4250 (1991).
Radi et al., Peroxynitrite reactions with carbon dioxide-bicarbonate. Methods Enzymol. 301(37):353-367 (1999).
Ranu et al., Highly selective reduction of conjugated nitroalkenes with zinc borohydride in DME. Tetrahedron Letters 32(29):3579-3582 (1991).
Rassaf et al., Concomitant presence of n-nitroso and s-nitroso proteins in human plasma. Free Radic. Biol. Med. 33(11):1590-1596 (2002).
Rassaf et al., NO adducts in mammalian red blood cells: too much or too little? Nat. Med. 9(5):481-482 (2003).
Reema et al.: PDE-9 Inhibition combined with hydroxyurea is beneficial in vaso-occlusive crisis in mouse model of sickle cell disease. Blood. 124(21):1-2 (2014).
Rosen et al., PPARy: a nuclear regulator of metabolism, differentiation, and cell growth. J Biol. Chem. 276(1):37731-37734 (2001).
Rowe et al., Handbook of Pharma. Excipients 2006, 5th Ed., Great Britain: Pharmaceutical Press, American Pharmacists Association (2006).
Rubbo et al., Forum on nitric oxide: chemical events in toxicity. Nitric oxide regulation of tissue free radical injury. Chem. Res. Toxicol. 9(5):809-820 (1996).
Rubbo et al., Nitric oxide inhibition of lipoxygenase-dependent liposome and low-density lipoprotein oxidation: termination of radical chain propagation reactions and formation of nitrogen-containing oxidized lipid derivatives. Arch. Biochem. Biophys. 324(1):15-25 (1995).
Rubbo et al., Nitric oxide reaction with lipid peroxyl radicals spares a-tocopherol during lipid peroxidation. J Biol. Chem. 275(25):10812-10818 (2000).
Rubbo et al., Nitric oxide regulation of superoxide and peroxynitrite-dependent lipid peroxidation.J Biol. Chem. 269(42):26066-26075 (1994).
Rudnick et al., Contrast-induced nephropathy: How it develops, how to prevent it. Cleveland Clinic J Med. 73(1):75-87 (2006).
Rudolph et al., Cardiovascular consequences when nitric oxide and lipid signaling converge. Circ. Res. 105:511-522 (2009).
Rudolph et al., Endogenous generation and protective effects of nitro-fatty acids in murine model of focal cardiac ischaemia and reperfusion. Cardiov. Res. Advance Access 1-12 (2009).
Rudolph et al., Nitro-fatty acid metabolome: saturation, desaturation, -oxidation, and protein adduction. J Biol. Chem. 284(3):1461-1473 (2009).
Rudolph et al., Nitro-fatty acids reduce atherosclerosis in apolipoprotein e-deficient mice. Ather. Thromb. Vasc. Bio. 30:938-945 (2010).
Rudolph et al., Transduction of redox signaling by electrophile-protein reactions. Science Signaling. 2(90):re7 [1-13] (2009).

(56) References Cited

OTHER PUBLICATIONS

Ryan et al., Diabetes and the Mediterranean diet: a beneficial effect of oleic acid on insulin sensitivity, adipocyte glucose transport and endothelium-dependent vasoreactivity. Q. J Med. 93:85-91 (2000).
Saffer et al., Choosing drug therapy for patients with hyperlipidemia. Am. Fam. Physic. 61(11):3371-3382 (2000).
Sarver et al., Analysis of peptides and proteins containing nitrotyrosine by matrix-assisted laser desorption/ionization mass spectrometry. J Am. Soc. Mass Spectrom. 12(4):439-448 (2001).
Satyanarayana et al., Steroselective synthesis of diacids by the nickel cyanide and phase-transfer-catalyzed carbonylation of alkynols. Novel dependency of product stereochemistry and optimum stirring speed on the nature of the phase-transfer agent. Organometallics 10:804-807 (1991).
Saulnier-Blache et al., A simple and highly sensitive radioenzymatic assay for lysophosphatidic acid quantification. J Lipid Res. 2000, vol. 41, 1947-1951 (2000).
Scarpini et al., Treatment of Alzheimer's disease: current status and new perspectives. Lancet Neural. 2:539-547 (2003).
Scherr et al., Structural basis for the specific inhibition of protein kinase G, a virulence factor of *mycobacterium tuberculosis*. PNAS 104(29):12151-12156 (2007).
Schopfer et al., Covalent peroxisome proliferator-activated receptor gamma adduction by nitro-fatty acids: selective ligand activity and anti-diabetic signaling actions. J Biol. Chem. 285(16):12321-12333 (2010).
Schopfer et al., Detection and quantification of protein adduction by electrophilic fatty acids: mitochondrial generation of fatty acid nitroalkene derivatives. Free Radic. Biol. Med. 46:1250- 1259 (2009).
Schopfer et al., Fatty acid transduction of nitric oxide signaling. Nitrolinoleic acid is a hydrophobically stabilized nitric oxide donor. J Biol. Chem. 280(19):19289-19297 (2005).
Schopfer et al., Nitrolinoleic acid: an endogenous peroxisome proliferator-activated receptor y ligand. Proc. Natl. Acad. Sci. 102(7):2340-2345 (2005).
Schopfer et al., NO dependent protein nitration: a cell signaling event or an oxidative inflammatory response? Trends Biochem. Sci. 28:646-654 (2003).
Sculptoreanu et al., Nitro-oleic acid inhibits firing and activates TRPV-1 and TRPAI-mediated inward currents in dorsal root ganglion neurons from adult male rats. J Pharm. Expt. Thera. 333(3):883-895 (2010).
Serhan et al., Anti-inflammatory actions of neuroprotectin DI/protectin DI and its natural stereoisomers: assignments of dihydroxy-containing docosatrienes. J Immunology 176:1848-1859 (2006).
Setiadi et al., Vitamin E models. Conformational analysis and stereochemistry oftetralin, choman, thiochroman and selenochroman. J Molecular Structure (Theochem) 594:161-172 (2002).
Shaner et al., Designing herbicide tolerance based on metabolic alteration: the challenges and the future. In Pesticide Biotransformation in Plants and Microorganisms (Hall, J. et al.); ACS Symposium Series 2000, American Chemical Society; Washington DC, 353-374 (2000).
Sharpless et al., A mild procedure for the conversion of epoxides to allylic alcohols. The first organoselenium reagent. J Am. Chem. Soc. 95(8):2697-2699 (1973).
Sieker et al., Rubredoxin in crystalline state. Methods Enzymol. 243:203-216 (1994).
Simopoulos et al., Omega-3 fatty acids in inflammation and autoimmune diseases. J Amer. College of Nutrition 21(6):495-505 (2002).
Smith, Prostanoid biosynthesis and mechanisms of action. Am. Physiol. Soc. 263:F181-F191 (1992).
Snider et al., Oxidative and dehydrative cyclizations of nitroacetate esters with Mn (OAC). Tetrahedron 58(39):7821-7827 (2002).
Soding et al., HHsenser: exhaustive transitive profile search using HMM-HMM comparison. Nucleic Acids Res. 34:W374-378 (2006).
Strowig et al., Combination therapy using metformin or thiazolidinediones and insulin in the treatment of diabetes mellitus. Diabetes, Obesity, and Metabolism 7:633-641 (2005).
Subczynski et al., Permeability of nitric oxide through lipid bilayer membranes. Free Radic. Res. 24:343-349 (1996).
Szekely et al., A novel drug discovery concept for tuberculosis: inhibition of bacterial and host cell signaling. Immun. Letters 116(2):225-231 (2008).
Szoka et al., Comparative properties and methods of preparation of lipid vesicles (liposomes). Annual Review of Biophysics and Bio-engineering 9:467-508 (1980).
Tang et al., Nitroalkenes induce rat aortic smooth muscle cell apoptosis via activation of caspase-dependent pathways. Biochem. Biophvs. Res. Commun. 397:239-244 (2010).
Thatcher et al., Nitrates and no release: contemporary aspects in biological and medicinal chemistry. Free Radic. Biol. Med. 37(8)1122-1143 (2004).
Thomas et al., The biological lifetime of nitric oxide: implications for the perivascular dynamics of NO and O2. Proc. Natl. Acad. Sci. 98(1):355-360 (2001).
Tiwari et al., Key residues in *mycobacterium tuberculosis* protein kinase G play a role in regulating kinase activity and survival in the host. J Biol. Chem. 284(40):27467-27479 (2009).
Tontonoz et al., mPPARy2: tissue-specific regulator of an adipocyte enhancer. Genes Dev. 8(10):1224-1234 (1994).
Tontonoz et al., Stimulation of adipogenesis in fibroblasts by PPARy2, a lipid-activated transcription factor. Cell 79:1147-1156 (1994).
Toth, High-density lipoprotein and cardiovascular risk. Circulation 109:1809-1812 (2004).
Trostchansky et al., Nitrated fatty acids: mechanisms of formation, chemical characterization, and biological properties. Free Rad. Biol. Med. 44:1887-1896 (2008).
Tsikas et al., Nitro-fatty acids occur in human plasma in the picomolar range: a targeted nitro-lipidomics GC-MS/MS study. Lipids 44:855-865. (2009).
Tzameli et al., Regulated production of a peroxisome proliferatory-activated receptor-gamma ligand during an early phase of adipocyte differentiation in 3T3-LI adipocytes. J Biol. Chem. 279(34):36093-36102 (2004).
United States Office Action, U.S. Appl. No. 15/283,887, dated Feb. 8, 2019, 24 pages.
United States Office Action, U.S. Appl. No. 15/283,887, dated Jun. 14, 2018, 21 pages.
United States Office Action, U.S. Appl. No. 15/283,887, dated Nov. 16, 2017, 11 pages.
U.S. Appl. No. 16/315,365 Office Action dated Jul. 9, 2020.
U.S. Appl. No. 16/315,365 Restriction Requirement dated Oct. 7, 2019.
U.S. Appl. No. 16/615,347 Office Action dated Oct. 16, 2020.
U.S. Appl. No. 16/615,347 Office Action dated Sep. 2, 2021.
U.S. Appl. No. 16/673,709 Restriction Requirement dated Jun. 9, 2020.
Van Beilen et al., Rubredoxins involved in alkane oxidation. J Biol. Chem. 184(6):1722-1732 (2002).
Van der Staay, J.F. et al. (2008) "The Novel Selective PDE9 Inhibitor BAY 73-6691 Improved Learning and Memory in Rodents" Neuropharma 55(5):908-918.
Vasil'Ev et al., The action of nitrogen dioxide upon erucic acid. Lomonosova 5:50-58 (English abstract) (1995).
Verhoest et al., 2009, "Identification of a Brain Penetrant PDE9A Inhibitor Utilizing Prospective Design and chemical Enablement as a Rapic Lead Optimization Strategy", Journal of Medicinal Chemistry, vol. 52, No. 24, pp. 7946-7949.
Vickers et al., IGF-1 treatment reduces hyperphagia, obesity, and hypertension in metabolic disorders induced by fetal programming. Endocrinol. 142(9):3964-3973 (2001).
Vidwans et al., Differential modulation of prostaglandin H synthase-2 by nitric oxide-related species in intact cells. Biochem. 40:11533-11542 (2001).
Villacorta et al., Nitro-linoleic acid inhibits vascular smooth muscle cell proliferation via the Keap1/Nrf2 signaling pathway. Am. J Physiol. Heart Circ. Physiol. 293(1):H770-H776 [1-9] (2007).

(56) References Cited

OTHER PUBLICATIONS

Villacorta et al., PPARγ and its ligands: therapeutic implications in cardiovascular disease. Clin. Sci. 116:205-218 (2009).

Villacorta, L. et al., Electrophilic nitro-fatty acids inhibit vascular inflammation by disrupting LPS-dependent TLR4 signaling in lipid rafts. Cardiovascular Research 98(1):116-124 (2013).

Villarino et al., Proteomic identification of m. tuberculosis protein kinase substrates: PknB recruits GarA, a FHA domain-containing protein, through activation loop-mediated Interactions. J Mol. Bio. 350(5):953-963 (2005).

'Virtual Chembook' in www.elmhurst.edu/-chm/vchembook/55 Ifattyacids.html (retrieved Dec. 12, 2012).

Von Knethen et al., Activation of peroxisome proliferator-activated receptor y by nitric oxide in monocytes/macrophages down-regulates p47phox and attenuates the respiratory burst. J Immunol. 169:2619-2626 (2002).

Walburger et al., Protein kinase G from pathogenic mycobacteria promotes survival within macrophages. Sci. 304:1800-1804 (2004).

Wang et al., Constitutive activation of peroxisome proliferator-activated receptor-γ suppresses pro-inflammatory adhesion molecules in human vascular endothelial cells. J Biol. Chem. 277(37):34176-34181 (2002).

Wang et al., Effects of endogenous PPAR agonist nitro-oleic acid on metabolic syndrome in obese Zucker rats. PPAR Res. Art. ID 601562, 1-7 (2010).

Wang et al., Nitro-oleic acid protects against endotoxin-induced endotoxemia and multiorgan injury in mice. Am. J Physiol. Renal Physiol. 298:F754-F762 (2010).

Wang, H. et al., Nitrooleic acid attenuates lipid metabolic disorders and liver steatosis in DOCA-salt hypertensive mice. PPAR Research 2015:480348 [1-9] (2015).

Weber et al., Fragmentation of bovine serum albumin by pepsin. 1. The origin of the acid expansion of the albumin molecule. J Biol. Chem. 239(5):1415-1423 (1964).

Wehenkel et al., Mycobacterial Ser/Tur protein kinases and phosphatases: physiological roles and therapeutic potential. Biochemica et Biophysica Acta 1784(1):193-202 (2008).

Woodcock, Synthesis of nitrolipids. All four possible diastereomers of nitrooleic acids: (E)- and (Z)-, 9- and 10-nitro-octadec-9-enoic acids. Organic Letters 2006, 8(18):3931-3934 (2006).

Wright et al., Fatty acid transduction of nitric oxide signaling: Nitrolinoleic acid potently activates endothelial heme oxygenase 1 expression. PNAS 103(11)4299-4304 (2006).

Wright et al., Human heme oxygenase-1 induction by nitro-linoleic acid is mediated by cyclic Amp, AP-1, and e-box response element interactions. Biochem. J. 422(2):353-361 DOI:BJ20090339 [1-31] (2009).

Wunder, F. et al., (2005) "Charachertization of the First Potent and Selective PDE9 Inhibitor Using a cGMP Reporter sell Line" Mol. Pharmacol_ 68(6):1775-1781.

Xu et al., Lysophosphatidic acid as a potential biomaker for ovarian and other gynecologic cancers. JAMA 280:719-723 (1998).

Zhang et al., Lysophosphatidic acid induces neointima formation through PPARgamma activation. J Ex Med. 199(6):763-774 (2004).

Zhang et al., Nitro-oleic acid inhibits angiotensin II-induced hypertension. Circ. Res. 107:540- 548 (2010).

Zhang et al., Selective disruption of PPARgamma2 impairs the development of adipose tissue and insulin sensitivity. Proc. Natl. Acad. Sci. 101(29):10703-10708 (2004).

Zhou, M. et al., (1994) "Role of Guanylyl Cyclase and cGMP-dependent Protein Kinase in Long-Term Potentiation" Nature 36(6472):635-639.

Cains, P.W.; "Classical Methods of Preparation of Polymorphs and Alternative Solid Forms," Polymorphism in Pharmaceutical Solids, 2nd Ed., (2009), Chapter 4, pp. 76-138.

Caira, M. R., "Crystalline Polymorphism of Organic Compounds", Topics in Current Chemistry (Jan. 1, 1998); 198:163-208.

Japanese Office Action for Japanese Patent Application No. 2020-564326, dated Apr. 25, 2023, 4 pages; English Translation.

Khankari et al. "Pharmaceutical hydrates", Thermochimica Acta, (1995); 248:61-79.

Price, S.L.; "Computational Methodologies: Toward Crystal Structure and Polymorph Prediction," Polymorphism in Pharmaceutical Solids, 2nd Ed., (2009), Chapter 3, pp. 52-75.

Takata, Noriyuki, "API form screening and selection in drug discovery stage," Sentaku, Pharm Stage, Technical Information Institute, JP, (Jan. 1, 2007); 6(10): pp. 20-25 (Japanese).

MONOHYDRATE AND CRYSTALLINE FORMS OF 6-[(3S,4S)-4-METHYL-1-(PYRIMIDIN-2-YLMETHYL)PYRROLIDIN-3-YL]-3-TETRAHYDROPYRAN-4-YL-7H-IMIDAZO[1,5-A]PYRAZIN-8-ONE

REFERENCE TO RELATED APPLICATIONS

This application is a continuation of PCT International Application No. PCT/US2019/033835, filed May 23, 2019, which claims priority to U.S. Provisional Application No. 62/788,323 filed Jan. 4, 2019 and U.S. Provisional Application No. 62/676,381, filed May 25, 2018, each of which are incorporated herein by reference in their entireties.

FIELD OF THE DISCLOSURE

The present disclosure relates to polymorphic forms of a cyclic guanylate monophosphate (cGMP)-specific phosphodiesterase type 9 inhibitor (hereinafter referred to as PDE9 inhibitor).

BACKGROUND

Solids exist in either amorphous or crystalline forms. Polymorphism relates to various crystalline forms of a chemical substance. These crystalline forms have different characteristics in structures and physical properties, such as XRPD spectrum, IR spectrum, and melting point. A particular polymorph form may have advantages over other forms and more suitable for the manufacture and use of the drug substance 6-[(3S,4S)-4-methyl-1-(pyrimidin-2-ylmethyl)pyrrolidin-3-yl]-3-tetrahydropyran-4-yl-7H-imidazo[1,5-a]pyrazin-8-one (Compound 1) is a PDE9 inhibitor disclosed in WO 2017/005786 for treating various diseases such as sickle cell disease. Improved forms of Compound 1 are desired, particularly with regard to enhanced solubility, oral bioavailability, and/or physical stability.

SUMMARY OF THE DISCLOSURE

The present disclosure provides polymorph forms of a PDE9 inhibitor: 6-[(3S,4S)-4-methyl-1-(pyrimidin-2-ylmethyl)pyrrolidin-3-yl]-3-tetrahydropyran-4-yl-7H-imidazo[1,5-a]pyrazin-8-one (Compound 1), referred to herein as Form MH1 and Form MH2. The present disclosure also provides methods of making the polymorph forms, characterization of the polymorph forms, pharmaceutical compositions comprising the polymorph forms, and methods of using the polymorph forms and compositions.

One aspect of the disclosure provided herein comprises a monohydrate crystalline form of 6-[(3S,4S)-4-methyl-1-(pyrimidin-2-ylmethyl)pyrrolidin-3-yl]-3-tetrahydropyran-4-yl-7H-imidazo[1,5-a]pyrazin-8-one

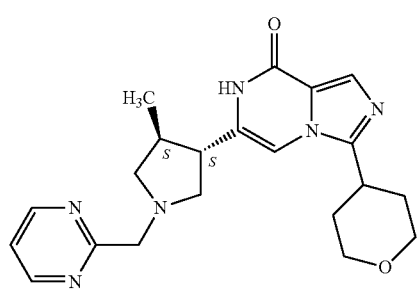

(Compound 1)

In some embodiments, the monohydrate crystalline form is MH1, having an XRPD pattern comprising peaks of 2θ angles at about 9.1, 11.5, 16.2, 16.7, 18.2, 18.9, 19.8, 22.6, and 26.4 degrees 2θ, each ±0.2 degrees 2θ. In some embodiments, the monohydrate crystalline form is MH1, having an XRPD pattern substantially as shown in FIG. 2A. In some embodiments, the monohydrate crystalline form is MH1, having a dehydration endothermic peak at about 40-100° C. and a melting endothermic peak at about 184.4° C. in a differential scanning calorimetry (DSC) thermogram. In some embodiments, the monohydrate crystalline form is MH1, having a DSC thermogram substantially in accordance with FIG. 5. In some embodiments, the monohydrate crystalline form is MH1, exhibiting dehydration between ambient and about 90° C. with a weight loss of about 4.4% in a thermogravimetric analysis (TGA). In some embodiments, the monohydrate crystalline form is MH1, having a TGA substantially in accordance with FIG. 5. In some embodiments, the monohydrate crystalline form is MH1, having characteristic absorptions at about 782 $cm^{-1}$, 1123 $cm^{-1}$, 1562 $cm^{-1}$ and 1655 $cm^{-1}$ in an infrared (IR) spectrum. In some embodiments, the monohydrate crystalline form is MH1, having an infrared spectrum substantially in accordance with FIG. 3. In some embodiments, the monohydrate crystalline form is MH2, having an XRPD pattern comprising peaks of 2θ angles at about 9.0, 11.6, 15.0, 16.0, 18.6, 19.1, 20.4, or 20.6 degrees 2θ, each ±0.2 degrees 2θ. In some embodiments, the monohydrate crystalline form is MH2, having an XRPD pattern substantially as shown in FIG. 7. In some embodiments, the monohydrate crystalline form is MH2, having an endothermic peak at about 59.1° C. (±5° C.) and at about 184.7° C. (±5° C.) in a differential scanning calorimetry (DSC) thermogram. In some embodiments, the monohydrate crystalline form is MH2, having a DSC thermogram substantially in accordance with FIG. 9. In some embodiments, the monohydrate crystalline form is MH2, exhibiting dehydration at about 25° C. to about 100° C. with a weight loss of about 4.4% in a thermogravimetric analysis (TGA). In some embodiments, the monohydrate crystalline form is MH2, having a TGA substantially in accordance with FIG. 9. In some embodiments, the monohydrate crystalline form is at least 95, 96, 97, 98, or 99% purified.

Another aspect described herein comprises a pharmaceutical composition comprising a therapeutically effective amount of the monohydrate crystalline form in any one of the embodiments described herein, and a pharmaceutically acceptable excipient. In some embodiments, the monohydrate crystalline form is present in an amount of at least about 90%, 91%, 92%, 93%, 94%, 95%, 96%, 97%, 98%, or 99% by weight. In some embodiments, the monohydrate crystalline form is present in an amount of at least about 91% by weight.

Another aspect described herein comprises a pharmaceutical composition consisting essentially of the monohydrate crystalline form of any one of the embodiments described herein.

Another aspect described herein comprises a pharmaceutical composition consisting essentially of the monohydrate crystalline form MH1 of any one of the embodiments described herein.

Another aspect described herein comprises a pharmaceutical composition consisting essentially of the monohydrate crystalline form MH2 of any one of the embodiments described herein. In some embodiments, the composition is in tablet or capsule form.

Another aspect described herein comprises a process for preparing a monohydrate crystalline form of Compound 1, comprising precipitating the monohydrate crystalline form from a solution comprising Compound 1 and a solvent selected from the group consisting of n-propyl acetate, isopropyl acetate, anisole, methylisobutyl ketone, cumene, isopropanol, 2-methyl tetrahydrofuran, and combinations thereof. In some embodiments, the solvent is n-propyl acetate. In some embodiments, the process further comprises cooling the solution.

Another aspect described herein comprises a monohydrate crystalline form of Compound 1 prepared by the process of any one of the embodiments described herein.

Another aspect described herein comprises a method of inhibiting PDE9 activity in a patient, comprising administering to the patient the monohydrate crystalline form of any one of the embodiments described herein.

Another aspect described herein comprises a method of treating sickle cell disease in a patient in need thereof, comprising administering to the patient a therapeutically effective amount of the monohydrate crystalline form of any one of the embodiments described herein.

Another aspect described herein comprises a process for preparing Monohydrate Form 1 (MH1) of Compound 1, the steps comprising: (i) dissolving Compound 1 in a first solvent to get a solution; (ii) adding a second solvent to get a mixture; and (iii) filtering the mixture to get a solid, wherein the first and second solvent is each individually selected from selected from isopropyl acetate; ethanol; tetrahydrofuran; water; dichloromethane; acetonitrile; anisole; methylisobutyl ketone; nitromethane; 1,2-dimethoxyethane; methylethyl ketone; n-heptane; 1,4-dioxane; n-propyl acetate; 2-propanol; acetone; cumene; N,N-dimethylformamide; dimethyl sulfoxide; and combinations thereof. In some embodiments, the method further comprises heating the solution to a temperature above room temperature at about 35, 40, 45, 50, 55, 60, 65, 70, 75, or 80° C.

In some embodiments, the first solvent comprises 2-propanol. In some embodiments, the second solvent comprises n-heptane. In some embodiments, the first solvent in step (i) comprises water and 2-propanol. In some embodiments, the water content of the solution obtained in step (i) is about 0.5%, 1%, or 1.5%. In some embodiments, the water content of the solution obtained in step (i) is about 1%. In some embodiments, the solid obtained in step (ii) is optionally washed one or more times with n-heptane. In some embodiments, the process further comprises drying the solid after step (iii). In some embodiments, the solid is dried in a humidified.

Another aspect described herein comprises a process for preparing Monohydrate Form 2 (MH2) of Compound 1, the steps comprising: a) treating Compound 1 or MH1 with a first solvent system to obtain a suspension; b) filtering the suspension to obtain the solid; c) washing the solid with heptane; and d) drying to remove the solvent to get MH2; wherein the solvent is a mixture of water and ethyl acetate (EtOAc) or methyl acetate (MeOAc), selected from 2% (v/v) EtOAc/water, 2.7% (v/v) EtOAc/water, and 7.5% (v/v) MeOAc/water.

DETAILED DESCRIPTION

I. Polymorph Forms of Compound 1

Figure 1:
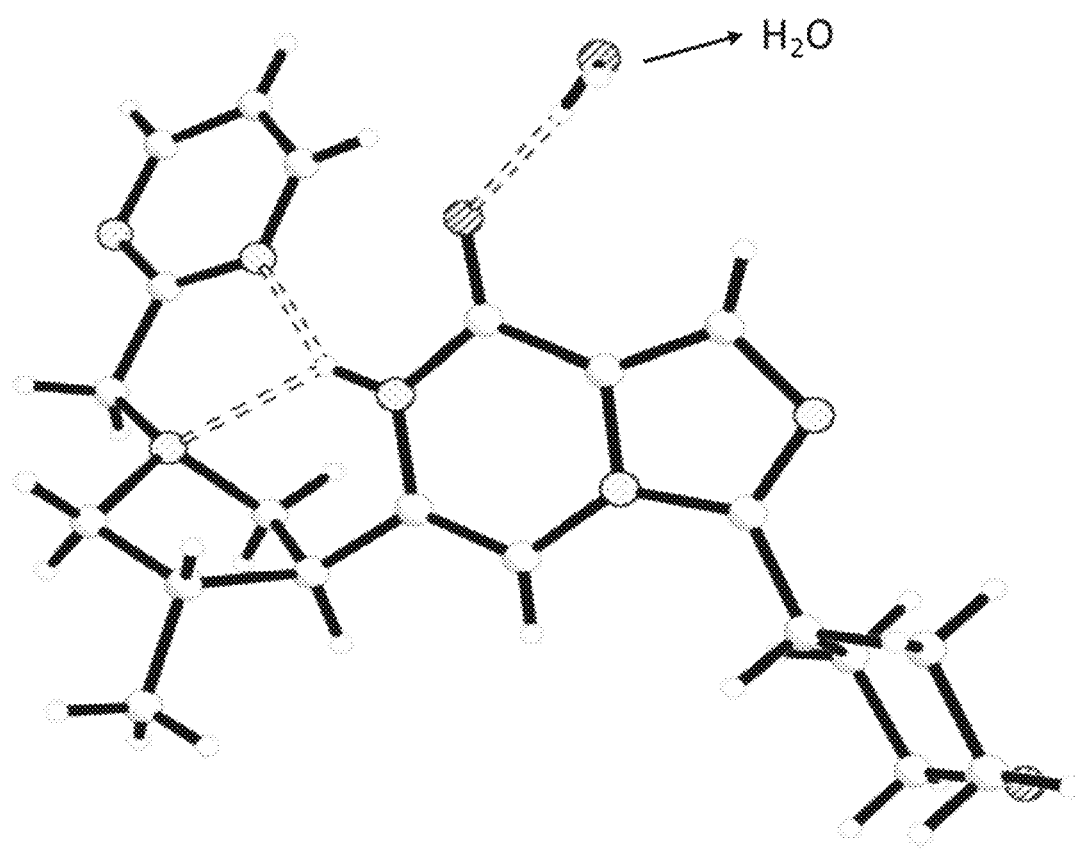
FIG. 1 is the ball and stick diagram of MH1 molecular structure.

A racemate form of Compound 1 and an anhydrous form of Compound 1 have been described in WO 2013/053690 and WO 2017/005786. The anhydrous form of Compound 1 has the following structure:

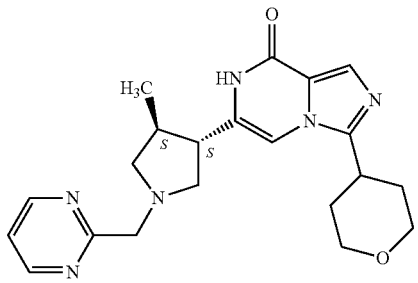

6-[(3S,4S)-4-methyl-1-(pyrimidin-2-ylmethyl)pyrrolidin-3-yl]-3-tetrahydropyran-4-yl-7H-imidazo[1,5-a]pyrazin-8-one Two different monohydrate polymorph forms of Compound 1 have been discovered, Monohydrate Form 1 (MH1) and Monohydrate Form 2 (MH2). The two monohydrate forms and the anhydrate form (AH) differ in their crystal structure as determined by single crystal X-ray Powder Diffraction (XRPD). The main peaks of MH1 and MH2 below 30° 2θ were identified and their relative intensities are listed in Table 1. As will be understood by a person skilled in the art, the relative intensities of the peaks within Table 1 may vary due to various factors such as the purity of the material being analyzed, orientation effects of crystals in the X-ray beam, the degree of crystallinity of the sample, and so on. The peak positions may also shift for variations of sample height, but the peak positions will remain substantially as defined in Table 1. A person skilled in the art will also understand that measurements using a different wavelength will result in different shifts according to the Bragg equation ($n\lambda = 2d \sin \theta$). Such further XRPD patterns generated by use of alternative wavelengths are alternative representations of the XRPD patterns of the crystalline materials.

TABLE 1

XRPD peak listing for MH1 and MH2.

| MH1 | | MH2 | |
|---|---|---|---|
| °2θ | Intensity % | °2θ | Intensity % |
| 8.2 | 9.7 | 8.5 | 12.8 |
| 9.1 | 70.4 | 9.0 | 48.1 |
| 11.5 | 36.8 | 10.2 | 4.1 |
| 12.6 | 4.3 | 11.6 | 45.8 |
| 14.8 | 2.8 | 12.2 | 8.9 |
| 15.0 | 9.2 | 12.6 | 8.7 |
| 16.2 | 100 | 13.0 | 11.9 |
| 16.5 | 10 | 15.0 | 40.2 |
| 16.7 | 23.6 | 16.0 | 100 |
| 17.7 | 3.3 | 16.5 | 7.1 |
| 18.2 | 22.4 | 17.0 | 28.1 |
| 18.9 | 46.3 | 17.7 | 15.6 |
| 19.3 | 5.2 | 18.6 | 80.9 |
| 19.8 | 42.7 | 18.7 | 7.7 |
| 20.7 | 18.3 | 19.1 | 79.3 |
| 21.0 | 18.1 | 19.2 | 35.6 |
| 21.4 | 3.8 | 20.4 | 43.3 |
| 22.3 | 6.1 | 20.6 | 55 |
| 22.6 | 20.9 | 20.8 | 10.9 |
| 23.0 | 4.8 | 21.1 | 11.6 |
| 24.4 | 14 | 22.1 | 18.5 |
| 25.2 | 7.9 | 22.6 | 9.4 |
| 25.8 | 3.7 | 22.7 | 12.5 |
| 26.4 | 21.5 | 24.1 | 30.4 |
| 26.7 | 7.3 | 24.7 | 6.7 |
| 27.6 | 4 | 25.1 | 7.1 |
| 29.2 | 8.8 | 25.3 | 12.3 |
| | | 25.9 | 8.4 |
| | | 26.2 | 23.9 |
| | | 26.7 | 32.6 |
| | | 27.3 | 24.1 |
| | | 27.9 | 20.7 |
| | | 28.4 | 6.4 |
| | | 28.5 | 5.7 |
| | | 28.9 | 11.3 |
| | | 29.6 | 8.9 | i. Crystalline Form MH1

Form MH1 may be characterized by any of its peaks in Table 1. For example, MH1 may be characterized by any of the following peaks, among others: 9.1, 11.5, 16.2, 16.7, 18.2, 18.9, and 19.8 degrees 2θ, each ±0.2 degrees 2θ.

In some embodiments, the monohydrate crystalline form of Compound 1 is MH1 and has an X-ray powder diffraction (XRPD) pattern comprising one or more peaks of any of 9.1, 11.5, 16.2, 16.7, 18.2, 18.9, and 19.8 degrees 2θ, each ±0.2 degrees 2θ.

In some embodiments, the monohydrate crystalline form of Compound 1 is MH1 and has an X-ray powder diffraction (XRPD) pattern comprising peaks of 9.1, 11.5, 16.2, 16.7, 18.2, 18.9, and 19.8 degrees 2θ, each ±0.2 degrees 2θ.

Figure 3:
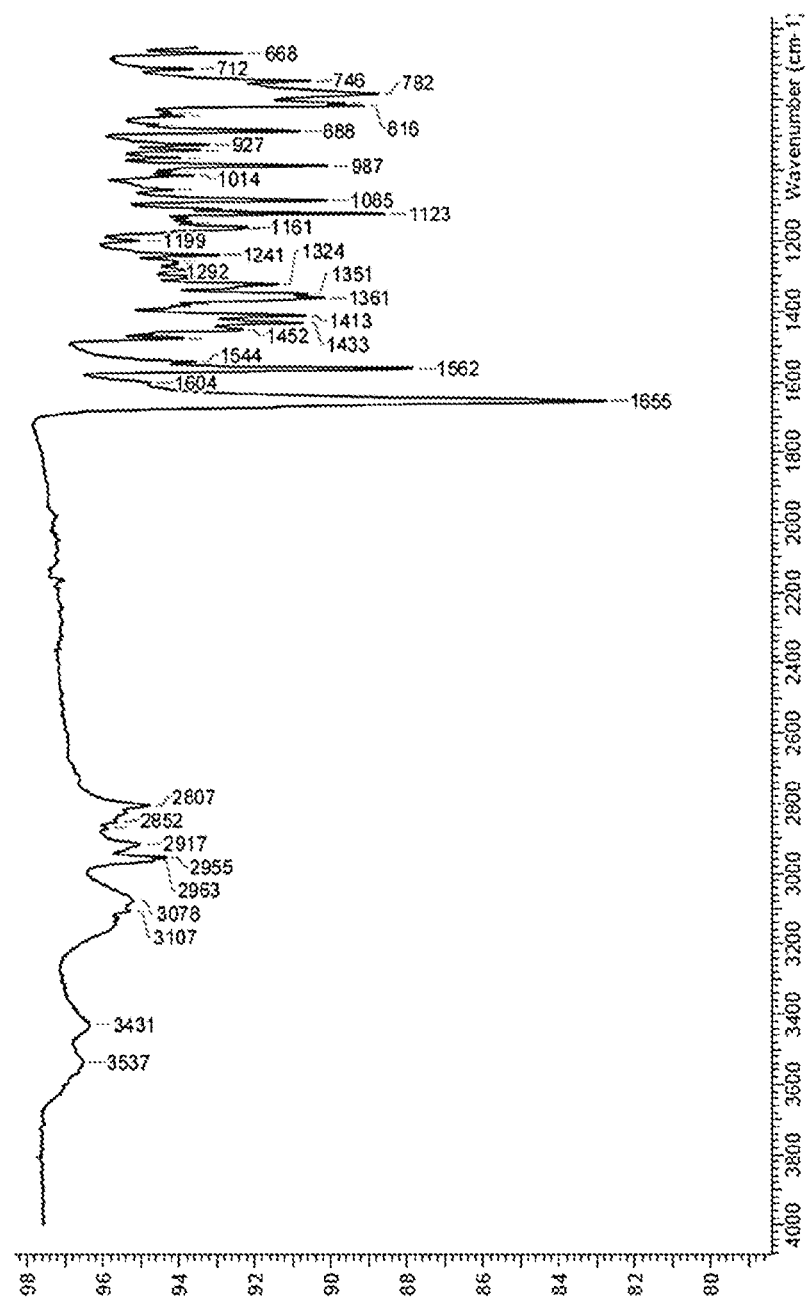
FIG. 3 is the FTIR spectrum of MH1.

In some embodiments, MH1 analysed with infrared (IR) spectroscopy exhibits characteristic absorptions at about 782 cm$^{-1}$, 1123 cm$^{-1}$, 1562 cm$^{-1}$ and 1655 cm$^{-1}$ (±0.5 cm$^{-1}$) as shown in FIG. 3.

In some embodiments, MH1 analysed by differential scanning calorimetry (DSC) thermogram shows a dehydration endothermic peak at about 40-100° C. (±10° C.) and a melting endothermic peak at about 184.4° C. (±5° C.) as shown in FIG. 5.

Figure 5:
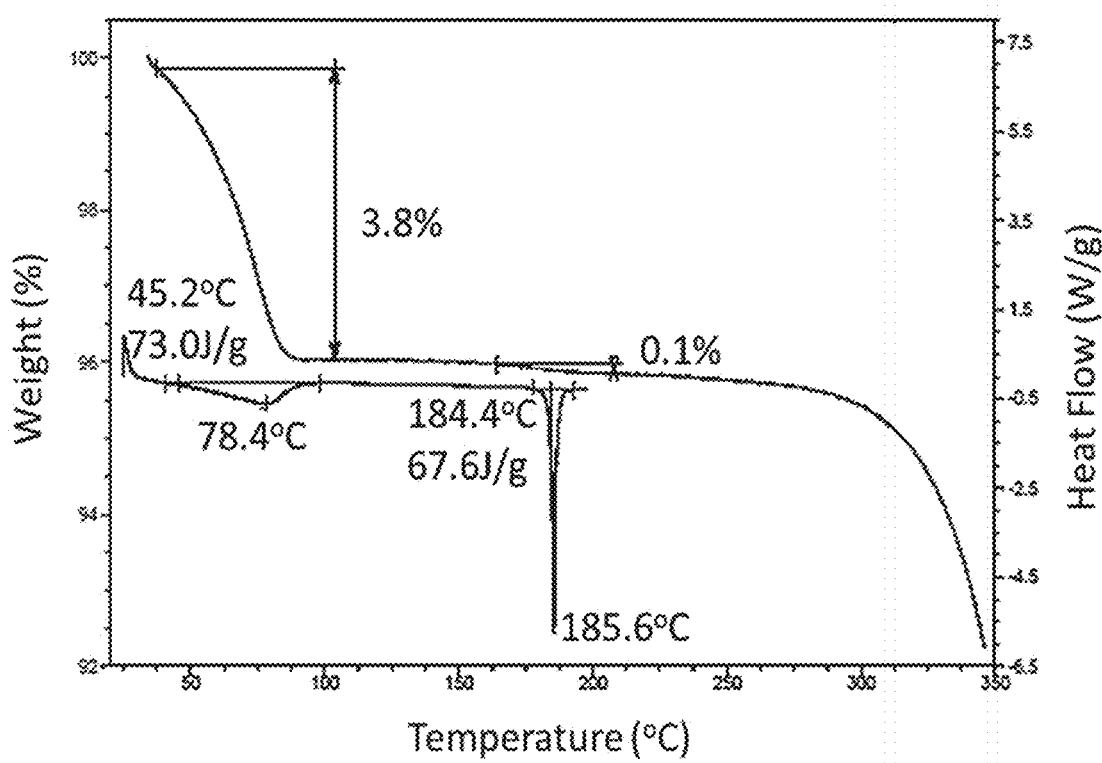
FIG. 5 is the TGA and DSC analysis of MH1.
Figure 6:
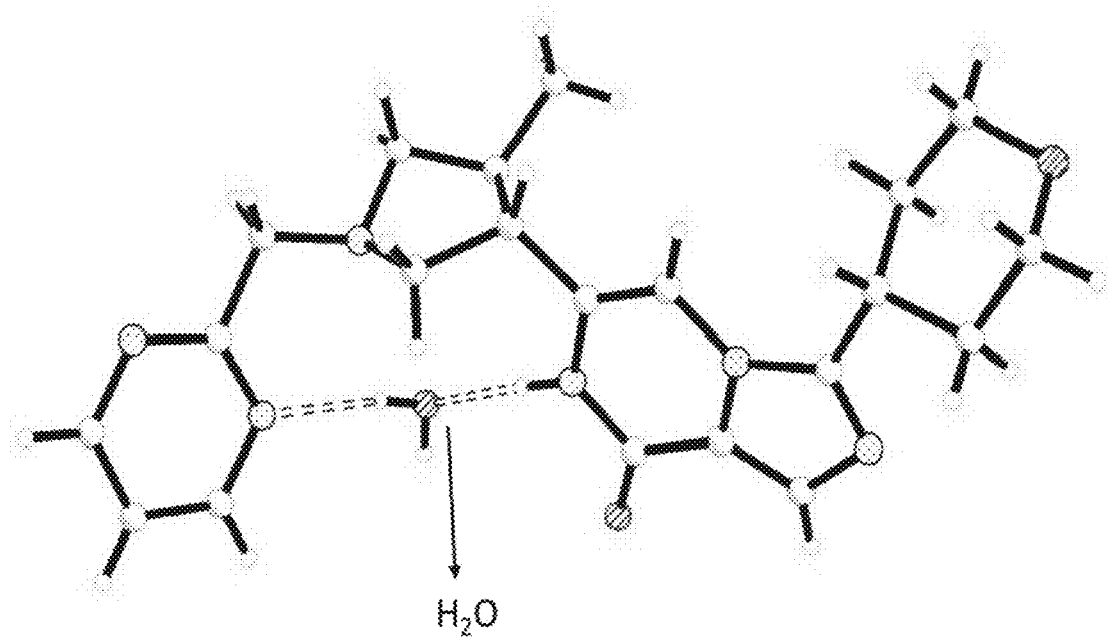
FIG. 6 is the ball and stick diagram of MH2 molecular structure.

In some embodiments, MH1 analysed by thermogravimetric analysis (TGA) exhibits a dehydration at ambient to about 90° C. with a weight loss of about 3.8% as shown in FIG. 5.

ii. Crystalline Form MH2

Form MH2 may be characterized by any of its peaks in Table 1. For example, MH2 may be characterized by any of the following peaks, among others: 9.0, 11.6, 15.0, 16.0, 18.6, 19.1, 20.4, and 20.6 degrees 2θ, each ±0.2 degrees 2θ.

In some embodiments, the monohydrate crystalline form of Compound 1 is MH2 and has an X-ray powder diffraction (XRPD) pattern comprising one or more peaks of any of 9.0, 11.6, 15.0, 16.0, 18.6, 19.1, 20.4, or 20.6 degrees 2θ, each ±0.2 degrees 2θ.

In some embodiments, the monohydrate crystalline form of Compound 1 is MH2 and has an X-ray powder diffraction (XRPD) pattern comprising peaks of 9.0, 11.6, 15.0, 16.0, 18.6, 19.1, 20.4, and 20.6 degrees 2θ, each ±0.2 degrees 2θ.

In some embodiments, MH2 analysed by differential scanning calorimetry (DSC) thermogram shows an endothermic peak at about 59.1° C. (±5° C.) and at about 184.7° C. (±5° C.) as shown in FIG. 9.

Figure 9:
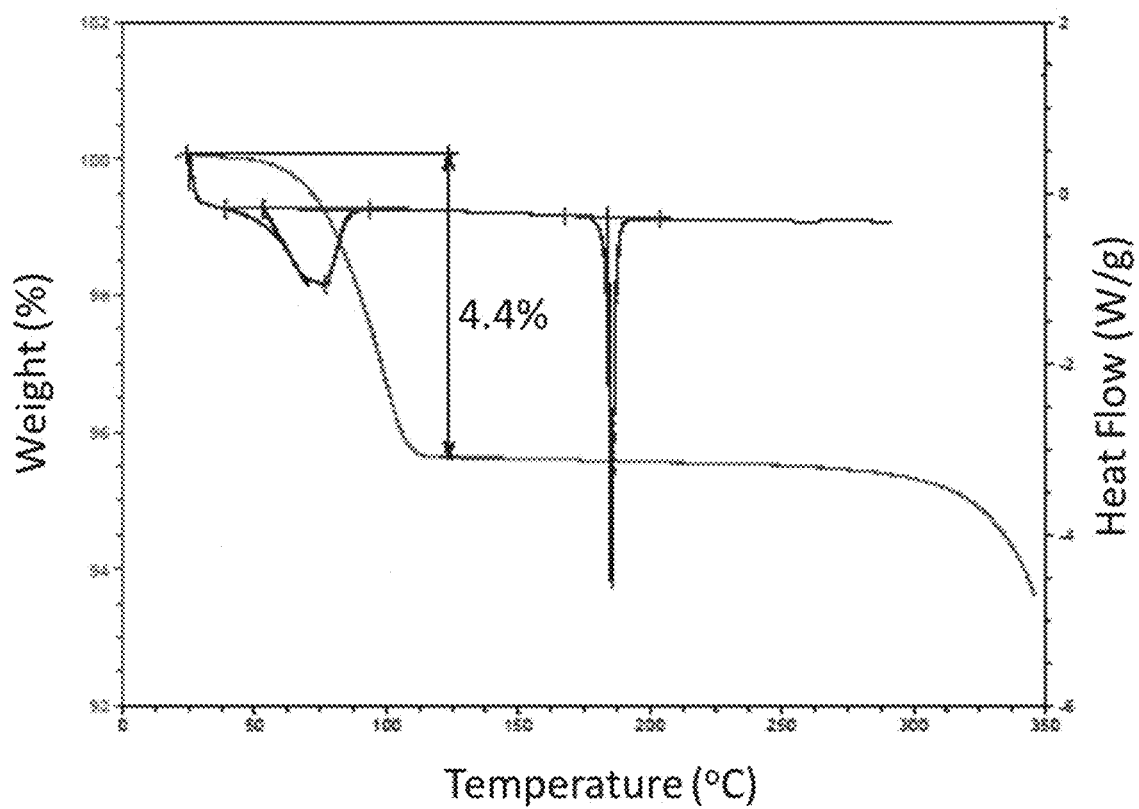
FIG. 9 is the TGA and DSC analysis of MH2.

In some embodiments, MH2 analysed by thermogravimetric analysis (TGA) exhibits a dehydration at about 25° C. to about 100° C. with a weight loss of about 4.4% as shown in FIG. 9.

In some embodiments, the crystalline form of Compound 1 (e.g. MH1 or MH2) is substantially pure. In some embodiments, the crystalline form MH1 or MH2 is at least 80%, 85%, 90%, or 95% pure. In some embodiments, the crystalline form MH1 or MH2 is at least 95%, 96%, 97%, 98%, or 99% pure. In some embodiments, the crystalline form MH1 or MH2 contains no more than 10%, 5%, 3%, or 1% impurity.

II. Pharmaceutical Compositions

The present disclosure further provides a pharmaceutical composition comprising a therapeutically effective amount of any of the polymorph forms of Compound 1 (such as monohydrate crystalline form MH1 or MH2) and a pharmaceutically acceptable excipient, carrier or diluent. In some embodiments, the pharmaceutical composition is for oral administration. In some embodiments, the pharmaceutical composition is in tablet form or capsule form.

The polymorph forms of Compound 1 (such as monohydrate crystalline form MH1 or MH2) may be administered alone or in combination with pharmaceutically acceptable carriers, diluents or excipients, in either single or multiple doses. The pharmaceutical compositions according to the disclosure may be formulated with pharmaceutically acceptable carriers or diluents as well as any other known adjuvants and excipients in accordance with conventional techniques such as those disclosed in Remington: The Science and Practice of Pharmacy, 22nd Edition, Gennaro, Ed., Mack Publishing Co., Easton, PA, 2013.

Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Other suitable administration forms include, but are not limited to, suppositories, sprays, ointments, creams, gels, inhalants, dermal patches and implants.

Typical oral dosages range from about 0.001 to about 100 mg/kg body weight per day. Typical oral dosages also range from about 0.01 to about 50 mg/kg body weight per day. Typical oral dosages further range from about 0.05 to about 10 mg/kg body weight per day. Oral dosages are usually administered in one or more dosages, typically, one to three dosages per day. The exact dosage will depend upon the frequency and mode of administration, the gender, age, weight and general health of the subject treated, the nature and severity of the condition treated and any concomitant diseases to be treated and other factors evident to those skilled in the art.

The formulations may also be presented in a unit dosage form by methods known to those skilled in the art. For illustrative purposes, a typical unit dosage form for oral administration may contain from about 0.01 to about 1000 mg, from about 0.05 to about 500 mg, or from about 0.5 mg to about 200 mg.

For parenteral routes such as intravenous, intrathecal, intramuscular and similar administration, typical doses are on the order of half the dose employed for oral administration.

The present disclosure also provides a process for making a pharmaceutical composition comprising admixing a therapeutically effective amount of any of the polymorph forms of Compound 1 (such as monohydrate crystalline form MH1 or MH2) and at least one pharmaceutically acceptable carrier or diluent.

Suitable pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compounds of the present disclosure and a pharmaceutically acceptable carrier are then readily administered in a variety of dosage forms suitable for the disclosed routes of administration. The formulations may conveniently be presented in unit dosage form by methods known in the art of pharmacy.

Formulations of the present disclosure suitable for oral administration may be presented as discrete units such as capsules or tablets, each containing a predetermined amount of the active ingredient, and optionally a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tabletted, placed in a hard gelatine capsule in powder or pellet form or it may be in the form of a troche or lozenge. The amount of solid carrier will vary widely but will range from about 25 mg to about 1 g per dosage unit. If a liquid carrier is used, the preparation may be in the form of a syrup, emulsion, soft gelatine capsule or sterile injectable liquid such as an aqueous or non-aqueous liquid suspension or solution.

The pharmaceutical compositions of the disclosure may be prepared by conventional methods in the art. For example, tablets may be prepared by mixing the active ingredient with ordinary adjuvants and/or diluents and subsequently compressing the mixture in a conventional tabletting machine prepare tablets. Examples of adjuvants or diluents comprise: corn starch, potato starch, talcum, magnesium stearate, gelatin, lactose, gums, and the like. Any other adjuvants or additives usually used for such purposes such as colorings, flavorings, preservatives etc. may be used provided that they are compatible with the active ingredients.

In some embodiments, the pharmaceutical compositions comprise at least 10%, 20%, 30%, 40%, 50%, 60%, 70%, 80%, or 90% by weight of a polymorph form of Compound 1 (such as monohydrate crystalline form MH1 or MH2). In some embodiments, the pharmaceutical compositions comprise at least 91%, 92%, 93%, 94%, 95%, 96%, 97%, 98%, or 99% by weight of a polymorph form of Compound 1 (such as monohydrate crystalline form MH1 or MH2).

In one embodiment, the pharmaceutical composition comprising compounds of the present disclosure is used in combination with one or more additional active agents, such as hydroxyurea ("HU").

III. Methods of Making Polymorph Forms of Compound 1

Crystallization can be precipitated from a solution comprising a compound and a solvent. For example, crystallizations can be obtained by lowering the temperature of a clear solution. The solubility of most materials decreases with temperature, and hence, cooling can be used to cause supersaturation. Crystallization can also be obtained by fast evaporation.

In some embodiments, MH1 crystals are made in a crystallization process. In some embodiments, MH2 crystals are made in a crystallization process.

Crystals of Compound 1 can be prepared by dissolving Compound 1 in a solvent to obtain a saturated solution of Compound 1 and then cooling the saturated solution to precipitate the crystals.

Crystals of monohydrate form MH1 or MH2 can be prepared by precipitating the crystals from a solution comprising Compound 1 and a solvent. The solvent is selected from the group consisting of ethanol; tetrahydrofuran; water; dichloromethane; acetonitrile; nitromethane; 1,2-dimethoxyethane; methylethyl ketone; 1,4-dioxane; 2-propanol; acetone; cumene; N,N-dimethylformamide; dimethyl sulfoxide; n-propyl acetate; isopropyl acetate; anisole; methylisobutyl ketone; 2-methyl tetrahydrofuran; and combinations thereof. For example, Compound 1 can be suspended in a solvent, e.g. n-propyl acetate, to obtain a suspension, filtering the suspension to get a solution (i.e., mother liquor) and then cooling the solution (i.e., mother liquor) to precipitate the crystals.

In some embodiments, MH1 or MH2 crystals can be prepared by the steps comprising:
  (i) suspending Compound 1 in a first solvent at room temperature (RT) to form a suspension;
  (ii) heating the suspension obtained in step (i) to a temperature above RT, (e.g., from about 40° C. to about 60° C.);
  (iii) adding a second solvent to the suspension obtained in step (ii) to form a mixture and heating the mixture to a temperature above RT, (e.g., from about 40° C. to about 60° C.);
  (iv) optionally filtering the mixture obtained in step (iii) to obtain a solution (i.e., mother liquors); and
  (v) cooling the mixture obtained in step (iii) or the solution obtained in step (iv) to a temperature below RT, (e.g., about 4° C.), to precipitate MH1 or MH2 crystals; wherein the first and second solvent are each independently selected from the group consisting of n-heptane; ethanol; tetrahydrofuran; water; dichloromethane; acetonitrile; nitromethane; 1,2-dimethoxyethane; methylethyl ketone; 1,4-dioxane; 2-propanol; acetone; cumene; N,N-dimethylformamide; dimethyl sulfoxide; n-propyl acetate; isopropyl acetate; anisole; methylisobutyl ketone; 2-methyl tetrahydrofuran; and combinations thereof.

In some embodiments, the first and second solvents are each independently selected from methylethyl ketone; 1,4-dioxane; 2-propanol; acetone; n-propyl acetate; isopropyl acetate; anisole; methylisobutyl ketone; cumene; n-heptane; 2-methyl tetrahydrofuran; and combinations thereof. In some embodiments, the first and second solvent are each independently selected from n-propyl acetate or n-heptane.

In some embodiments, the first and second solvents are the same. In some embodiments, the first and second solvents are different.

In some embodiments of MH1, the first solvent is selected from n-prolyl acetate and the second solvent is selected from n-heptane.

In some embodiments, the volume of the first solvent used in step (i) is less than the volume of the second solvent used in step (iii). For example, the ratio of the volume of the first solvent used in step (i) to the volume of the second solvent used in step (iii) is around 1:1.5, 1:2, 1:2.5, 1:3, 1:3.5, 1:4, 1:4.5, or 1:5. In one example, the ratio of the volume of the first solvent used in step (i) to the volume of the second solvent used in step (ii) is around 1:2.

In some embodiments, the temperature above RT in steps (ii) and (iii) is from about 30° C. to about 100° C. In some embodiments, the temperature above RT is from about 40° C. to about 60° C. In some embodiments, the temperature above RT is about 35, 40, 45, 50, 55, 60, 65, 70, 75, or 80° C.

In some embodiments, MH1 crystals can be prepared by the steps comprising:
(i) dissolving Compound 1 in a first solvent to get a solution;
(ii) adding a second solvent to get a mixture; and
(iii) filtering the mixture to obtain the crystalline solid MH1.

In some embodiments, the first solvent is selected from methylethyl ketone; 2-propanol; cumene; n-propyl acetate; isopropyl acetate; anisole; methylisobutyl ketone; n-heptane; 2-methyl tetrahydrofuran; and combinations thereof. In some embodiments, the second solvent is selected from methylethyl ketone; 2-propanol; n-propyl acetate; isopropyl acetate; anisole; methylisobutyl ketone; cumene; n-heptane; 2-methyl tetrahydrofuran; and combinations thereof. In some embodiments, the first solvent is 2-propanol. In some embodiments, the second solvent is n-heptane.

In some embodiments, the first solvent of step (i) further comprises water. In some embodiments, the first solvent of step (i) comprises 2-propanol and water. In some embodiments, the water content of the solution obtained in step (i) is about 1%, 2% or 3%. In some embodiments, the water content of the solution obtained in step (i) is about 1%. In some embodiments, the ratio (weight/weight) of water to 2-propanol is about 1:70.

In some embodiments, step (i) of the process is protected by nitrogen gas.

In some embodiments, step (i) is carried out at a temperature of about 25° C. to about 40° C. In some embodiments, step (i) is carried out at a temperature of about 27° C. to about 35° C.

In some embodiments, seed crystals are added after step (i) to induce the crystallization of MH1. In some embodiments, the temperature of the mixture is adjusted to from about 20° C. to about 30° C., before the seed crystals are added. In some embodiments, the temperature of the mixture is adjusted to from about 22° C. to about 28° C., before the seed crystals are added. The weight of the seed crystals is from about 0.05% to about 2%, of the weight of Compound 1 added in step (i). In some embodiments, the weight of the seed crystals is about 0.05, 1%, or 2%, of Compound 1 in step (i).

In some embodiments, steps (ii) and (iii) are each independently carried out at a temperature from about 20° C. to about 30° C., such as about 22° C. to about 28° C. In some embodiments, steps (ii) and (iii) are each independently carried out at a temperature from about 22° C. to about 28° C.

In some embodiments, the solid obtained in step (iii) is optionally washed one or more times with a solvent selected from methylethyl ketone; 1,4-dioxane; 2-propanol; acetone; cumene; n-propyl acetate; isopropyl acetate; anisole; methylisobutyl ketone; n-heptane; and 2-methyl tetrahydrofuran; and combinations thereof. In some embodiments, the solid obtained in step (iii) is optionally washed with n-heptane. In some embodiments, the solid obtained in step (iii) or after washing with n-heptane is pressed until dried. In some embodiments, the resulting dried solid is optionally subsequently dried under a flow of nitrogen gas. In some embodiments, the solid is further dried in a humidified environment, optionally under a flow of nitrogen gas. Different salt solutions, such as a saturated solution of sodium chloride, can provide a humidified environment with different relative humidity (RH). Commercially available equipment providing gas with adjustable RH and temperature may also be used.

In some embodiments, the anhydrous (AH) form of Compound 1 can be converted to MH1 when exposed to normal laboratory air (containing some moisture). In some embodiments, the anhydrous form of Compound 1 is left under ambient conditions (e.g. 25° C.) for at least about 12 hours, about 24 hours, about 36 hours, or about 48 hours.

In some embodiments, anhydrate (AH) or MH2 is made in a crystallization process. Drying and humidified drying of the anhydrate (AH) or MH2 then yields MH1 crystals.

Crystals of monohydrate form MH2 are prepared by the steps comprising:
(i) treating dry Compound 1 or MH1 with a first solvent system to get a suspension;
(ii) filtering the suspension to obtain the solid;
(iii) washing the solid one or more times with a second solvent; and
(iv) air drying the solid to obtain crystalline MH2, wherein the first solvent system is selected from water, ethyl acetate (EtOAc), and methyl acetate (MeOAc); and combinations thereof; and wherein the second solvent is selected from acetone; n-heptane; and 2-methyl tetrahydrofuran.

In some embodiments, the first solvent system is a mixture of water and ethyl acetate (EtOAc) or methyl acetate (MeOAc). In some embodiments, the first solvent system selected from 2% (v/v) EtOAc/water; 2.7% (v/v) EtOAc/water; or 7.5% (v/v) MeOAc/water. In some embodiments, the suspension is kept for about 4 days at about 5° C. or about 25° C.

In some embodiments, the second solvent is heptane.

In some embodiments, Compound 1 or MH1 of step (i) is dried in a vacuum oven. In some embodiments, Compound 1 or MH1 of step (i) is air dried.

In one embodiment, crystalline MH2 is prepared by treating Compound 1 or MH1 with a first solvent system comprising 7.5% (v/v) MeOAc/water at around 5° C., filtering the solid, and then air drying the solid.

In one embodiment, crystalline MH2 is prepared by:
(i) treating Compound 1 or MH1 with a first solvent system to obtain a suspension;
(ii) filtering the suspension to obtain the solid;
(iii) washing the solid with heptane; and
(iv) air drying to remove the solvent to get MH2;
wherein the solvent is a mixture of water and ethyl acetate (EtOAc) or methyl acetate (MeOAc), selected from 2% (v/v) EtOAc/water, 2.7% (v/v) EtOAc/water, and 7.5% (v/v) MeOAc/water.

IV. Methods of Using Polymorph Forms of Compound 1

PDE9 is expressed specifically in the human haematopoietic system including neutrophils, reticulocytes erythroid and erythroleukaemic cells. Furthermore, sickle cell disease (SCD) patients exhibit a marked and significant elevation of PDE9 expression in reticulocytes and neutrophils compared to healthy individuals (Almeida et al., Br J Haematol. 2008 September; 142(5):836-44). Evidence additionally demonstrates a link between PDE9 and cell adhesion since pharmacologic PDE9 inhibition ameliorates the increased adhesive properties of SCD neutrophils (Miguel et al., Inflamm Res. 2011 July; 60(7):633-42). The mechanism by which PDE9 inhibition decreases cell adhesion has been shown to be mediated by increased cGMP and decreased endothelial adhesion molecule expression. Importantly, in an animal model of SCD, the PDE9 inhibitor-mediated decrease in cell adhesion had the functional effect of increased cell survival. In addition to demonstrating decreased cell adhesion comparable to hydroxyurea (HU), PDE9 inhibition resulted in increased fetal non-sickled haemoglobin (HbF) production, which reduced the cellular concentration of abnormal haemoglobin (HbS) within red blood cells (RBCs) resulting in less polymerization of the abnormal haemoglobin and its associated sequelae. The importance of increasing HbF in treating SCD is evidenced by results of large studies like the Cooperative Study of Sickle Cell Disease, as well as studies in a variety of patient cohorts outside of the US, showing that HbF is among the most important modifiers of this disease (Alsultan et al., *Am J Hematol.*, 88(6):531-2 (2013)) as well as data showing that modifiers of HbF improve other hematological parameters (Akinsheye, *Blood*, 118(1):19-27 (2011)). Finally, Almeida and colleagues demonstrated that treatment with HU combined with PDE9 inhibition in a mouse model of SCD leads to an additional beneficial amplification of the cGMP elevating effects of HU (Almeida et al., Blood. 2012 Oct. 4; 120(14):2879-88). In conclusion, PDE9 inhibition can modulate both the expression of fetal haemoglobin production as well as decrease cell adhesion, both mechanisms key for the treatment of SCD.

One aspect of the present disclosure provides methods of using any of the polymorph forms of Compound 1 (such as monohydrate crystalline form MH1 or MH2) and pharmaceutical compositions comprising any of the polymorph forms of Compound 1 (such as monohydrate crystalline form MH1 or MH2).

The polymorph forms of Compound 1 (such as monohydrate crystalline form MH1 or MH2) may be used to treat sickle cell disease or any disease and/or symptom related to sickle cell disease, such as anemia, sickle-hemoglobin C disease (SC), beta thalassemia (beta-plus thalassemia and beta-zero thalassemia), vaso-occlusive crisis, attacks of pain (sickle cell crisis), splenic sequestration crisis, acute chest syndrome, aplastic crisis, hemolytic crisis, long-term pain, bacterial infections, and stroke.

In one embodiment, the polymorph forms of Compound 1 (such as monohydrate crystalline form MH1 or MH2) are used to treat beta thalassemia of a subject and/or to increase hemoglobin levels in the subject.

In another embodiment, the polymorph forms of Compound 1 (such as monohydrate crystalline form MH1 or MH2) are used to increase cGMP levels in a cell or in the plasma of a subject, wherein the subject has sickle cell disease. The cell may be, but not limited to, red blood cells and/or white blood cells. The cGMP level may be increased by at least 50%, 100%, or 150%. In some embodiments, the cGMP level is increased at least 2 times, 3 times, 4 times, 5 times, 10 times, 15 times, 20 times, or 25 times.

In another embodiment, the polymorph forms of Compound 1 (such as monohydrate crystalline form MH1 or MH2) are used to increase fetal hemoglobin (HbF) positive red blood cell number in a subject, wherein the subject has sickle cell disease. The HbF positive red blood cell number is increased by at least 50%, 100%, or 150%. In some embodiments, the HbF positive red blood cell number is increased at least 2 times, 3 times, 4 times, 5 times, 10 times, 15 times, 20 times, or 25 times.

In another embodiment, the polymorph forms of Compound 1 (such as monohydrate crystalline form MH1 or MH2) are used to reduce sickle red blood cell percentage (% sickle RBC), stasis percentage (% stasis), total bilirubin, or total leucocyte count in a subject, wherein the subject has sickle cell disease. The % sickle RBC, % stasis, total bilirubin, total leucocyte count or spleen weight is decreased by at least 10%, 20%, 30%, 40%, 50%, 60% or 70%.

cGMP level may be measured with any suitable method in the art, such as enzyme immunoassay.

HbF positive cells, as used herein, means red blood cells with HbF. HbF positive cells may be measured from a blood sample with any suitable method in the art, such as electrophoresis and/or colorimetric methods.

Sickle red blood cells, sickled red blood cells, as used herein, means red blood cells with a crescent or sickle shape. % sickle red blood cell may be measured from a blood sample with any suitable method in the art.

Stasis or microvascular stasis, as used herein, is serious slowing, or complete cessation, of blood or lymph flow through vessels. % stasis is the number of static (no flow) venules divided by the number of flowing venules times 100. % stasis may be measured with any suitable method in the art.

Total bilirubin, as used herein, means both unconjugated and conjugated bilirubin. Total bilirubin levels may be measured from a blood sample with any suitable method in the art.

Total leucocyte count or total white blood cell count, as used herein, is a blood test that measures the number of white blood cells in the body. It may be measured from a blood sample with any suitable method in the art.

Another aspect of the present disclosure provides methods of using the polymorph forms of Compound 1 (such as monohydrate crystalline form MH1 or MH2) in combination with at least one other active agent. They may be administered simultaneously or sequentially. They may be present as a mixture for simultaneous administration, or may each be present in separate containers for sequential administration.

The term "simultaneous administration", as used herein, is not specifically restricted and means that the polymorph forms of Compound 1 (such as monohydrate crystalline form MH1 or MH2) and the at least one other active agent are substantially administered at the same time, e.g. as a mixture or in immediate subsequent sequence.

The term "sequential administration", as used herein, is not specifically restricted and means that the polymorph forms of Compound 1 (such as monohydrate crystalline form MH1 or MH2) and the at least one other active agent are not administered at the same time but one after the other, or in groups, with a specific time interval between administrations. The time interval may be the same or different between the respective administrations of the polymorph forms of Compound 1 (such as monohydrate crystalline form MH1 or MH2) and the at least one other active agent and may be selected, for example, from the range of 2 minutes to 96 hours, 1 to 7 days or one, two or three weeks. Generally, the time interval between the administrations may be in the range of a few minutes to hours, such as in the range of 2 minutes to 72 hours, 30 minutes to 24 hours, or 1 to 12 hours. Further examples include time intervals in the range of 24 to 96 hours, 12 to 36 hours, 8 to 24 hours, and 6 to 12 hours.

The molar ratio of the polymorph forms of Compound 1 (such as monohydrate crystalline form MH1 or MH2) and the at least one other active agent is not particularly restricted. For example, when a polymorph form of Compound 1 (such as monohydrate crystalline form MH1 or MH2) and one other active agent are combined in a composition, the molar ratio of them may be in the range of 1:500 to 500:1, or of 1:100 to 100:1, or of 1:50 to 50:1, or of 1:20 to 20:1, or of 1:5 to 5:1, or 1:1. Similar molar ratios apply when a polymorph form of Compound 1 (such as monohydrate crystalline form MH1 or MH2) and two or more other active agent are combined in a composition. The polymorph form of Compound 1 (such as monohydrate crystalline form MH1 or MH2) may comprise a predetermined molar weight percentage from about 1% to 10%, or about 10% to about 20%, or about 20% to about 30%, or about 30% to 40%, or about 40% to 50%, or about 50% to 60%, or about 60% to 70%, or about 70% to 80%, or about 80% to 90%, or about 90% to 99% of the composition.

The other active agent may be a different PDE9 inhibitor of the present disclosure or HU. The other active agent may also be an antibiotic agent such as penicillin, a nonsteroidal anti-inflammatory drug (NSAIDS) such as diclofenac or naproxen, a pain relief medication such as opioid, or folic acid.

Yet another aspect of the present disclosure provides methods of using a polymorph form of Compound 1 (such as monohydrate crystalline form MH1 or MH2) in combination with at least one other therapy, such as but not limited to blood transfusion, bone marrow transplant, or gene therapy.

V. Kits and Devices

The disclosure provides a variety of kits and devices for conveniently and/or effectively carrying out methods of the present disclosure. Typically, kits will comprise sufficient amounts and/or numbers of components to allow a user to perform multiple treatments of a subject(s) and/or to perform multiple experiments.

In one embodiment, the present disclosure provides kits for treating sickle cell disease, comprising a polymorph form of Compound 1 (such as monohydrate crystalline form MH1 or MH2) or a combination of polymorph forms of Compound 1 (such as monohydrate crystalline form MH1 and MH2), optionally in combination with any other active agents, such as HU, an antibiotic agent such as penicillin, a nonsteroidal anti-inflammatory drug (NSAIDS) such as diclofenac or naproxen, a pain relief medication such as opioid, or folic acid.

The kit may further comprise packaging and instructions and/or a delivery agent to form a formulation composition. The delivery agent may comprise a saline, a buffered solution, or any delivery agent disclosed herein. The amount of each component may be varied to enable consistent, reproducible higher concentration saline or simple buffer formulations. The components may also be varied in order to increase the stability of PDE9 inhibitor compounds in the buffer solution over a period of time and/or under a variety of conditions.

The present disclosure provides for devices that may incorporate a polymorph form of Compound 1 (such as monohydrate crystalline form MH1 or MH2). These devices contain in a stable formulation available to be immediately delivered to a subject in need thereof, such as a human patient with sickle cell disease or beta thalassemia.

Non-limiting examples of the devices include a pump, a catheter, a needle, a transdermal patch, a pressurized olfactory delivery device, iontophoresis devices, multi-layered microfluidic devices. The devices may be employed to deliver a polymorph form of Compound 1 (such as monohydrate crystalline form MH1 or MH2) according to single, multi- or split-dosing regiments. The devices may be employed to deliver a polymorph form of Compound 1 (such as monohydrate crystalline form MH1 or MH2) across biological tissue, intradermal, subcutaneously, or intramuscularly. More examples of devices suitable for delivering a polymorph forms of compounds include but not limited to a medical device for intravesical drug delivery disclosed in International Publication WO 2014036555, a glass bottle made of type I glass disclosed in US Publication No. 20080108697, a drug-eluting device comprising a film made of a degradable polymer and an active agent as disclosed in US Publication No. 20140308336, an infusion device having an injection micropump, or a container containing a pharmaceutically stable preparation of an active agent as disclosed in U.S. Pat. No. 5,716,988, an implantable device comprising a reservoir and a channeled member in fluid communication with the reservoir as disclosed in International Publication WO 2015023557, a hollow-fibre-based biocompatible drug delivery device with one or more layers as disclosed in US Publication No. 20090220612, an implantable device for drug delivery including an elongated, flexible device having a housing defining a reservoir that contains a drug in solid or semi-solid form as disclosed in International Publication WO 2013170069, a bioresorbable implant device disclosed in U.S. Pat. No. 7,326,421, contents of each of which are incorporated herein by reference in their entirety.

VI. Definitions

The articles "a" and "an," as used herein, should be understood to mean "at least one," unless clearly indicated to the contrary.

The phrase "and/or," as used herein, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements).

As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements.

In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of," when used in the claims, shall have its ordinary meaning as used in the field of patent law.

As used herein, the phrase "at least one" in reference to a list of one or more elements should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, all transitional phrases such as "comprising," "including," "carrying," "having," "containing," "involving," "holding," and the like are to be understood to be open-ended, i.e., to mean including but not limited to.

Only the transitional phrases "consisting of" and "consisting essentially of" shall be closed or semi-closed transitional phrases, respectively, as set forth in the United States Patent Office Manual of Patent Examining Procedures.

As used herein, a "subject" or a "patient" refers to any mammal (e.g., a human), such as a mammal that may be susceptible to a disease or disorder, for example, tumorigenesis or cancer. Examples include a human, a non-human primate, a cow, a horse, a pig, a sheep, a goat, a dog, a cat, or a rodent such as a mouse, a rat, a hamster, or a guinea pig. In various embodiments, a subject refers to one that has been or will be the object of treatment, observation, or experiment. For example, a subject can be a subject diagnosed with cancer or otherwise known to have cancer or one selected for treatment, observation, or experiment on the basis of a known cancer in the subject.

As used herein, "process" and "method" can be used interchangeably.

As used herein, "treatment" or "treating" refers to amelioration of a disease or disorder, or at least one sign or symptom thereof "Treatment" or "treating" can refer to reducing the progression of a disease or disorder, as determined by, e.g., stabilization of at least one sign or symptom or a reduction in the rate of progression as determined by a reduction in the rate of progression of at least one sign or symptom. In another embodiment, "treatment" or "treating" refers to delaying the onset of a disease or disorder.

As used herein, "prevention" or "preventing" refers to a reduction of the risk of acquiring or having a sign or symptom a given disease or disorder, i.e., prophylactic treatment.

The phrase "therapeutically effective amount" as used herein means that amount of a compound, material, or composition comprising a compound of the present teachings that is effective for producing a desired therapeutic effect. Accordingly, a therapeutically effective amount treats or prevents a disease or a disorder, e.g., ameliorates at least one sign or symptom of the disorder. In various embodiments, the disease or disorder is a cancer.

A dash ("—") that is not between two letters or symbols is used to indicate a point of attachment for a substituent. For example, —$CONH_2$ is attached through the carbon atom (C).

By "optional" or "optionally," it is meant that the subsequently described event or circumstance may or may not occur, and that the description includes instances where the event or circumstance occurs and instances in which it does not. For example, "optionally substituted aryl" encompasses both "aryl" and "substituted aryl" as defined herein. It will be understood by those ordinarily skilled in the art, with respect to any group containing one or more substituents, that such groups are not intended to introduce any substitution or substitution patterns that are sterically impractical, synthetically non-feasible, and/or inherently unstable.

As used herein, the term "substantially" refers to the complete or nearly complete extent or degree of an action, characteristic, property, state, structure, item, or result. For example, an object that is "substantially the same" or "substantially in accordance with" a second object would mean that the object is either completely or nearly completely the same as the second object. The exact allowable degree of deviation from absolute completeness may in some cases depend on the specific context. However, generally speaking, the nearness of completion will be so as to have the same overall result as if absolute and total completion were obtained.

The use of "substantially" is equally applicable when used in a negative connotation to refer to the complete or near complete lack of an action, characteristic, property, state, structure, item, or result. For example, a composition that is "substantially free of" impurities would either completely lack impurities, or so nearly completely lack impurities that the effect would be the same as if it completely lacked impurities. In other words, a composition that is "substantially free of" an ingredient or element may still actually contain such item as long as there is no measurable effect thereof.

Unless otherwise specified, all numbers expressing quantities of ingredients, reaction conditions, and other properties or parameters used in the specification and claims are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques. For example, the term "about" can encompass variations of ±10%, ±5%, ±2%, ±1%, ±0.5%, or ±0.1% of the numerical value of the number, which the term "about" modifies. In various embodiments, the term "about" encompasses variations of ±5%, ±2%, ±1%, or ±0.5% of the numerical value of the number. In some embodiments, the term "about" encompasses variations of ±5%, ±2%, or ±1% of the numerical value of the number. In certain embodiments, the term "about" encompasses variations of ±5% of the numerical value of the number. In certain embodiments, the term "about" encompasses variations of ±2% of the numerical value of the number. In certain embodiments, the term "about" encompasses variations of ±1% of the numerical value of the number.

All numerical ranges herein include all numerical values and ranges of all numerical values within the recited range of numerical values. As a non-limiting example, ($C_1$-$C_6$) alkyls also include any one of $C_1$, $C_2$, $C_3$, $C_4$, $C_5$, $C_6$, ($C_1$-$C_2$), ($C_1$-$C_3$), ($C_1$-$C_4$), ($C_1$-$C_5$), ($C_2$-$C_3$), ($C_2$-$C_4$), ($C_2$-$C_5$), ($C_2$-$C_6$), ($C_3$-$C_4$), ($C_3$-$C_5$), ($C_3$-$C_6$), ($C_4$-$C_5$), ($C_4$-$C_6$), and ($C_5$-$C_6$) alkyls.

Further, while the numerical ranges and parameters setting forth the broad scope of the disclosure are approximations as discussed above, the numerical values set forth in the Examples section are reported as precisely as possible. It should be understood, however, that such numerical values inherently contain certain errors resulting from the measurement equipment and/or measurement technique.

EXAMPLES

It will be appreciated that the following examples are intended to illustrate but not to limit the present disclosure. Various other examples and modifications of the foregoing description and examples will be apparent to a person skilled in the art after reading the disclosure without departing from the spirit and scope of the disclosure, and it is intended that all such examples or modifications be included within the scope of the appended claims. All publications and patents referenced herein are hereby incorporated by reference in their entirety.

LIST OF ABBREVIATIONS $^1$H-NMR Proton Nuclear Magnetic Resonance
ATR Attenuated Total Reflectance
ca. Approximately
DMSO Dimethylsulfoxide
DSC Differential Scanning calorimetry
DVS Dynamic Vapour Sorption
EtOAc Ethyl acetate
EtOH Ethanol
FBRM Focussed Beam Reflectance Measurement
GVS Gravimetric Vapour Sorption
HPLC High Performance Liquid Chromatography
HSM Hot Stage Microscopy
ID Identification
IPA Propan-2-ol
IPrOAc Iso-Propyl Acetate
KF Karl Fischer
MeOH Methanol
MeOAc Methyl acetate
N/A Not Applicable
PLM Polarised Light Microscopy
RH Relative Humidity
RT Room Temperature
SCXRD Single Crystal X-Ray Diffraction
TFA Tri-Fluoro Acetic Acid
TGA Thermal Gravimetric Analysis
THF Tetrahydrofuran
Vol Volume
VT-XRPD Variable Temperature X-Ray Powder Diffraction
XRPD X-Ray Powder Diffraction Instrument and Methodology Details X-Ray Powder Diffraction (XRPD)

XRPD diffractograms were collected on a Bruker D8 diffractometer using Cu Kα radiation (40 kV, 40 mA) and a 0-20 goniometer fitted with a Ge monochromator. The incident beam passes through a 2.0 mm divergence slit followed by a 0.2 mm anti-scatter slit and knife edge. The diffracted beam passes through an 8.0 mm receiving slit with 2.5° Soller slits followed by the Lynxeye Detector. The software used for data collection and analysis was Diffrac Plus XRD Commander and Diffrac Plus EVA respectively.

Samples were run under ambient conditions as flat plate specimens using powder as received. The sample was prepared on a polished, zero-background (510) silicon wafer by gently pressing onto the flat surface or packed into a cut cavity. The sample was rotated in its own plane.

The details of the standard Pharmorphix data collection method are: Angular range: 2 to 42° 2θ; Step size: 0.05° 2θ; Collection time: 0.5 s/step (total collection time: 6.40 min).

PANalytical Empyrean

XRPD diffractograms were collected on a PANalytical Empyrean diffractometer using Cu Kα radiation (45 kV, 40 mA) in transmission geometry. A 0.5° slit, 4 mm mask and 0.04 rad Soller slits with a focusing mirror were used on the incident beam. A PI Xcel30 detector, placed on the diffracted beam, was fitted with a receiving slit and 0.04 rad Soller slits. The software used for data collect ion was X'Pert Data Collector using X'Pert Operator Interface. The data were analysed and presented using Diffrac Plus EVA or HighScore Plus.

Samples were prepared and analysed in either a metal or Millipore 96 well-plate in transmission mode. X-ray transparent film was used between the metal sheets on the metal well-plate and powders (approximately 1-2 mg) were used as received. The Millipore plate was used to isolate and analyse solids from suspensions by adding a small amount of suspension directly to the plate before filtration under a light vacuum.

The scan mode for the metal plate used the gonio scan axis, whereas a 20 scan was utilized for the Millipore plate.

The details of the standard screening data collection method are: Angular range: 2.5 to 32.0° 2θ; Step size: 0.0130° 2θ; Collection time: 12.75 s/step (total collection time of 2.07 min).

Non-Ambient Conditions

XRPD diffractograms were collected on a PANalytical Empyrean diffractometer using Cu Kα radiation (45 kV, 40 mA) in reflection geometry. The instrument is fitted with an Anton Paar CHC plus+ stage fitted with graphite/Kapton windows and equipped with air cooling and a low vacuum pump system using an Edwards RV3 pump. A programmable divergence slit (in automatic mode), with a 10 mm fixed incident beam mask, Ni filter and 0.04 rad Soller slits were used on the incident beam. A PIXcel$^{3D}$ detector, placed on the diffracted beam, was fitted with a programmable anti-scatter slit (in automatic mode) and 0.04 rad Soller slits.

The software used for data collection was X'Pert Data Collector and the data analysed and presented using Diffrac Plus EVA or Highscore Plus.

For variable temperature (VT) experiments the samples were prepared and analysed in an Anton Paar chromed sample holder. A heating/cooling rate of 10° C./min was used with a 2 min isothermal hold before the measurement started. The measurement parameters are as per the standard screening data collection method (detailed above). Measurements were taken at the following temperatures: 25, 50, 75, 100, 160, and 25° C. The sample was then reanalyzed by XRPD after 1 h to check for complete rehydration.

For vacuum experiments the samples were prepared and analysed in an Anton Paar chromed sample holder. The measurement parameters are as per the standard screening data collection method (detailed above), at 25° C. with no vacuum (I2). A vacuum of around 50 mbar was then applied and the sample measured every 5 min until the anhydrate pattern was obtained for three consecutive measurements (to ensure complete dehydration, up to sample 18). The vacuum was then released and the sample analysed every 5 min for 6 measurements (until sample 122). The sample was then reanalyzed by XRPD after 1 h to check for complete rehydration.

$^1$H-Nuclear Magnetic Resonance ($^1$H-NMR)

$^1$H NMR spectra were collected on a Bruker 400 MHz instrument equipped with an auto-sampler and controlled by a DRX400 console. Samples were prepared in DMSO-d6 solvent, unless otherwise stated. Automated experiments were acquired using ICON-NMR configuration within Topspin software, using standard Bruker-loaded experiments ($^1$H). Off-line analysis was performed using ACD Spectrus Processor.

Differential Scanning calorimetry (DSC)

DSC data were collected on a TA Instruments Discovery DSC equipped with a 50 position auto-sampler. Typically, 0.5-3 mg of each sample, in a pin-holed aluminum pan, was heated at 10° C./min from 25° C. to 300° C. A purge of dry nitrogen at 50 ml/min was maintained over the sample.

The instrument control software was TRIOS and the data were analysed using TRIOS or Universal Analysis.

Thermo-Gravimetric Analysis (TGA)

TGA data were collected on a TA Instruments Discovery TGA, equipped with a 25 position auto-sampler. Typically, 5-10 mg of each sample was loaded onto a pre-tared aluminum DSC pan and heated at 10° C./min from ambient temperature to 350° C. A nitrogen purge at 25 ml/min was maintained over the sample.

The instrument control software was TRIOS and the data were analysed using TRIOS or Universal Analysis.

Polarized Light Microscopy (PLM)

Samples were studied on a Nikon SMZ1500 polarized light microscope with a digital video camera connected to a DS Camera control unit DS-L2 for image capture. The sample was viewed with appropriate magnification and partially polarized light, coupled to a λ false-color filter.

Hot Stage Microscopy (HSM)

Hot Stage Microscopy was carried out using a Leica LM/DM polarized light microscope combined with a Mettler-Toledo FP82HT hot-stage and a digital video camera for image capture. A small amount of each sample was placed onto a glass slide with individual particles separated as well as possible. The sample was viewed with appropriate magnification and partially polarized light, coupled to a λ false-color filter, whilst being heated under ambient temperature, typically at 10-20° C./min. Data was collected using StudioCapture.

Gravimetric Vapour Sorption (GVS)

Sorption isotherms were obtained using a SMS DVS Intrinsic moisture sorption analyzer, controlled by DVS Intrinsic Control software. The sample temperature was maintained at 25° C. by the instrument controls. The humidity was controlled by mixing streams of dry and wet nitrogen, with a total flow rate of 200 ml/min. The relative humidity was measured by a calibrated Rotronic probe (dynamic range of 1.0-100% RH), located near the sample. The weight change, (mass relaxation) of the sample as a function of % RH was constantly monitored by a microbalance (accuracy ±0.005 mg).

Typically, 5-30 mg of sample was placed in a tared mesh stainless steel basket under ambient conditions. The sample was loaded and unloaded at 40% RH and 25° C. (typical room conditions). A moisture sorption isotherm was performed as outlined below (2 scans per complete cycle). The standard isotherm was performed at 25° C. at 10% RH intervals over a 0-90% RH range. Typically, a double cycle (4 scans) was carried out. Data analysis was carried out within Microsoft Excel using the DVS Analysis Suite.

TABLE 2

Method for SMS DVS intrinsic experiments.

| Parameter | Value |
| --- | --- |
| Adsorption - Scan 1 | 40-90 |
| Desorption, Adsorption -Scan 2 | 90-0, 0-40 |
| Intervals (% RH) | 10 |
| Number of Scans | 4 |
| Flow rate (ml/min) | 200 |
| Temperature (° C.) | 25 |
| Stability (° C./min) | 0.2 |
| Sorption Time (hours) | 6 hour time out |
| Number of cycles | 2 |

The sample was recovered after completion of the isotherm and re-analyzed by XRPD.

Chemical Purity Determination by HPLC

Purity analysis was performed on an Agilent HP1100 series system equipped with a diode array detector and using ChemStation software. The full method details are provided below in Table 3.

TABLE 3

HPLC method for chemical purity determination.

| Parameter | Value |
| --- | --- |
| Type of method | Reverse phase with gradient elution |
| Sample Preparation | 0.5 mg/ml in acetonitrile:water 1:1 |
| Column | Supelco Ascentis Express C18, 100 × 4.6 mm, 2.7 μm |
| Column Temperature (° C.) | 25 |
| Injection (μL) | 5 |
| Wavelength Bandwidth (nm) | 255, 90 |

TABLE 3-continued

HPLC method for chemical purity determination.

| Parameter | Value | |
|---|---|---|
| Flow Rate (ml/min) | 2 | |
| Phase A | 0.1% TFA in water | |
| Phase B | 0.085% TFA in acetonitrile | |

| Timetable | Time (min) | % Phase A | % Phase B |
|---|---|---|---|
| | 0 | 95 | 5 |
| | 6 | 5 | 95 |
| | 6.2 | 95 | 5 |
| | 8 | 95 | 5 |

Water Determination by Karl Fischer Titration (KF)

The water content of each sample was measured on a Metrohm 874 Oven Sample Processor at 1.50° C. with 851 Titrano Coulometer using Hydranal Coulomat AG oven reagent and nitrogen purge. Weighed solid samples were introduced into a sealed sample vial. Approximately 10 mg of sample was used per titration and duplicate determinations were made. An average of these results is presented unless otherwise stated. Data collection and analysis were performed using Tiamo software.

Thermodynamic Aqueous Solubility

Aqueous solubility was determined by suspending sufficient compound in relevant media to give a maximum final concentration of ≥200 mg/ml of the parent freeform of the compound. The suspension was equilibrated at 25° C., on a Heidolph plate shaker set to 750 rpm for 24 hours. The pH of the saturated solution was then measured and the suspension filtered through a glass fibre C filter (particle retention 1.2 μm) and diluted appropriately. Quantitation was by HPLC with reference to a standard solution of approximately 0.15 mg/ml in DMSO. Different volumes of the standard, diluted and undiluted sample solutions were injected.

The solubility was calculated using the peak areas determined by integration of the peak found at the same retention time as the principal peak in the standard injection.

TABLE 4

HPLC method for solubility measurements.

| Parameter | Value | |
|---|---|---|
| Type of method | Reverse phase with gradient elution | |
| Column | Phenomenex Luna, C18 (2) 5 μm 50 × 4.6 mm | |
| Column Temperature (° C.) | 25 | |
| Standard Injections (μl) | 1, 2, 3 4, 5, 7 | |
| Test Injections (μl) | 1, 2, 3, 10, 15, 20 | |
| Detection: Wavelength, Bandwidth (nm) | 260, 90 | |
| Flow Rate (ml/min) | 2 | |
| Phase A | 0.1% TFA in water | |
| Phase B | 0.085% TFA in acetonitrile | |

| Timetable | Time (min) | % Phase A | % Phase B |
|---|---|---|---|
| | 0 | 95 | 5 |
| | 1 | 80 | 20 |
| | 2.3 | 5 | 95 |
| | 3.3 | 5 | 95 |
| | 3.5 | 95 | 5 |
| | 4.4 | 95 | 5 |

Analysis was performed on an Agilent HP1100 series system equipped with a diode array detector and using ChemStation software.

Raman Spectroscopy

Data were collected on a Renishaw inVia Qontor. Instrument control, data analysis and presentation software was WiRE.

Method: excitation source, $\lambda ex=633$ nm or 785 nm laser, attenuated appropriately to avoid sample degradation. Raman shift range: 100-5000 $cm^{-1}$. Exposure time: 0.02-10 s. Accumulations: 1-3. Alternatively, Raman shift range: 180-1700 $cm^{-1}$. Exposure time: 30 s. Accumulations: 3.

Crystal 16

A Crystal 16 crystallization system (Technobis, NL) was used to determine the solubility and metastable zone of the material as a function of temperature.

Slurries of the API, in different overall concentrations/ were prepared by adding a known amount of solid to a known amount of chilled solvent (between 0.5 and 1.5 ml) and stirred at 400 rpm using a magnetic bar. The saturation temperature was measured through cycles of heating and cooling from −8 to 70° C. at 0.5° C./min.

Upon increasing the temperature/the solid completely dissolved and the suspension became a clear solution such that the light transmission reached its maximum value. This temperature is assigned as the clear point/which was assumed to coincide with the saturation temperature. Then by cooling the solution at a rate of 0.5° C./min, the temperature at which particles first formed was detected by a decrease in the light transmission. This is assigned as the cloud point. The points were fitted by a Van't Hoff equation and the difference between the cloud and the clear points defined the metastable zone width (MSZW) of the system. The instrument control software was Crystallization Systems and the data were analysed using Crystal Clear and Microsoft Excel.

Focused Beam Reflectance Measurement (FBRM)

Particle size distribution was collected using an FBRM probe G400 by collecting data every 10 seconds. Data was processed with iC FBRM SP1 software.

Single Crystal X-Ray Diffraction (SCXRD)

Data were collected on a Rigaku Oxford Diffraction Supernova Dual Source, Cu at Zero, Atlas CCD diffractometer equipped with an Oxford Cryosystems Cobra cooling device. The data were collected using Cu Kα or Mo Kα radiation as stated in the experimental tables. Structures were solved and refined using the Bruker AXS SHELXTL suite or the OLEX2 crystallographic software. Full details can be found in the CIF. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter. A reference diffractogram for the crystal structure was generated using Mercury.

Example 1. Synthesis of Compound 1

Compound 1 is an enantiomer of 6-[4-methyl-1-(pyrimidin-2-ylmethyl)pyrrolidin-3-yl]-3-tetrahydropyran-4-yl-7H-imidazo[1,5-a]pyrazin-8-one disclosed in WO 2013/053690. Compound 1 may be prepared from chiral-selective purification from 6-[4-methyl-1-(pyrimidin-2-ylmethyl)pyrrolidin-3-yl]-3-tetrahydropyran-4-yl-7H-imidazo[1,5-a]pyrazin-8-one prepared according to the method disclosed in WO 2013/053690, the contents of which are incorporated herein by reference in their entirety. Compound 1 may also be prepared with the method disclosed in WO 2017/005786, the contents of which are incorporated herein by reference in their entirety.

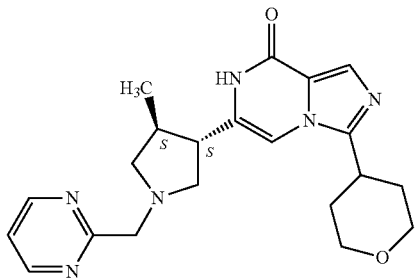

Example 2. Crystal Structure Determination and Characterization of MH1

Single Crystal Growth Experiments

Crystallization can be obtained by lowering the temperature of a clear solution. The solubility of most materials decreases with temperature, and hence, cooling can be used to cause supersaturation. Solvents used in this study were Isopropyl Acetate; Ethanol; Tetrahydrofuran; Water; Dichloromethane; Acetonitrile; Anisole; Methylisobutyl Ketone; Nitromethane; 1,2-Dimethoxyethane; Methylethyl Ketone; 1,4-Dioxane; n-Propyl Acetate; 2-Propanol; Acetone; Cumene; N,N-Dimethylformamide; Dimethyl Sulfoxide; Methanol; 2-Methyl Tetrahydrofuran; MeCN/5% water; IPA/5% water; EtOH/water 1:1; and THF/10% water.

5.0 mg MH1 (off-white powder) was weighed into 24 HPLC vials and treated with various solvents (50 µl) at room temperature (RT). The sample was then placed at 50° C. for 5 minutes. Any solutions obtained at RT or 50° C. were placed in a refrigerator at 4° C. A further aliquot of solvent (100 µl) was added to any suspensions and these were then placed at (50° C.) for 1 hour. Any remaining suspensions were then filtered by syringe and the mother liquors placed in the fridge at 4° C. Any solutions obtained after the addition of solvent after 1 hour were also placed in a refrigerator.

Crystals suitable for analysis were only obtained initially on cooling from isopropyl acetate, anisole, methylisobutyl ketone, n-propyl acetate, cumene and 2-methyl THF. A crystal of sufficient size and quality for analysis by single crystal X-ray diffraction was isolated with approximate dimensions 0.40×0.15×0.08 mm obtained by cooling the mother liquor from a saturated solution of the compound in n-propyl acetate.

The crystal structure of MH1 was determined at 293 and 100 K. The crystals are orthorhombic, space group $P2_12_12_1$ with the final $R1=[I>2\sigma (I)]=4.25$ and 3.46% respectively and the Flack parameter=0.02(8) and −0.05(7) at 293 K and 100 K respectively. The absolute stereochemistry of the compound has been determined as (S, S). The compound was identified as depicted in FIG. 1. There is one molecule of Compound 1 and one molecule of water in the asymmetric unit, both fully ordered. XRPD patterns were calculated from the crystal structures and compared to the experimental diffractogram for the material as received at room temperature. An overlay of the experimental diffractogram at room temperature (FIG. 2B) and the simulated XRPD patterns for MH1 at 293 K and 100 K shows they are consistent. Any slight differences are attributable to lattice variations with temperature and preferred orientation.

A summary of the characterization data for MH1 is in Table 5.

TABLE 5

Characterization data for MH1.

Figure 4:
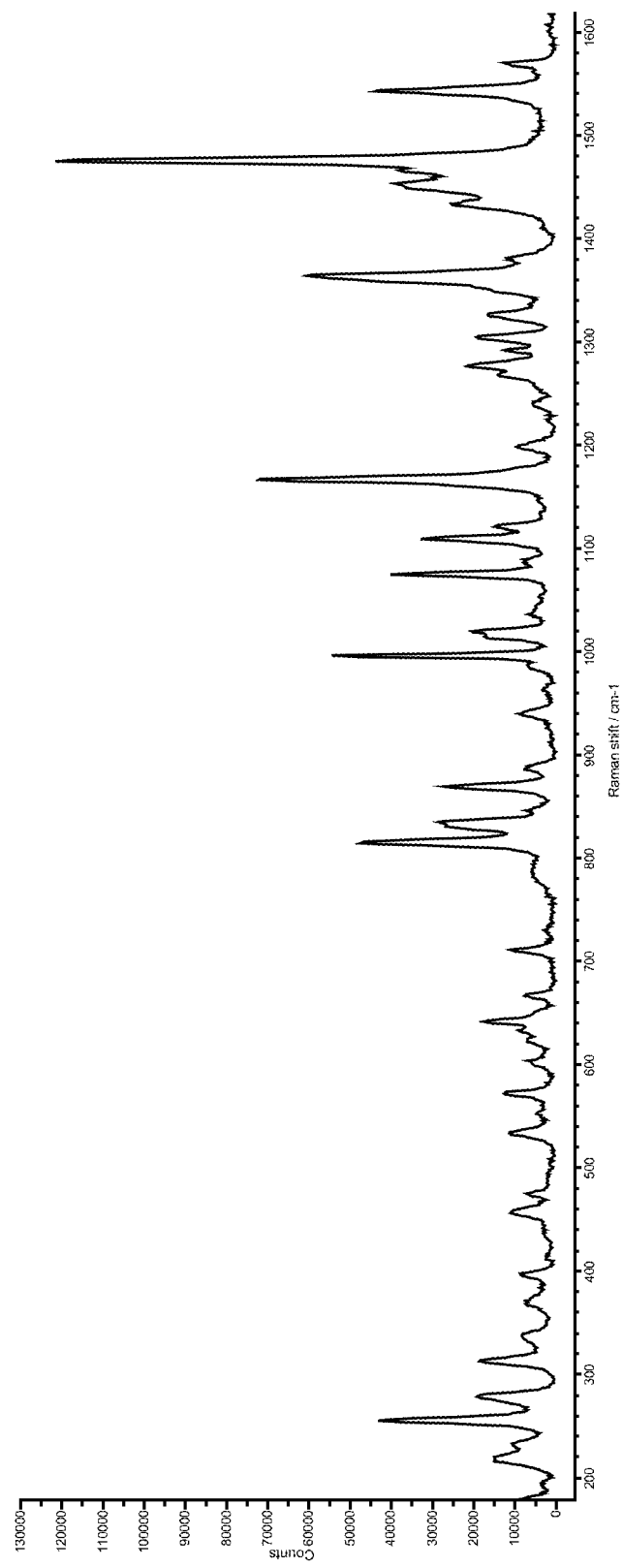
FIG. 4 is the Raman spectrum of MH1.

| Technique | Characterization |
| --- | --- |
| XRPD | Crystalline MH1 (FIG. 2A) |
| 1H-NMR | Consistent with structure |
| TGA | 3.8% w/w mass loss ambient - 90° C. |
|  | 0.1% w/w loss at the melting point. (FIG. 5) |
| DSC | Broad endotherm from 40-100° C. (73 J/g) |
|  | Large endotherm onset 184.4° C. (68 J/g) (FIG. 5) |
| Purity by HPLC | 99.4% |
| KF | 2.7% |
| GVS | Max uptake of 4.7%, no hysteresis, large step between 1020% RH |
| FTIR | Collected as reference (FIG. 3; Table 6) |
| Raman | Collected as reference (785 nm) (FIG. 4; Table 7) |

TABLE 6

FTIR peak table for MH1.

| $cm^{-1}$ | % T | Intensity |
| --- | --- | --- |
| 668 | 92.3 | M |
| 712 | 93.6 | W |
| 746 | 90.5 | M |
| 782 | 88.7 | S |
| 808 | 89.631 | M |
| 816 | 89.127 | M |
| 836 | 94.18 | W |
| 845 | 93.857 | W |
| 870 | 94.546 | W |
| 888 | 90.823 | M |
| 913 | 95.345 | W |
| 927 | 93.207 | M |
| 943 | 93.438 | W |
| 964 | 93.947 | W |
| 987 | 90.082 | M |
| 996 | 94.0 | W |
| 1004 | 94.2 | W |
| 1014 | 93.6 | W |
| 1021 | 94.7 | W |
| 1046 | 95.0 | W |
| 1055 | 94.1 | W |
| 1085 | 90.1 | M |
| 1110 | 92.8 | M |
| 1123 | 88.6 | S |
| 1136 | 93.8 | W |
| 1148 | 93.7 | W |
| 1161 | 92.2 | M |
| 1167 | 92.4 | M |
| 1199 | 95.0 | W |
| 1241 | 92.9 | M |
| 1257 | 94.0 | W |
| 1265 | 94.0 | W |
| 1284 | 93.6 | W |
| 1292 | 94.4 | W |
| 1303 | 93.2 | M |
| 1324 | 91.4 | M |
| 1333 | 92.4 | M |
| 1351 | 90.6 | M |
| 1361 | 90.2 | M |
| 1381 | 93.7 | W |
| 1390 | 94.2 | W |
| 1413 | 90.7 | M |
| 1433 | 90.7 | M |
| 1452 | 92.3 | M |
| 1465 | 94.6 | W |
| 1476 | 93.9 | W |
| 1544 | 93.5 | W |

TABLE 6-continued

FTIR peak table for MH1.

| cm$^{-1}$ | % T | Intensity |
|---|---|---|
| 1562 | 87.8 | S |
| 1604 | 94.7 | W |
| 1655 | 82.8 | VS |
| 2807 | 94.8 | W |
| 2852 | 95.6 | W |
| 2870 | 95.9 | W |
| 2917 | 95.0 | W |
| 2955 | 94.3 | W |
| 2963 | 94.6 | W |
| 3078 | 95.2 | W |
| 3107 | 95.3 | W |
| 3431 | 96.4 | W |
| 3537 | 96.5 | VW |

Key:
W—weak,
M—medium,
S—strong,
VS—very strong

TABLE 7

Raman peak table for MH1.

| Band centre/cm$^{-1}$ | Absolute intensity/a · u |
|---|---|
| 217.3 | 12597 |
| 233.9 | 8008 |
| 256.0 | 41662 |
| 279.6 | 17895 |
| 313.9 | 18410 |
| 339.5 | 8409 |
| 369.4 | 8047 |
| 398.1 | 9543 |
| 457.7 | 11219 |
| 476.0 | 7098 |
| 534.7 | 10630 |
| 554.2 | 3744 |
| 573.5 | 11517 |
| 605.1 | 5479 |
| 623.8 | 5852 |
| 634.2 | 7887 |
| 642.9 | 16466 |
| 668.3 | 6531 |
| 712.2 | 10035 |
| 790.6 | 5200 |
| 816.4 | 47312 |
| 836.4 | 27888 |
| 847.5 | 6629 |
| 870.6 | 26632 |
| 887.4 | 6800 |
| 941.0 | 7904 |
| 997.6 | 53279 |
| 988.7 | 5529 |
| 1021.0 | 19238 |
| 1037.5 | 5146 |
| 1076.4 | 38792 |
| 1090.8 | 6061 |
| 1111.0 | 31567 |
| 1123.1 | 13450 |
| 1168.5 | 72312 |
| 1199.9 | 8600 |
| 1240.0 | 4881 |
| 1269.5 | 13599 |
| 1278.5 | 21228 |
| 1293.7 | 12122 |
| 1306.7 | 18711 |
| 1327.8 | 16145 |
| 1366.0 | 60204 |
| 1383.4 | 10783 |
| 1434.8 | 23876 |
| 1455.0 | 37645 |
| 1477.3 | 120271 |
| 1545.1 | 42516 |
| 1571.9 | 11241 |

Example 3. Crystal Structure Determination of MH2 of Compound 1

Single Crystal Growth Experiments

The supplied MH1 (1.6 g) was placed in a vacuum oven at 50° C. for 3 h. The sample was then treated with 7.5% Water/MeOAc (10 vol, 16 ml) at 5° C. After 12 h at 5° C., the suspension was filtered, washed with heptane and air dried.

Crystals suitable for analysis were obtained after washing the vial with n-heptane during the filtration procedure. These crystals were used to determine the single crystal structure at 100 K.

| Crystallisation Method | Form |
|---|---|
| Fast evaporation (heptane wash) | MH2 |

Crystal Structure of MH2

Crystals of MH2 were obtained by fast evaporation when washing with heptane. A crystal of sufficient size and quality for analysis by single crystal X-ray diffraction was isolated with approximate dimensions 0.65×0.26×0.18 mm. The crystal structure of MH2 was determined at 100 K. The crystals are orthorhombic, space group $P2_12_12_1$ with the final $R_1=[I>2\sigma(I)]=3.07$ The compound was identified as depicted in HG. 5. The asymmetric unit contains one molecule of Compound 1 and one molecule of water, both fully ordered. The absolute configuration of MH2 has been determined with C7 and C9 in the (S,S) configuration, with the Flack parameter=−0.01(8).

Figure 7A:
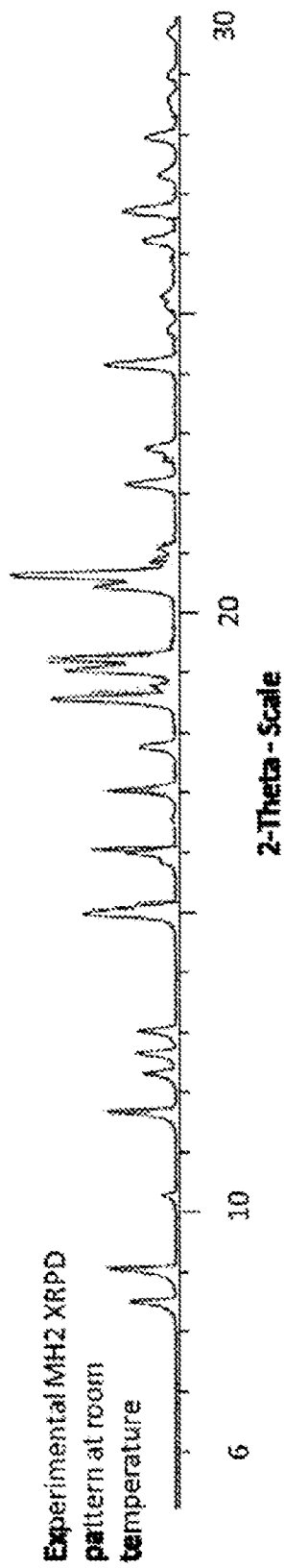
FIG. 7A is the experimental XRPD pattern of MH2 at room temperature.
Figure 7B:
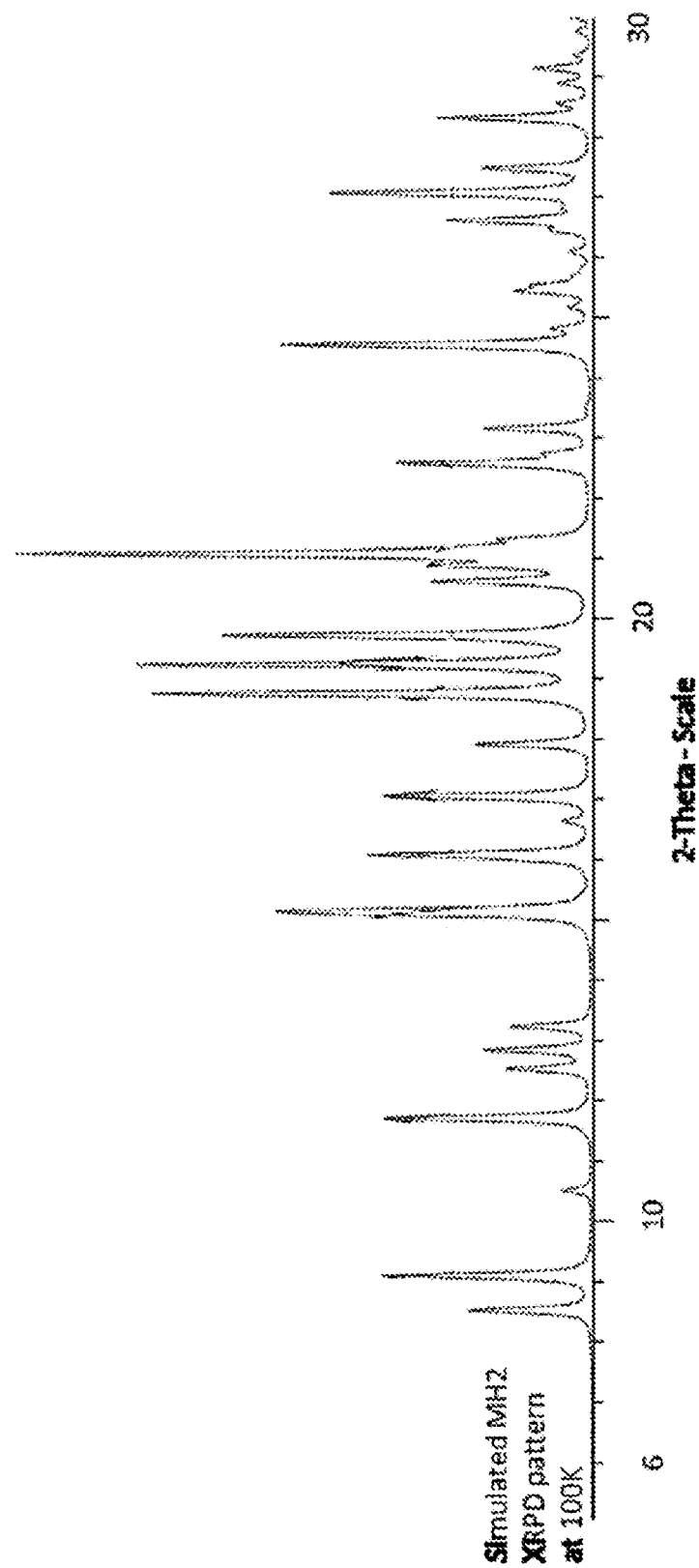
FIG. 7B is the simulated XRPD pattern of MH2 at 100 K.

An XRPD pattern was calculated from the crystal structure and compared to the experimental diffractogram of the MH2 material at room temperature (FIG. 7). The simulated diffractogram was generally consistent with the bulk material. Any slight differences are mostly likely attributable to lattice variations with temperature and preferred orientation.

Example 4. Transformations Between Anhydrous (AH) and Hydrated Forms (MH1 and MH2)

Dehydration Investigations of MH1

MH1 was initially placed in a vacuum oven at 50° C. overnight. The sample was then returned to the vacuum oven and stored for 5 days at 50° C. and then for 4 hours at 90° C. An aliquot was then removed from storage at 90° C. and held at ambient conditions for 2 hours. At each time point, analysis by TGA was undertaken.

A weight loss attributed to water was observed in all samples post drying. This is due to the sample either not losing the water completely at the temperatures investigated or reabsorbing water at ambient conditions. To determine the impact of vacuum and heating on the crystalline form further XRPD investigations were performed.

VT XRPD

MH1 was analysed at 25, 50, 75, 100, 160 and 25° C. (10° C./min heating rate and a 2 min wait before the measurement started) on the Empyrean. The sample was then reanalysed by XRPD after 10 and 20 min to check for rehydration.

Initially the sample is MH1. As the temperature is increased, the sample converts to the anhydrate form and by 75° C. it is fully anhydrous by XRPD. Upon re-cooling to 25° C., peaks corresponding to MH1 are present. Upon further standing at 25° C. these peaks become more intense as those corresponding to the anhydrate become less intense. This indicates that under ambient conditions, the anhydrate readily converts to MH1. TGA post VT XRPD gives 3.2% mass loss, confirming re-uptake of water.

XRPD Under Vacuum

MH1 was analysed at 25° C. with no vacuum. A vacuum of around 50 mbar was then applied and the sample measured every 5 min until the anhydrate pattern was obtained for three consecutive measurements (to ensure complete dehydration). The vacuum was then released and the sample analysed every 5 min for 6 measurements before the front of the sample stage was removed.

Initially, the sample is MH1, as the sample is stored under vacuum the sample converts to the anhydrate form (after 10 min it is fully anhydrous by XRPD). Upon releasing the vacuum, no change is initially seen for 30 min. The front of the sample stage is then taken off to allow the ambient air to penetrate the sample stage. Peaks corresponding to MH1 immediately appear and the sample is fully hydrated by XRPD after 15 min. This indicates that under ambient conditions, the anhydrate readily converts to MH1. TGA post vacuum XRPD gives 3.4% mass loss.

The results of the drying investigations confirm that although it is possible to obtain the anhydrous form, this material quickly converts back to the monohydrate, MH1. Compression studies on MH1 showed no conversion to the anhydrate by XRPD.

Water Activity Experiments for MH1

MH1 (30.0 mg) was weighed into HPLC vials and placed in a vacuum oven to dry over the weekend. All samples were then placed in a desiccator prior to use to ensure dryness. Solvent (300 µl) was added and slurries agitated at either 25° C. or 5° C. Further MH1 was added to any solutions formed to return to a slurry. Ethyl acetate and methyl acetate were both dried prior to use. After four days, the samples were analysed by XRPD with minimum exposure to ambient conditions.

Selected samples were also characterised after standing at ambient for 2 days by XRPD, 1H NMR, TGA and DSC.

The results obtained from the water activity experiments show at water activity of $a_w \leq 0.4$ the monohydrate MH1 was obtained. At $a_w = 0.5$ and 0.6 at 25° C. the monohydrate MH1 was also obtained. However, a new form was observed at 5° C. This form was then observed at both 5 and 25° C. at $a_w = 0.7$-0.9. Re-analysis of selected samples of this form after two days at ambient conditions confirmed they remained the same form. The new form is also a monohydrate form and has been identified as MH2.

TABLE 8

Results of Water Activity Experiments.

| Solvent | Water activity | Results for 5° C. | Results for 25° C. |
|---|---|---|---|
| EtOAc | Sieves | MH1 | MH1 |
| 0.5% water/EtOAc | Aw = 0.3 | MH1 | MH1 |
| 0.8% water/MeOAc | Aw = 0.4 | MH1 | MH1 |
| 1% water/EtOAc | Aw = 0.5 | New Form | MH1 |
| 1.5% water/EtOAc | Aw = 0.6 | New Form | MH1 |
| 2% water/EtOAc | Aw = 0.7 | New Form | New Form |
| 2.7% water/EtOAc | Aw = 0.8 | New Form | New Form |
| 7.5% water/MeOAc | Aw = 0.9 | New Form | New Form |

Scale Up of MH2

MH 1 (1.6 g) was placed in a vacuum oven at 50° C. for 3 h. The sample was then treated with 7.5% Water/MeOAc (10 Vol, 16 ml) at 5° C. After 12 h at 5° C., an aliquot of the sample was, analysed by XRPD. The suspension was then filtered, washed with heptane, air dried and analysed by XRPD and the appropriate techniques. Washing the vial with heptane caused crystals to form on the wall of the vial which were analysed by SCXRD. A summary of the characterization results is shown in Table 9.

Figure 8:
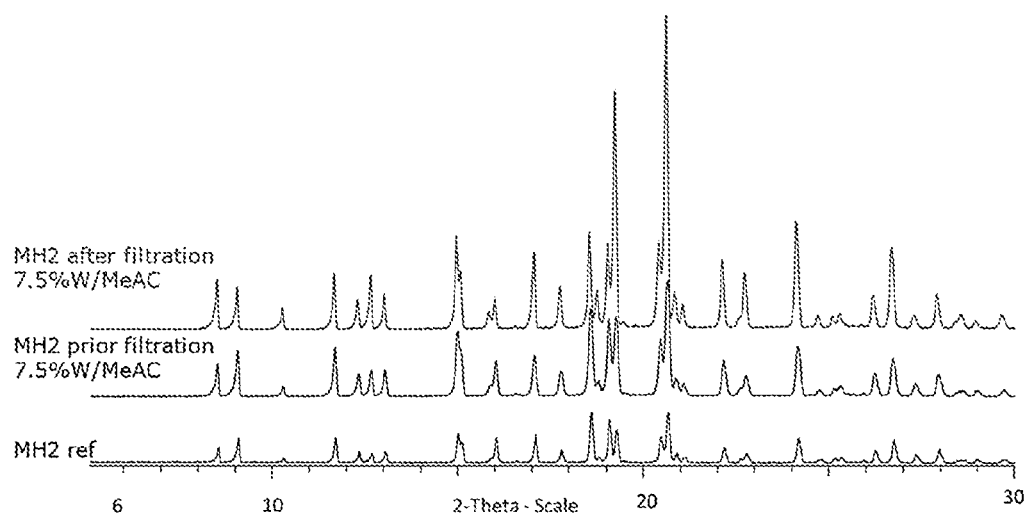
FIG. 8 is an XRPD overlay of the scale up of MH2.

Results and discussion: Attempts to prepare MH2 were successful. XRPD overlay of the scale up of MH2 is shown in FIG. 8. The TGA data revealed a 4.4% mass loss between 25 and 100° C. corresponding to 1 equivalent (eq) of water, indicating that the sample is a monohydrate. This was confirmed by the KF measurement with 4.5% water detected in the sample. The water loss was also noted in the DSC data with a broad endotherm at 59.1° C. followed by an endotherm indicative of melting at 184.7° C. This endotherm corresponds to the melt of the AH and is very close in value with the melting point obtained when starting from MH1 (185.6° C.). The $^1$H-NMR spectrum is consistent with the structure as well as the reference spectrum of MH1. GVS data showed a lack of uptake in the first sorption cycle from 40 to 90% RH. This was followed by 4.8% weight loss in the desorption cycle. An uptake of 4.5% was observed in the second sorption cycle. This suggested that MH2 transformed into AH during the desorption cycle followed by conversion to a monohydrate during the sorption cycle. The transformation was confirmed by the post-GVS XRPD analysis, which indicated that it had rehydrated as MH1. The Raman spectra of MH1 and MH2 contain similar features with the main differences at 1350 and 1650 cm-1. This is expected, as any differences in Raman spectra between polymorphs are often minor. The stereochemistry of MH2 was determined by SCXRD as the S,S-enantiomer (same as MH1). PLM shows that the morphology of the sample is crystalline plates mixed with irregular shapes. The thermodynamic solubility in water of MH2 at 25° C. is 36.5 mg/ml

TABLE 9

Characterization data for MH2.

| | |
|---|---|
| XRPD | Crystalline form - Matches Monohydrate Form 2 (MH2) |
| Purity HPLC | 99.3% |
| $^1$H-NMR | Consistent with reference spectrum |
| DSC | Broad endotherm at 59.1° C. followed by sharp endotherm corresponding to melting at 184.7° C. |
| TGA | 4.4% w/w between 25-100° C. |
| KF | 4.5% water detected |
| GVS | First sorption cycle from 40 to 90% RH, no uptake. Followed by 4.8% weight loss in the desorption cycle. Second sorption cycle, uptake of 4.5%. |

TABLE 9-continued

Characterization data for MH2.

| | |
|---|---|
| XRPD post-GVS | Crystalline - Matches MH1 |
| PLM | Crystalline plates and irregular shapes |
| Thermodynamic Solubility in water | 36.5 mg/ml (25° C.) |
| Raman | Similar spectrum between MH1 and MH2 with main differences observed at 1350 and 1650 cm$^{-1}$ |
| SCXRD | Monohydrate S,S-enantiomer (different to MH1) |

Further Analysis of MH1 and MH2

Example 5. XRPD Investigation of MH2

Procedure: A second batch of MH2 material was prepared using the same procedure. This sample was then analysed by VTXRPD and by XRPD under vacuum.

Results and discussion: MH2 converts to AH (anhydrate) upon heating. A mixture of MH2 and AH was formed at 50° C. followed by a complete conversion to AH at 75° C. After cooling back to 25° C. the AH has completely transformed into MH1. The MH1 formation was confirmed by XRPD after 1 h storage at ambient conditions.

The MH2 sample dehydrated into AH after 5 minutes exposure to vacuum. After 15 minutes the vacuum was released. XRPD data were collected for 55 minutes and the final pattern collected was a mixture of AH and MH1. The sample was reanalyzed after 1 h and a complete rehydration to MH 1 was observed.

Example 6. Drying Investigation of the Two Hydrates (MH1 and MH2)

Procedure: MH1 and MH2 were placed in a vacuum oven at 50° C. and RT for 24 h. The samples were then analysed by TGA and XRPD immediately after removal and after 4 hours standing under ambient conditions.

Results and discussion: The samples were analyzed by XRPD and TGA immediately after they were removed from the oven (T=0) and then remeasured after 4 h (T=4 h). At T=0 both MH1 and MH2 (dried at RT and 50° C.) converted to a mixture of MH1 and AH by XRPD. A small amount of water loss was recorded by TGA for both samples. This indicates that both hydrates were converted to AH during vacuum oven drying. After 4 h at ambient conditions the XRPD data show a full conversion of both samples into MH1. However, the TGA data indicated that the rehydration is not fully complete with only ~1.8-2.7% water lost. Based on these results, it appears that MH2 converts into AH during drying, followed by a conversion to MH1 at ambient storage.

TABLE 10

Drying investigation of MH1 and MH2.

| Compound | MH 1 | MH2 |
|---|---|---|
| XRPD (T = 0, RT) | Matches MH1 and AH | Matches MH1 and AH |
| TGA (T = 0, RT) | 0.3% w/w lost between 25 and 100° C. | 0.2% w/w lost between 25 and 100° C. |
| XRPD (T = 0, 50° C.) | Matches MH1 and AH | Matches MH1 and AH |
| TGA (T = 0, 50° C.) | 0.3% w/w lost between 25 and 100° C. | 0.6% w/w lost between 25 and 100° C. |
| XRPD (T = 4 h, RT) | Matches MH1 | Matches MH1 |
| TGA (T = 4 h, RT) | 1.8% w/w lost between 25 and 100° C. | 1.9% w/w lost between 25 and 100° C. |
| XRPD (T = 4 h, 50° C.) | Matches MH1 | Matches MH1 |
| TGA (T = 4 h, 50° C.) | 2.7% w/w lost between 25 and 100° C. | 1.9% w/w lost between 25 and 100° C. |

Example 7. Stability Studies with Competitive Slurries of the Two Hydrates (MH1 and MH2)

Procedure: Saturated solutions of the supplied MH 1 (J08343) were prepared in different solvents/systems (1 ml). The saturated solutions were then filtered and used for competitive slurry experiments.

MH1 and MH2 (ca. 15 mg each) were physically mixed before they were treated with the filtered saturated solutions (300 μL). The samples were stirred at 25° C. for 24 h then filtered, air dried and analysed by XRPD.

The same solvents were used as for samples in water activity experiments with additional IPA/heptane mixtures as this is the current crystallisation solvent. This procedure was also followed for IPA/heptane at 5 and 50° C. (3 days slurrying).

Results and Discussion: MH2 was predominantly obtained during competitive slurries at 25° C. (Table 11). The solvents that yielded MH2 had a range of different values for water activity. Mixtures of MH1 and MH2 were obtained even though water was absent from the solvent systems (i.e. no conversion to AH was noted). MH2 is preferred in IPA and a mixture of IPA with heptane at 5° C. However, mixtures of MH 1 and MH2 or pure MH1 were produced when a higher temperature was employed (50° C.) (Table 12).

Therefore, competitive slurries indicate that MH2 is preferred at a lower isolation temperature as well as at a higher water activity. Whereas, MH1 is preferred at a higher isolation temperature and a lower water activity.

Further experiments were designed to increase the diversity of solvents/systems studied while still investigating the effect of water activity on the form obtained. This was with a view to define a solvent list for Phase 3 (Solvent Selection). Further saturated solutions were prepared as described in the procedure section using MH1 as supplied.

Some samples dissolved during competitive slurries, this is likely because complete saturation had not occurred. MH2 is again favoured at lower temperature with a high water activity (Table 13). A mixture of MH1 and MH2 was obtained from: heptane at 5° C., IPA or a mixture of IPA: heptane at 50° C. The IPrOAc: 0.5% water mixture ($a_w$=0.35) favoured the formation of MH1 at 50° C., but MH2 at 5° C. Pure MH 1 was also obtained when THF solvent was used at 50° C.

Although MH2 was preferred at low temperature and high $a_w$, MH1 was selected for further development as MH2 converts to MH1 (via AH) and it can be obtained using higher temperatures and lower water activities.

TABLE 11

Competitive slurry of the two hydrates at RT (MH1 and MH2).

| Sample ID | Solvent | Water activity | Observations after solvent addition | Observation after 24 h at 25° C. | XRPD |
|---|---|---|---|---|---|
| 32-01 | EtOAc | — | Suspension | Suspension | MH1 + MH2 |
| 32-02 | 0.5% water/EtOAc | $a_w = 0.3$ | Suspension | Suspension | MH2 |
| 32-03 | 0.8% water/MeOAc | $a_w = 0.4$ | Suspension | Suspension | MH2 |
| 32-04 | 1% water/EtOAc | $a_w = 0.5$ | Suspension | Suspension | MH2 |
| 32-05 | 1.5% water/EtOAc | $a_w = 0.6$ | Suspension | Suspension | MH2 |
| 32-06 | 2% water/EtOAc | $a_w = 0.7$ | Suspension | Suspension | MH2 |
| 32-07 | 2.7% water/EtOAc | $a_w = 0.8$ | Suspension | Suspension | MH2 |
| 32-08 | 7.5% water/MeOAc | $a_w = 0.9$ | Suspension | Suspension | MH2 |
| 32-09 | IPA | — | Suspension | Suspension | MH1 + MH2 |
| 34-02 | IPA:Heptane 1:3 | — | Suspension | Suspension | MH1 + MH2 |
| 34-03 | IPA:Heptane 1:2 | — | Suspension | Suspension | MH1 + MH2 |

TABLE 12

Competitive slurry of the two hydrates 5 and 50° C. (MH1 and MH2).

| Sample ID | Solvent | Temperature (° C.) | Observations after solvent addition | Observations after 24 h | XRPD |
|---|---|---|---|---|---|
| 34-04 | IPA:Heptane 1:3 | 5 | Suspension | Suspension | MH2 |
| 34-05 | IPA:Heptane 1:2 | 5 | Suspension | Suspension | MH2 |
| 34-08 | IPA | 5 | Suspension | Suspension | MH2 |
| 34-06 | IPA:Heptane 1:3 | 50 | Suspension | Suspension | MH1 |
| 34-07 | IPA:Heptane 1:2 | 50 | Suspension | Suspension | MH1 + MH2 |
| 34-09 | IPA | 50 | Suspension | Suspension | MH1 + MH2 |

TABLE 13

Additional competitive slurry of the two hydrates at 5 and 50° C. (MH1 and MH2).

| Sample ID | Solvent | Water activity | Temp. (° C.) | Observations after solvent addition | Observations after 3 days 24 h | XRPD |
|---|---|---|---|---|---|---|
| 35-01 | Water | $a_w = 1$ | 5 | Suspension | Solution | — |
| 35-02 | THF:10% water | $a_w = 0.9$ | 5 | Suspension | Solution | — |
| 35-03 | IPA:10% water | $a_w = 0.75$ | 5 | Suspension | Solution | — |
| 35-04 | Ethanol:7% water | $a_w = 0.5$ | 5 | Suspension | Solution | — |
| 35-05 | IPrOAc:0.5% water | $a_w = 0.35$ | 5 | Suspension | Suspension | MH2 |
| 35-06 | MeOH:5% water | $a_w = 0.2$ | 5 | Suspension | Solution | — |
| 35-07 | IPA | — | 5 | Suspension | Solution | — |
| 35-08 | IPA:Heptane (1:2) | — | 5 | Suspension | Suspension | MH2 |
| 35-09 | THF | — | 5 | Suspension | Suspension | — |
| 35-10 | Heptane | — | 5 | Suspension | Suspension | MH1 + MH2 |
| 35-11 | Water | $a_w = 1$ | 50 | Suspension | Suspension | MH2 |
| 35-12 | THF:10% water | $a_w = 0.9$ | 50 | Suspension | Solution | — |
| 35-13 | IPA:10% water | $a_w = 0.75$ | 50 | Suspension | Suspension | MH2 |
| 35-14 | Ethanol:7% water | $a_w = 0.5$ | 50 | Suspension | Solution | — |
| 35-15 | IPrOAc:0.5% water | $a_w = 0.35$ | 50 | Suspension | Suspension | MH1 |
| 35-16 | MeOH:5% water | $a_w = 0.2$ | 50 | Suspension | Solution | — |
| 35-17 | IPA | — | 50 | Suspension | Suspension | MH1 + MH2 |
| 35-18 | IPA:Heptane (1:2) | — | 50 | Suspension | Suspension | MH1 + MH2 |
| 35-19 | THF | — | 50 | Suspension | Suspension | MH1 |
| 35-20 | Heptane | — | 50 | Suspension | Solution | — |

Structure Comparison of MH1 and MH2

The unit cell and the asymmetric units of MH1 and MH2 were compared (Table 14, measured at 100 K). The two hydrated structures have the same space group and have similar size unit cells. However, the asymmetric units significantly differ.

In MH1 the water and the API (Compound 1) in the asymmetric unit participate in one O—H—O intermolecular hydrogen bond. In addition, there is an intramolecular, bifurcated, asymmetrical hydrogen bond between the nitrogen atom of the imidazopyrazine ring and the nitrogen atoms of pyrimidine and pyrrolidine rings.

In MH2 the water molecule is located between the imidazopyrazine and pyrimidine rings, hence the intramolecular hydrogen bonding present in MH1 is replaced by the intermolecular interaction between water and the API.

TABLE 14

Single crystal structure comparison of MH1 and MH2.

| MH1 | | MH2 | |
|---|---|---|---|
| Crystal system Orthorhombic | | Crystal system Orthorhombic | |
| Space group | P212121 | Space group | P212121 |
| Unite cell dimensions | | Unite cell dimensions | |
| a = 8.97778(18) Å | α = 90° | a = 9.20995(16) Å | α = 90° |
| b = 10.84333(16) Å | β = 90° | b = 11.01308(16) Å | β = 90° |
| c = 21.2411(4) Å | γ = 90° | c = 20.7812(3) Å | γ = 90° |
| Volumne = 2067.80(6) Å³ | | Volumne = 2107.84(6) Å³ | |
| R factor = 3.46% | | R factor = 3.07% | |
| Z' = 4 | | Z' = 4 | |

Results and discussion: The experiments performed in this study showed that MH1 is the most stable form at ambient conditions. Solvent mixtures with water (high water activities) and at lower temperature (5° C.) produced MH2 and hence should be avoided. Although MH1 was solely produced at the end of the crystallization process, care should be taken to avoid AH or MH2 formation.

Example 8. Solubility Assessment of MH1

Procedure: Four solvents were chosen based on the competitive slurry experiments that favored MH1 as well as for diversity. Combinations of those solvents with water ($a_w$=0.35) were also utilized to verify which hydrate is favored. Mixtures of the solvents with heptane (1:1) were used to check for crystal form with a good antisolvent.

MH1 (22×104 mg) was suspended in various solvents (11×0.5 ml) and stirred at either 5 or 50° C. for 24 hours at 750 rpm. The solids were isolated by filtration and centrifugation and the liquors were analysed by HPLC to determine their solubility (relative to a standard made up). The solids were also investigated by XRPD. This procedure was also followed for an additional five solvent systems comprising different ratios of THF:heptane and IPA:heptane at either 5 or 50° C. The isolated solids were investigated by XRPD, HPLC and ¹HNMR.

Results and discussion: Samples that formed clear solutions are considered to have solubility >200 mg/ml (Table 15). This was the case for six of the samples at 50° C. such as: THF, ethanol, IPA, as well as several of those solvents combined with water or heptane. At 5° C., solubility >200 mg/ml was achieved in ethanol and the ethanol mixture with water. A large solubility was also measured using ethanol:heptane (1:1) (170 mg/ml) at 5° C.

The samples produced a variation of MH1 and MH2, as well as a mixture of MH1 with AH at both 5 and 50° C. As IPA and THF gave high solubility at 50° C. (>200 mg/ml) and THF:heptane (1:1) gave MH1 at both temperatures, further solubility assessments were carried out using mixtures of IPA:heptane (1:1, 1:2, 1:3) and THF:heptane (2:1, 1:2) (Table 16).

Based on the solubility observations, it was decided to proceed with the IPA/Heptane (1:3) system for the antisolvent crystallisation, as it gives a low solubility at 5° C. and no MH2 was observed. This solvent/system was selected for solubility and MSZW experiments, to explore the temperature dependence on the solubility of MH1.

TABLE 15

Solubility assessment of MH1.

| Sample ID | Analysis Temperature (° C.) | Media | Weight (mg) | Appearance | Solubility (mg/ml) | XRPD |
|---|---|---|---|---|---|---|
| 40-01 | 5 | THF | 104.46 | Suspension | 79 | MH2 + New peaks |
| 40-02 | | THF:0.8% water | 104.02 | Suspension | 76 | MH2 |
| 40-03 | | THF:Heptane 1:1 | 103.93 | Suspension | 6.3 | MH1 |
| 40-04 | | IPrOAc | 103.90 | Suspension | 11 | MH1 |
| 40-05 | | IPrOAc:0.5% water | 103.89 | Suspension | 3.8 | MH2 |
| 40-06 | | IPrOAc:Heptane 1:1 | 103.86 | Suspension | 1.9 | MH1 |
| 40-07 | | Ethanol | 103.73 | Clear Solution | >200 | — |
| 40-08 | | Ethanol:4.2% water | 103.93 | Clear Solution | >200 | — |
| 40-09 | | Ethanol:Heptane 1:1 | 103.75 | Suspension | 170 | MH1 + AH |
| 40-10 | | IPA | 103.89 | Suspension | 130 | MH1 + AH |
| 40-11 | | Heptane | 103.80 | Suspension | N/A* | MH1 |
| 40-12 | 50 | THF | 103.88 | Clear Solution | >200 | — |
| 40-13 | | THF:0.8% water | 103.85 | Clear Solution | >200 | — |
| 40-14 | | THF:Heptane 1:1 | 106.30 | Suspension & Solid on bottom | 11 | MH1 |
| 40-15 | | IPrOAc | 103.84 | Suspension & Solid on bottom | 6.3 | MH1 + AH |
| 40-16 | | IPrOAc:0.5% water | 103.82 | Suspension & Solid on bottom | 5.6 | MH1 |
| 40-17 | | IPrOAc:Heptane 1:1 | 103.91 | Suspension & Solid on bottom | 2.1 | MH1 |
| 40-18 | | Ethanol | 103.91 | Clear Solution | >200 | — |
| 40-19 | | Ethanol:4.2% water | 103.76 | Clear Solution | >200 | — |
| 40-20 | | Ethanol:Heptane 1:1 | 103.75 | Clear Solution | >200 | — |
| 40-21 | | IPA | 103.85 | Clear Solution | >200 | — |
| 40-22 | | Heptane | 103.94 | Suspension & Solid on bottom | N/A | MH1 + AH |

TABLE 16

Additional solubility assessment for MH1.

| Sample ID | Analysis Temperature (° C.) | Media | Weight (mg) | Appearance | Solubility (mg/ml) | XRPD | PLM |
|---|---|---|---|---|---|---|---|
| 44-01 | 5 | THF:Heptane 2:1 | 103.94 | Suspension & Solid on bottom | 17 | MH2 (small MH1) | Small crystals, some agglomerates |
| 44-02 | | THF:Heptane 1:2 | 104.01 | Suspension & Solid on bottom/sides | 0.33 | MH1 | Small crystals, some agglomerates |
| 44-03 | | IPA:Heptane 1:1 | 104.16 | Suspension & Solid on bottom | 40 | MH1 | Small crystals, some agglomerates |
| 44-04 | | IPA:Heptane 1:3 | 104.12 | Suspension & Solid on bottom | 8 | MH1 | Small crystals, some agglomerates |
| 44-05 | | IPA:Heptane 1:2 | 104.02 | Suspension & Solid on bottom/sides | 14 | MH1 | Small crystals, some agglomerates |
| 44-06 | 50 | THF:Heptane 2:1 | 103.93 | Suspension & Solid on bottom/sides | 21 | MH1 | Large crystals |
| 44-07 | | THF:Heptane 1:2 | 104.01 | Suspension & Solid on bottom/sides | 0.62 | MH1 | Small crystals |
| 44-08 | | IPA:Heptane 1:1 | 104.04 | Clear Yellow Solution | >200 | — | — |
| 44-09 | | IPA:Heptane 1:3 | 103.95 | Suspension & Solid on sides | 10 | MH1 | Small crystals, some agglomerates |
| 44-10 | | IPA:Heptane 1:2 | 103.99 | Suspension & Solid on bottom/sides | 19 | MH1 | Small crystals, some agglomerates |

Example 9. Solubility Studies on MH1 and MH2

Procedure: pH profiling solubility experiments were performed on MH1 and MH2. Solubility was determined in singlicate by suspending sufficient compound in relevant media (1.00 ml) to give a maximum final concentration as shown in the Table 17.

TABLE 17

Maximum Final Sample Concentrations.

| Sample | pH | Max. Concentration (mg/ml) |
|---|---|---|
| A | 1.2 | 1100 |
| B | 4.0 | 140 |
| C | 6.5 | 20 |
| D | 7.5 | 20 |

The suspensions were equilibrated at 25° C., on a Heidolph plate shaker set to 750 rpm for 24 hours. Samples were pH adjusted as required using 0.5M/1M HCl and 0.2M NaOH to within 0.1 of the desired pH unit (where possible). The pHs of the saturated solutions were measured (where applicable) and an appearance was recorded. The suspensions were filtered through a glass fibre C filter (particle retention 1.2 μm) and diluted appropriately. Quantitation was by HPLC with reference to a standard solution of approximately 0.15 mg/ml in DMSO. Different volumes of the standard, diluted and undiluted sample solutions were injected. The solubility was calculated using the peak areas determined by integration of the peak found at the same retention time as the principal peak in the standard injection.

Results and discussion: Upon the addition of media to MH1-A and MH2-A, a thick paste was observed indicating the media had been absorbed, therefore additional media was added to the sample vial and a suspension was observed.

After ca. 1 hour MH1-B, C and D and MH2-C and D were clear solutions, therefore additional material was added to the sample vials.

During the first pH adjustment of MH1-A, little shift in pH was observed when using 0.5M HCl, it was then decided that 1M HCl was to be used as the adjusting solution. The volume capacity of the vial was reached with the pH of the sample was 5.02. The volume in the vial was also reached for MH1-A with a measured pH of 6.63.

TABLE 18

Results from solubility experiments.

| Sample ID | Weight (mg) | Media | Appearance | Final pH | Solubility (mg/ml) |
|---|---|---|---|---|---|
| MH1-A | 1101.4 | pH 1.2 | Clear Solution | 5.02 | >275 |
| MH1-B | 194.1 | pH 4.0 | Clear Solution | 4.02 | >106 |
| MH1-C | 193.7 | pH 6.5 | Clear Solution | 6.53 | >164 |
| MH1-D | 191.9 | pH 7.5 | Solid on bottom | 7.51 | 62 |
| MH2-A | 1109.1 | pH 1.2 | Clear Solution | 6.63 | >275 |
| MH2-A | 140.9 | pH 4.0 | Clear Solution | 3.76 | >99 |
| MH2-A | 191.7 | pH 6.5 | Clear Solution | 6.47 | >147 |
| MH2-A | 193.3 | pH 7.5 | Solid on bottom | 7.52 | 58 |

The solubility for the A samples (initially in pH 1.2 media) was determined as >275 mg/ml, however, it is worth noting that the pH was not able to be maintained at pH 1.2 as the volume capacity of the vial was reached. Therefore, the solubility value obtained is for the final pH. These experiments were repeated using a reverse addition approach.

Solubility Repeat

Procedure: pH 1.2 buffered media (0.4 ml) was added to two separate 7 ml vials. For each compound, material was added in portions to the pH 1.2 media. After each addition of compound, the vial was vortex mixed and the pH and appearance was recorded. The samples were adjusted to pH 1.2 with 1M HCl to within 0.05 of the desired pH unit. This was repeated until no further material was available (~400 mg for each form, which would give a maximum concentration of around 1000 mg/ml if no adjustment was required).

Results and discussion: Clear solutions were observed for both samples due to the volume of adjusting solution required. However, the pH of both solutions was maintained at pH 1.2 throughout.

TABLE 19

Solubility of MH1 and MH2 at pH 1.2

| Sample | Solubility (mg/ml) |
|---|---|
| MH1 | >153 |
| MH2 | >161 |

Example 10. Crystallization Process for the Preparation of MH 1

Dry (KF≤0.1%) 2-propanol (67 kg) was charged into the reactor under Na followed by crude solid Compound 1 (20.4 kg). Purified water (1 kg) and dry 2-propanol (3 kg) were subsequently added and the reactor temperature control was adjusted to 27-35° C. The resulting reaction mixture was stirred under $N_2$ protection until all solid material had dissolved. Optionally, an in-process control (IPC) sample (KF) was performed to determine the water contents of the reaction mixture and enough dry 2-propanol was added to bring the water content to 1.0% (as verified by KF).

The temperature of the reaction mixture was adjusted to 22-28° C. and seed crystals (0.24 kg) were added. The resulting reaction mixture was stirred for 0.5-2.0 h at 22-28° C. n-Heptane (246 kg) was charged slowly into the reactor at 22-28° C. using a pump, such as a diaphragm pump, and the resulting reaction mixture was stirred at 22-28° C. In order to achieve complete desupersaturation and maximize yield, the resulting reaction mixture may be stirred for 8-12 hr. Optionally, at this point an IPC sample was taken to determine moisture, residual Compound 1 in the supernatant, purity and crystallinity of the precipitated solid.

The reaction mixture was filtered at 22-28° C. and the resulting solid was washed with n-heptane (27.8 kg). The filter cake was pressed until dried and subsequently dried under a flow of $N_2$ for 1-2 hrs. Optionally, at this point an IPC sample confirmed purity and crystallinity of the isolated solid.

The solid was dried over a saturated solution of sodium chloride in the drying chamber at 20-27° C. under a constant flow of nitrogen for 10-18 hr. The solid was removed from the dryer, sieved and packed into a drum lined with LDPE bags. A release sample confirmed moisture (KF=4.2%) and crystallinity (XRPD: MH 1) along with other purity related release methods. Yield: 17.46 kg MH1.

The invention claimed is:

1. A monohydrate crystalline form of 6-[(3S,4S)-4-methyl-1-(pyrimidin-2-ylmethyl)pyrrolidin-3-yl]-3-tetrahydropyran-4-yl-7H-imidazo[1,5-a]pyrazin-8-one

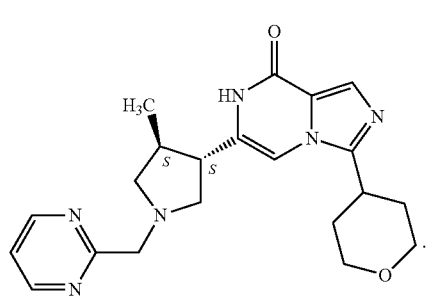

(Compound 1)

2. A monohydrate crystalline form of Compound 1

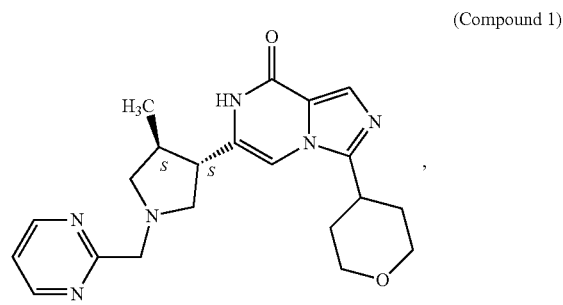

(Compound 1)

wherein the monohydrate crystalline form is Monohydrate Form 1 (MH1), having an XRPD pattern comprising peaks of 2θ angles at 9.1, 11.5, 16.2, 16.7, 18.2, 18.9, 19.8, 22.6, and 26.4 degrees 2θ, each ±0.2 degrees 2θ.

Figure 2A:
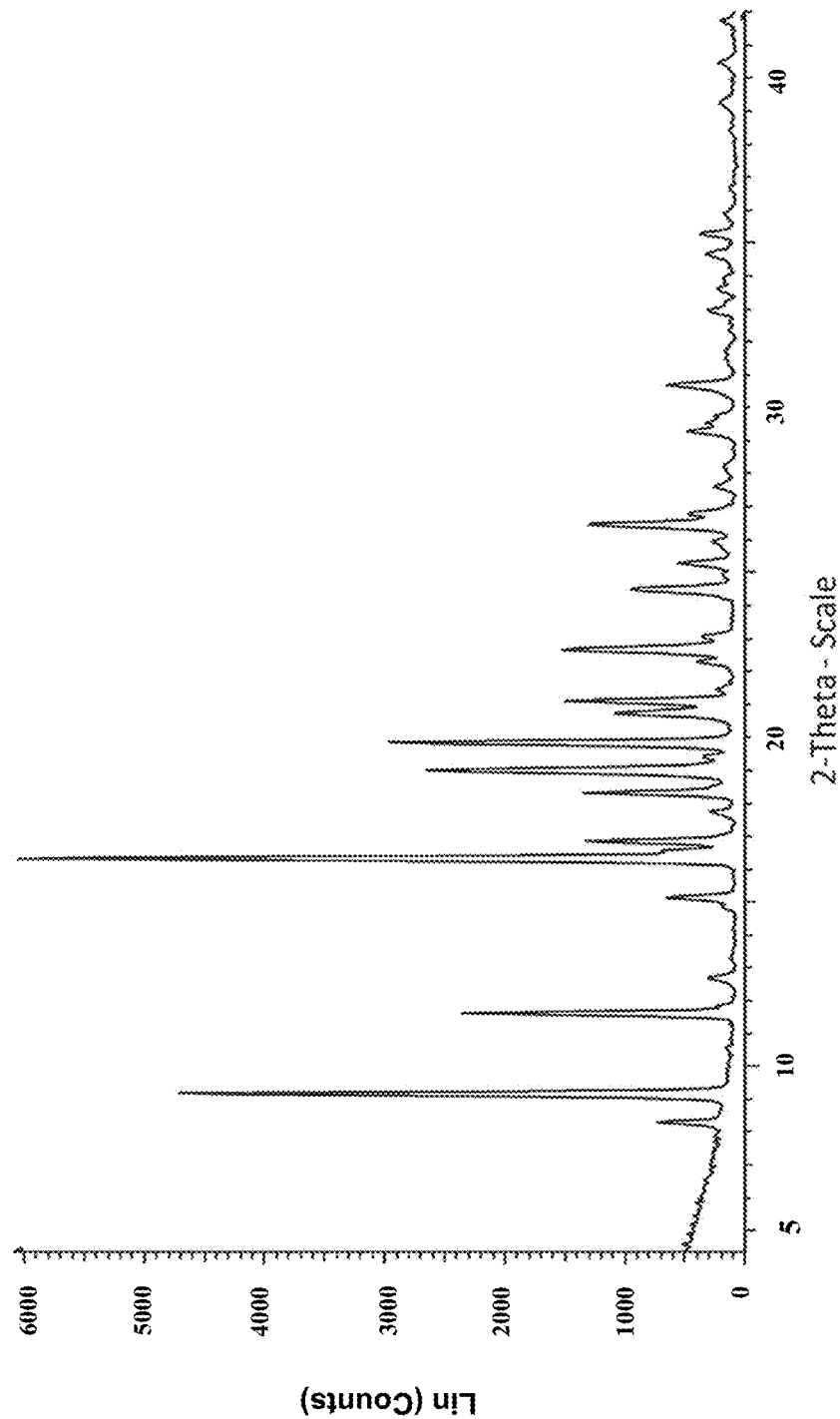
FIG. 2A is the experimental XRPD pattern of MH1 crystal at room temperature.
Figure 2B:
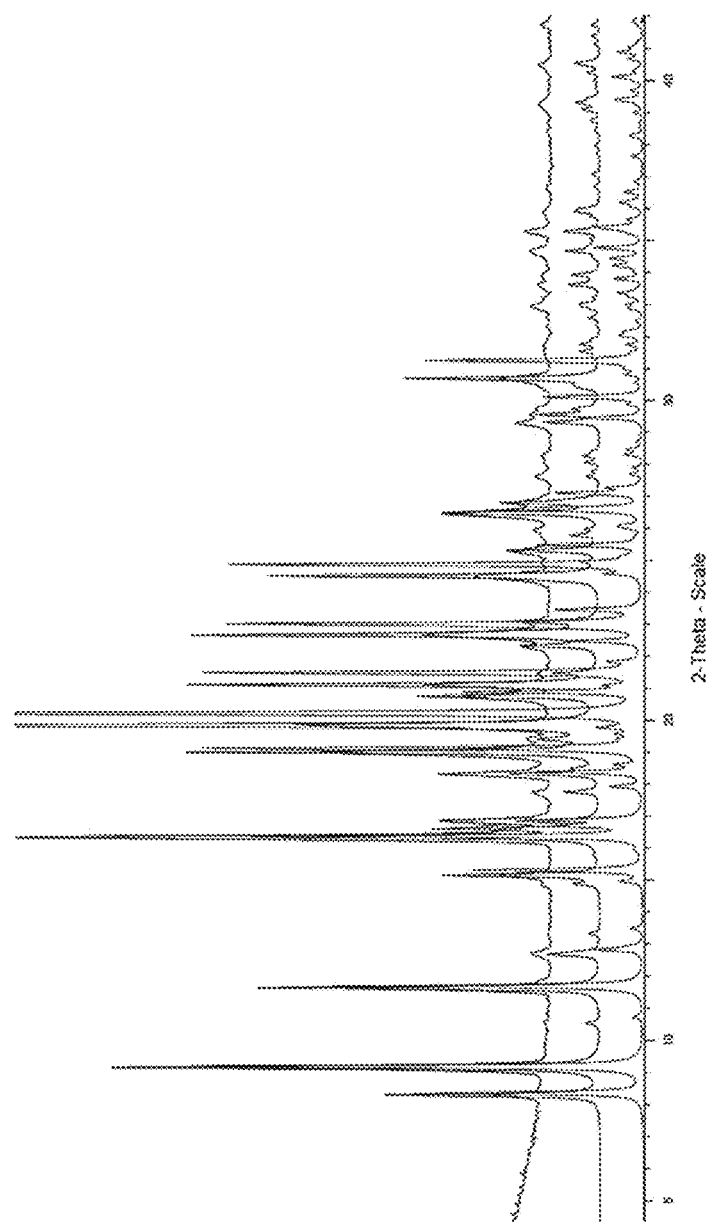
FIG. 2B is an overlay of the experimental XRPD pattern of MH1 at room temperature (top line) and the calculated XRPD pattern of MH1 at 293K (middle line) and 100 K (bottom line).

3. The monohydrate crystalline form of claim 2, having an XRPD pattern substantially the same as shown in FIG. 2A.

4. The monohydrate crystalline form of claim 2, having a dehydration endothermic peak at 40-100° C. and a melting endothermic peak at about 184.4° C. in a differential scanning calorimetry (DSC) thermogram.

5. The monohydrate crystalline form of claim 2, having a DSC thermogram substantially in accordance with FIG. 5.

6. The monohydrate crystalline form of claim 2, exhibiting dehydration between ambient and about 90° C. with a weight loss of about 3.8% in a thermogravimetric analysis (TGA).

7. The monohydrate crystalline form of claim 2, having a TGA substantially in accordance with FIG. 5.

8. The monohydrate crystalline form of claim 2, having characteristic absorptions at about 782 $cm^{-1}$, 1123 $cm^{-1}$, 1562 $cm^{-1}$ and 1655 $cm^{-1}$ in an infrared (IR) spectrum.

9. The monohydrate crystalline form of claim 2, having an infrared spectrum substantially in accordance with FIG. 3.

10. A monohydrate crystalline form of Compound 1

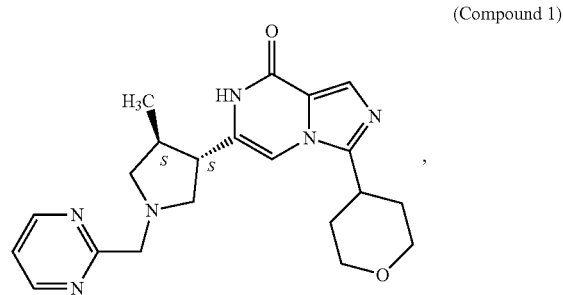

(Compound 1)

wherein the monohydrate crystalline form is Monohydrate Form 2 (MH2), having an XRPD pattern comprising peaks of 2θ angles at 9.0, 11.6, 15.0, 16.0, 18.6, 19.1, 20.4, or 20.6 degrees 2θ, each ±0.2 degrees 2θ.

11. The monohydrate crystalline form of claim 10, having an XRPD pattern substantially the same as the XRPD pattern shown in FIG. 7A.

12. The monohydrate crystalline form of claim 10, having an endothermic peak at 59.1° C. (±5° C.) and at 184.7° C. (±5° C.) in a differential scanning calorimetry (DSC) thermogram.

13. The monohydrate crystalline form of claim 10, having a DSC thermogram substantially in accordance with FIG. 9.

14. The monohydrate crystalline form of claim 10, exhibiting dehydration at about 25° C. to about 100° C. with a weight loss of about 4.4% in a thermogravimetric analysis (TGA).

15. The monohydrate crystalline form of claim 10, having a TGA substantially in accordance with FIG. 9.

16. The monohydrate crystalline form of claim 2, which is at least 95, 96, 97, 98, or 99% purified.

17. A pharmaceutical composition comprising the monohydrate crystalline form of claim 2, and a pharmaceutically acceptable excipient.

18. The pharmaceutical composition of claim 17, wherein the monohydrate crystalline form is present in an amount of at least about 90%, 91%, 92%, 93%, 94%, 95%, 96%, 97%, 98%, or 99% by weight.

19. A pharmaceutical composition comprising the monohydrate crystalline form of claim 10, and a pharmaceutically acceptable excipient.

20. The pharmaceutical composition of claim 19, wherein the monohydrate crystalline form is present in an amount of at least about 90%, 91%, 92%, 93%, 94%, 95%, 96%, 97%, 98%, or 99% by weight.

\* \* \* \* \*